(12) United States Patent
Hashihayata et al.

(10) Patent No.: US 7,977,336 B2
(45) Date of Patent: Jul. 12, 2011

(54) AMINOPYRIMIDINE DERIVATIVES AS PLK1 INHIBITORS

(75) Inventors: Takashi Hashihayata, Tsukuba (JP); Mikako Kawamura, Tsukuba (JP); Morihiro Mitsuya, Tsukuba (JP); Yoshiyuki Sato, Hanamigawa-ku (JP)

(73) Assignee: Banyu Pharmaceutical Co. Ltd, Tokyo (JP)

( * ) Notice: Subject to any disclaimer, the term of this patent is extended or adjusted under 35 U.S.C. 154(b) by 796 days.

(21) Appl. No.: 12/002,546

(22) Filed: Dec. 18, 2007

(65) Prior Publication Data

US 2008/0305081 A1 Dec. 11, 2008

Related U.S. Application Data

(60) Provisional application No. 60/897,515, filed on Jan. 25, 2007.

(30) Foreign Application Priority Data

Dec. 28, 2006 (JP) ................... 2006-356575
Oct. 11, 2007 (JP) ................... 2007-265783

(51) Int. Cl.
*C07D 403/04* (2006.01)
*A61K 31/506* (2006.01)

(52) U.S. Cl. .......... 514/252.18; 514/275; 544/295; 544/324

(58) Field of Classification Search .......... 544/295, 544/324; 514/252.18, 275
See application file for complete search history.

(56) References Cited

FOREIGN PATENT DOCUMENTS

| | | | |
|---|---|---|---|
| CA | 2577947 | * | 3/2006 |
| EP | 1790650 | | 5/2007 |
| JP | 2006/502164 A | | 1/2006 |
| WO | 03/000682 A1 | | 1/2003 |
| WO | 2004/043936 A1 | | 5/2004 |
| WO | WO2005/092899 | | 10/2005 |

OTHER PUBLICATIONS

Simone, Cecil Textbook of Medicine, 20th Edition, vol. 1, pp. 1004-1010, 1996.*
Feng, D et al., Bioorganic & Medicinal Chemistry Letters, vol. 16, pp. 5978-5982 (2006), "Synthesis and SAR of 2-(4-fluorophenyl)-3-pyrimidin-4-ylimidazo[1,2-alpha]pyridine derivatives as anticoccidial agents".

* cited by examiner

*Primary Examiner* — Deepak Rao
(74) *Attorney, Agent, or Firm* — Nicole M. Beeler; David A. Muthard

(57) ABSTRACT

The present invention relates to a compound represented by Formula [I]:

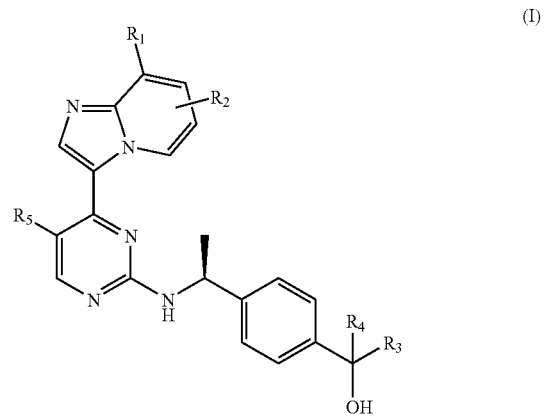

or a pharmaceutically acceptable salt or ester thereof, wherein $R_1$ and $R_2$, which may be the same or different, are each a hydrogen atom, a lower alkyl group, a cycloalkyl group, or the like; $R_3$ and $R_4$, which may be the same or different, are each a hydrogen atom, a lower alkyl group, $NR_aR_b$, a phenyl group, a lower alkyl group substituted with a phenyl group, a 4- to 7-membered aliphatic heterocyclic group, a lower alkyl group substituted with a 4- to 7-membered aliphatic heterocyclic group, a 5- or 6-membered aromatic heterocyclic group, a lower alkyl group substituted with a 5- or 6-membered aromatic heterocyclic group, or the like; and $R_5$ is a hydrogen atom, a cyano group, a halogen atom, or a lower alkyl group.

12 Claims, No Drawings

AMINOPYRIMIDINE DERIVATIVES AS PLK1 INHIBITORS

PRIORITY CLAIM

This application claims priority from Japanese Provisional Application Serial No. 2007-265783, filed Oct. 11, 2007, U.S. Provisional Application Ser. No. 60/897,515 filed on Jan. 25, 2007, and Japanese Provisional Application Serial No. 2007-356575, filed on Dec. 28, 2006.

TECHNICAL FIELD

The present invention relates to a novel substituted aminopyrimidine derivative useful in the field of medicine, which inhibits proliferation of tumor cells on the basis of an inhibitory effect against PLK1, thereby exhibiting an antitumor effect, and to a PLK1 inhibitor and an antitumor agent containing the derivative.

BACKGROUND ART

Proliferation is known to be active generally in cancerous cells compared with normal cells, and in many cases, it is thought that the disorderliness of proliferation due to an abnormality in the cell cycle control mechanism is the cause of cancer. A mitotic phase (M phase) of the cell cycle is the step of equally partitioning a chromosome into daughter cells, and a strict control in the process is essential for cell proliferation and survival. Therefore, it is believed that the inhibition of M phase progression is an effective means for inhibiting cell proliferation, and practically, antitumor agents targeting M phase such as taxol, vincristine, or the like have been achieving clinically effective results.

It has been known that many steps in the M phase progression are controlled by protein kinases which phosphorylate proteins. A PLK (polo-like kinases) family is serine-threonine kinase playing an important role in controlling the cell cycle including M phase, and this family includes four similar proteins of PLK1, PLK2, PLK3, and SAK (Nature. Review. Molecular. Cell Biology (Nat. Rev. Mol. Cell. Biol.), Vol. 5, 429, (2004)). Of these, PLK1 is known to participate in a plurality of important stages at M phase in mammalian cells: PLK1 has been reported to participate in each step of entering the M phase, control of centrosome, separation of chromosome, and cytokinesis, by phosphorylating various substrates (Nature. review. Molecular. Cell Biology.) (Nat. Rev. Mol. Cell Biol.), Vol. 5, 429, (2004)).

Moreover, there are many reports suggesting that PLK1 is overexpressed in various cancerous tissues in humans. For example, PLK1 is approved to be overexpressed in non small cell lung cancer (Oncogene, Vol. 14, 543, (1997)) and head and neck cancer (Cancer Research, Vol. 15, 2794, (1999)), and there are data showing that the overexpression of PLK1 is in relation with a prognosis of patients with those diseases. It is also reported that the expression of PLK1 is increased in other types of cancer such as in colon cancer, esophageal cancer, ovarian cancer, and melanoma. Such reports suggest that the overexpression of PLK1 is related to malignant alteration of cells in one way or another, and also that the function of PLK1 is important particularly in the progression of M phase in cancer cells.

From these facts, PLK1 is thought to be a possible target for antitumor approach. In fact, there are many reports on experiments for examining the inhibitory effect on the function of PLK1 against cancerous cells by using various experimental techniques. For example, it is reported that in the experiment of expressing a function-inhibited PLK1 mutant in cells by using a viral vector, PLK1 inhibition promotes the cancerous cell-selective apoptosis (Cell growth & Differentiation (Cell growth & Diff.), Vol. 11, 615, (2000)). There is also a report showing that PLK1 siRNA induces cancer cell growth inhibition and apoptosis (Journal of National Cancer Institute (J. Natl. Cancer Inst.), Vol. 94, 1863 (2002)). In addition, it is reported that PLK1 shRNA (Journal of National Cancer Institute (J. Natl. Cancer Inst.), Vol. 96, 862, (2004)), or an antisense oligonucleotide (Oncogene, Vol. 21, 3162 (2002)) gives an antitumor effect in a mouse xenograft model. Those experimental results show that inhibition of the PLK1 activity causes the promotion of cancer cell growth inhibition and apoptosis, and strongly suggest that a PLK1 inhibitor be an effective antitumor agent.

The present inventors have filed a patent application on a substituted imidazole derivative having a PLK inhibitory effect (International Publication WO2006/025567).

DISCLOSURE OF THE INVENTION

It is an object of the present invention to provide a novel aminopyrimidine derivative that exhibits a PLK1 inhibitory effect and excellent cytostatic (cell growth inhibitory) activity based on the inhibitory effect, thereby to develop an antitumor agent based on such PLK1 inhibitory effect.

In order to attain such object, the inventors of the present invention synthesized a wide range of aminopyrimidine derivatives, and discovered that a compound represented by Formula [I] exhibits excellent PLK1 inhibitory effect and cytostatic activity based on the inhibitory effect, thus completing the invention.

That is, the present invention relates to a compound represented by the Formula [I]:

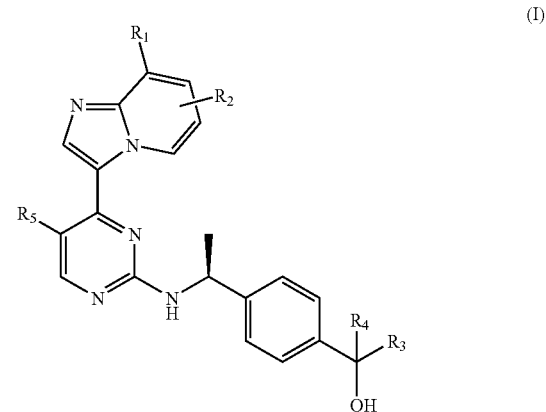

wherein $R_1$ and $R_2$, which may be the same or different, are each a hydrogen atom; a substituent selected from <Substituent Group α>; a lower alkyl group which may be substituted with one or more substituents selected from <Substituent Group α>; or a cycloalkyl group having 3 to 6 carbon atoms, which may be substituted;

$R_3$ and $R_4$, which may be the same or different, are each:
a) a hydrogen atom;
b) a lower alkyl group substituted with $NR_aR_b$, where $R_a$ and $R_b$, which may be the same or different, are each a hydrogen atom, a lower alkyl group which may be substituted, a benzyl group which may be substituted, or a cycloalkyl group which may be substituted;
c) a substituent selected from <Substituent Group β>;

d) a lower alkyl group which may be substituted with one or more substituents selected from <Substituent Group β>;

e) a lower alkenyl group which may be substituted with one or more substituents selected from <Substituent Group β>;

f) a phenyl group;

g) a lower alkyl group substituted with a phenyl group;

h) a 4- to 7-membered aliphatic heterocyclic group;

i) a lower alkyl group substituted with a 4- to 7-membered aliphatic heterocyclic group;

j) a 5- to 6-membered aromatic heterocyclic group; or k) a lower alkyl group substituted with a 5- to 6-membered aromatic heterocyclic group, wherein the phenyl group, the aliphatic heterocyclic group, and the aromatic heterocyclic group each independently may be substituted with one or more substituents, which may be the same or different, selected from the following 1) to 4):

1) a lower alkyl group;

2) a substituent selected from <Substituent Group β>;

3) a lower alkyl group substituted with one or more substituents selected from <Substituent Group β>; and 4) a cycloalkyl group having 3 to 6 carbon atoms, which may be substituted with one or more substituents selected from <Substituent Group β>, and the aliphatic heterocyclic group may include an unsaturated bond, and the lower alkyl group as defined in the b), g), i), and k) above may be suitably substituted, or alternatively, $R_3$ and $R_4$ are taken together to form a 4- to 7-membered aliphatic heterocyclic group, wherein the aliphatic heterocyclic group may be substituted with one or more substituents, which may be the same or different, selected from the following 1) to 4):

1) a lower alkyl group;

2) a substituent selected from <Substituent Group β>;

3) a lower alkyl group substituted with one or more substituents selected from <Substituent Group β>; and 4) a cycloalkyl group having 3 to 6 carbon atoms, which may be substituted with one or more substituents selected from <Substituent Group β>, and the aliphatic heterocyclic group may include an unsaturated bond; and $R_5$ is a hydrogen atom, a cyano group, a halogen atom, or a lower alkyl group.

<Substituent Group α> and <Substituent Group β> are defined as below:

<Substituent Group α>: a halogen atom, a hydroxy group, a nitro group, a cyano group, an amino group, a carbamoyl group, an aminosulfonyl group, an imino group, a lower alkylamino group, a di-lower alkylamino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, and a carboxyl group, <Substituent Group β>: a halogen atom, a hydroxy group, a nitro group, a cyano group, an amino group, a carbamoyl group, an aminosulfonyl group, an imino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, a carboxyl group, and a benzyl group;

or a pharmaceutically acceptable salt or ester thereof. The compound represented by the above Formula (I) includes all of the existing enantiomers and diastereomers in addition to racemates of the compound.

The invention also relates to a combined preparation for simultaneous, separate, or sequential administration in the treatment of cancer, where the combined preparation includes two separate preparations of:

a preparation including, together with a pharmaceutically acceptable carrier or diluent, the compound represented by the Formula [I] or a pharmaceutically acceptable salt or ester thereof; and a preparation including, together with a pharmaceutically acceptable carrier or diluent, an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents, or a pharmaceutically acceptable salt or ester thereof, wherein:

the antitumor alkylating agents are nitrogen mustard N-oxide, cyclophosphamide, ifosfamide, melphalan, busulfan, mitobronitol, carboquone, thiotepa, ranimustine, nimustine, temozolomide, and carmustine;

the antitumor antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, and pemetrexed disodium;

the antitumor antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin;

the plant-derived antitumor agents are vincristine, vinblastin, vindesine, etoposide, sobuzoxane, docetaxel, paclitaxel, and vinorelbine;

the antitumor platinum complex compounds are cisplatin, carboplatin, nedaplatin, and oxaliplatin;

the antitumor camptothecin derivatives are irinotecan, topotecan, and camptothecin;

the antitumor tyrosine kinase inhibitors are gefitinib, imatinib, and erlotinib;

the monoclonal antibodies are cetuximab, bevacizumab, rituximab, bevacizumab, alemtuzumab, and trastuzumab;

the interferons are interferon α, interferon α-2a, interferon α-2b, interferon β, interferon γ-1a, and interferon γ-nl;

the biological response modifiers are krestin, lentinan, sizofuran, picibanil, and ubenimex; and the other antitumor agents are mitoxantrone, L-asparaginase, procarbazine, dacarbazine, hydroxycarbamide, pentostatin, tretinoin, alefacept, darbepoetin alfa, anastrozole, exemestane, bicalutamide, leuproreline, flutamide, fulvestrant, pegaptanib octasodium, denileukin diftitox, aldesleukin, thyrotropin alpha, arsenic trioxide, bortezomib, capecitabine, and goserelin.

In addition, the invention relates to a pharmaceutical composition including, together with a pharmaceutically acceptable carrier or diluent, the compound represented by the Formula [I] or a pharmaceutically acceptable salt or ester thereof; and an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, biological response modifiers, and other antitumor agents (wherein, the definition of each antitumor agent has the same meaning as defined above), or a pharmaceutically acceptable salt or ester thereof.

The invention also relates to a method for treating cancers, comprising administering simultaneously, separately, or sequentially a therapeutically effective amount of the compound represented by Formula [I] above or a pharmaceutically acceptable salt or ester thereof, in combination with a therapeutically effective amount of an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents (wherein, the definition of each antitumor agent has the same meaning as defined above), or a pharmaceutically acceptable salt or ester thereof.

The invention further relates to the use of a PLK1 inhibitor for the manufacture of a medicament in the treatment of cancer, and the use of a PLK1 inhibitor in combination with an antitumor agent for the manufacture of a medicament in the treatment of cancer. In addition, the invention relates to a method for treating cancers in mammals (particularly in humans) which comprises administering a therapeutically effective amount of a PLK1 inhibitor to the mammals, and to a method for treating cancers in mammals (particularly in humans) which comprises administering a therapeutically effective amount of a PLK1 inhibitor to the mammals in combination with a therapeutically effective amount of an antitumor agent.

Further, the invention relates to an agent for treating cancers including a PLK1 inhibitor as an active ingredient, and to an agent for treating cancers which comprises, together with an antitumor agent, a PLK1 inhibitor as an active ingredient.

Hereinafter, the symbols and terms described in the present specification will be explained.

The "lower alkyl group" in the above Formula (I) refers to a straight-chained or branched alkyl group having 1 to 6 carbon atom(s), and examples thereof include a methyl group, an ethyl group, a propyl group, an isopropyl group, a butyl group, an isobutyl group, a sec-butyl group, a tert-butyl group, a pentyl group, a hexyl group, and the like.

The "lower alkenyl group" in the above Formula (I) refers to a straight-chained or branched alkenyl group having 2 to 6 carbon atoms, and examples thereof include a vinyl group, a 1-propenyl group, an allyl group, an isopropenyl group, a 1-butenyl group, a 3-butenyl group, a 1,3-butanedienyl group, a 2-pentenyl group, a 4-pentenyl group, a 1-hexenyl group, a 3-hexenyl group, a 5-hexenyl group, and the like.

The "cycloalkyl group" in the above Formula (I) refers to a 3- to 8-membered alicyclic group and examples thereof include a cyclopropyl group, a cyclobutyl group, a cyclopentyl group, a cyclohexyl group, a cycloheptyl group, a cyclooctyl group, and the like, and preferably refers to a 3- to 6-membered alicyclic group. Preferred examples include a cyclopropyl group, a cyclobutyl group, a cyclopentyl group, and a cyclohexyl group.

The "aliphatic heterocyclic group" in the above Formula (I) refers to a saturated or unsaturated aliphatic heterocyclic group generally having at least one atom selected from a nitrogen atom, an oxygen atom, and a sulfur atom, in addition to carbon atoms, that is a mono-, di-, or tricyclic fused ring. Examples include an azetidyl group, a pyrrolidinyl group, a piperidinyl group, a piperazinyl group, a morpholino group, a tetrahydrofuranyl group, an imidazolidinyl group, a thiomorpholino group, a tetrahydroquinolyl group, a tetrahydroisoquinolyl group, and the like. The "4- to 7-membered aliphatic heterocyclic group" in the above Formula (I) refers to a saturated or unsaturated aliphatic heterocyclic group that is a 4- to 7-membered monocyclic ring, and examples thereof include an azetidyl group, a pyrrolidinyl group, a piperidinyl group, a piperazinyl group, a morpholino group, a tetrahydrofuranyl group, an imidazolidinyl group, a thiomorpholino group, and the like.

The "aromatic heterocyclic group" in the above Formula (I) generally refers to a heterocyclic group with aromatic properties containing at least one hetero atom such as a nitrogen atom, an oxygen atom, or the like, and examples thereof include 5- to 7-membered monocyclic heterocyclic groups and fused-ring heterocyclic groups formed by fusion of a 3- to 8-membered ring to the monocyclic heterocyclic group, and the like. Specifically, a thienyl group, a pyrrolyl group, a furyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzoimidazolyl group, a benzofuranyl group, and the like may be mentioned. The "5- or 6-membered aromatic heterocyclic group" in the above Formula (I) refers to a 5- or 6-membered monocyclic heterocyclic group with aromatic properties, and examples thereof include a thienyl group, a pyrrolyl group, a furyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, and the like.

The "halogen atom" in the above Formula (I) may be exemplified by a fluorine atom, a chlorine atom, a bromine atom, an iodine atom, or the like, and among these, for example, a fluorine atom, a chlorine atom, and a bromine atom are preferred.

The "lower alkylamino group" in the above Formula (I) refers to a substituent formed by N-substitution of the above "lower alkyl group" to an amino group, and examples thereof include an N-methylamino group, an N-ethylamino group, an N-propylamino group, an N-isopropylamino group, an N-butylamino group, an N-isobutylamino group, an N-tert-butylamino group, an N-pentylamino group, an N-hexylamino group, and the like.

The "di-lower alkylamino group" in the above Formula (I) refers to a substituent formed by N,N-disubstitution of the above "lower alkyl group" to an amino group, and examples thereof include an N,N-dimethylamino group, an N,N-diethylamino group, an N,N-dipropylamino group, an N, N-diisopropylamino group, an N,N-dibutylamino group, an N,N-diisobutylamino group, an N,N-ditert-butylamino group, an N,N-dipentylamino group, an N,N-dihexylamino group, an N-ethyl-N-methylamino group, an N-methyl-N-propylamino group, and the like.

The "amino(loweralkyl) group" in the above Formula (I) refers to a straight-chained or branched alkyl group having 1 to 6 carbon atom(s) substituted with an amino group, and examples thereof include an aminomethyl group, a 1-aminoethyl group, a 2-aminoethyl group, 1-aminopropyl group, a 2-aminopropyl group, an aminoisopropyl group, a 1-aminobutyl group, a 2-aminobutyl group, an aminoisobutyl group, an amino sec-butyl group, an amino tert-butyl group, a 1-aminopentyl group, a 2-aminopentyl group, a 3-aminopentyl group, a 1-aminohexyl group, a 2-aminohexyl group, a 3-aminohexyl group, and the like.

The "lower alkylsulfonyl group" in the above Formula (I) refers to a substituent formed by bonding the above "lower alkyl group" to a sulfur atom of a sulfonyl group, and examples thereof include a methylsulfonyl group, an ethylsulfonyl group, a butylsulfonyl group, and the like.

The "lower alkylsulfonylamino group" in the above Formula (I) refers to a substituent formed by N-substitution of the above "lower alkylsulfonyl group" to an amino group, and examples thereof include a methylsulfonylamino group, an ethylsulfonylamino group, a butylsulfonylamino group, and the like.

The "lower alkoxy group" in the above Formula (I) refers to a group formed by bonding the "lower alkyl group" to an oxygen atom, and examples thereof include a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, and the like.

The "lower alkoxycarbonyl group" in the above Formula (I) refers to a group formed by bonding the "lower alkoxy group" to a carbonyl group, and specific examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a neopentyloxycarbonyl group, a hexyloxycarbonyl group, an isohexyloxycarbonyl group, and the like.

The "lower alkoxycarbonylamino group" in the above Formula (I) refers to a group formed by N-substitution of the "lower alkoxycarbonyl group" to an amino group, and specific examples thereof include a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a pentyloxycarbonylamino group, a neopentyloxycarbonylamino group, a hexyloxycarbonylamino group, an isohexyloxycarbonylamino group, and the like.

The "lower alkanoyl group" in the above Formula (I) refers to a group formed by bonding the "lower alkyl group" to a carbonyl group, and is preferably a group in which the alkyl group having 1 to 5 carbon atom(s) is bonded to a carbonyl group. For example, an acetyl group, a propionyl group, a butyryl group, an isobutyryl group, a valeryl group, an isovaleryl group, a pivaloyl group, a pentanoyl group, and the like can be mentioned.

The "lower alkanoyloxy group" in the above Formula (I) refers to a group formed by bonding of the "lower alkanoyl group" to an oxygen atom, and examples thereof include an acetyloxy group, a propionyloxy group, a butyryloxy group, an isobutyryloxy group, a valeryloxy group, an isovaleryloxy group, a pivaloyloxy group, a pentanoyloxy group, and the like.

The "lower alkylthio group" in the above Formula (I) refers to a substituent formed by bonding of the "lower alkyl group" to a sulfur atom, and examples thereof include a methylthio group, an ethylthio group, a butylthio group, and the like.

The term "PLK" represents a polo-like kinase.

The term "PLK1" is one of the PLK (polo-like kinase) family members constituted by PLK1, PLK2, PLK3, and SAK.

The term "PLK1 inhibitor" is a drug for inhibiting polo-like kinase 1.

The terms "pharmaceutically acceptable salt or ester" and "pharmaceutically acceptable carrier or diluent" will be explained later.

The term "treatment of cancer" ("treating cancer") as used in the present specification means the inhibition of cancer cell growth by administering an antitumor agent to cancer patients. The treatment preferably regresses the cancer cell growth, that is, reduces the tumor size which can be measured. The treatment more preferably eradicates cancer completely.

The term "cancer" as used in the present specification includes solid tumors and hematopoietic cancers. Examples of the solid tumors include cerebral cancer, head and neck cancer, esophageal cancer, thyroid cancer, small cell lung cancer, non-small cell lung cancer, breast cancer, gastric cancer, gall bladder/bile duct cancer, hepatic cancer, pancreatic cancer, colon cancer, rectal cancer, ovarian cancer, chorioepithelioma, uterine cancer, cervical cancer, renal pelvic/ureteral cancer, urinary bladder cancer, prostate cancer, penile cancer, testicular cancer, embryonal cancer, Wilms' tumor, skin cancer, malignant melanoma, neuroblastoma, osteosarcoma, Ewing's sarcoma, soft tissue sarcoma, and the like. Examples of the hematopoietic cancers include acute leukemia, chronic lymphatic leukemia, chronic myelogenous leukemia, true polycythemia, malignant lymphoma, multiple myeloma, non-Hodgkin's lymphoma, and the like.

The term "preparation" as used in the present specification includes oral preparations and parenteral preparations. The oral preparation is exemplified by a tablet, capsule, powder, granule, or the like, preferably a tablet, capsule, or the like. The parenteral preparation is exemplified by a sterilized liquid preparation such as solution, suspension, and the like, which is specifically an injectable preparation, drip infusion, and the like, and preferably is an intravenous injection preparation and intravenous drip.

The term "combined preparation" as used in the present specification refers to the preparation including two or more kinds for simultaneous, separate, or sequential administration in the treatment, which may be provided as a kit-type preparation or a pharmaceutical composition. The "combined preparation" also includes preparations prepared by further combining one or more preparation(s) to the above described combined preparation including two separate preparations which is useful in the treatment of cancer.

In addition to the two separate preparations, one or more preparation(s) including at least one antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents (wherein, the definition of each antitumor agent has the same meaning as defined above), or a pharmaceutically acceptable salt or ester thereof, may be further combined, together with a pharmaceutically acceptable carrier or diluent. In this case, the further-combined at least one preparation may be administered simultaneously, separately, or sequentially with the two separate preparations. The combined preparation including three preparations can be exemplified by: a preparation comprising the compound represented by the above Formula (I); a preparation comprising 5-fluorouracil; and a preparation comprising leucovorin.

For the combined preparation, both of two separate preparations may be either an oral preparation or parenteral preparation, or alternatively, one of the two separate preparations may be an oral preparation while the other one being a parenteral preparation (injectable preparation or drip infusion).

For the "preparation" according to the invention, a therapeutically effective amount of the compound according to the invention may be included, together with a pharmaceutically acceptable carrier or diluent. The formulation technique is thought to be the technical common knowledge for those skilled in the technical field, which is therefore well known. Preferably, such preparation can be formed into, together with a pharmaceutically acceptable carrier or diluent, a preparation for oral administration, intravenous infusion, or injection, using a number of methods generally known to those skilled in the art.

The term "administration" as used in the present specification includes parenteral administration and/or oral administration in the case of using the combined preparation according to the invention. That is, when administering the combined preparation, both may be parenterally administered, or one may be parenterally administered while the other one being administered orally, or otherwise, both may be orally administered. Here, the "parenteral administration" includes, for example, intravenous administration, subcutaneous administration, intramuscular administration, and the like, and preferably includes the intravenous administration. When administering three or more preparations in combination, at least one preparation may be parenterally administered, preferably intravenously administered, and more preferably administered by an intravenous drip or intravenous injection. In addition, for the case of administering three or more preparations in combination, any of the preparations may be an oral preparation or a parenteral preparation.

In practicing the invention, the compound represented by the above Formula (I) may be administered simultaneously with other antitumor agent. Also, the compound represented by the above Formula (I) may be administered first and subsequently the other antitumor agent may be administered, or alternatively the other antitumor agent may be administered first and subsequently the compound represented by the above Formula (I) may be administered. Further, the compound represented by the above Formula (I) may be administered and then the other antitumor agent may be administered separately at time interval, or alternatively the other antitumor agent may be administered and then the compound represented by the above Formula (I) may be administered separately at time interval. The administration order and administration interval can be appropriately selected by those skilled in the art, depending on the used preparation including the compound represented by the above Formula (I), preparation including an antitumor agent which can be used in combination, the type of cancer cells to be treated, and the patient's condition.

The term "simultaneously" as used in the present specification means administering almost at the same time for a treatment. The term "separately" means administering separately at different time for a treatment, and for example, it refers to the case where one medication is used on the first day and another medication is used on the following day for a treatment. The term "sequentially" means administering in the order, and for example, it refers to the case where one medication is used first, and then, the other medication is used after an interval of predetermined time for a treatment.

The term "antitumor alkylating agents" as used in the present specification means an alkylating agent having antitumor activity, and the "alkylating agent" here in general refers to the agent providing an alkyl group in an alkylation reaction of an organic compound in which the hydrogen atom is substituted with an alkyl group. Examples of the "antitumor alkylating agents" include nitrogen mustard N-oxide, cyclophosphamide, ifosfamide, melphalan, busulfan, mitobronitol, carboquone, thiotepa, ranimustine, nimustine, temozolomide, carmustine, and the like.

The term "antitumor antimetabolites" as used in the present specification refers to a metabolic antagonist having antitumor activity, and the "metabolic antagonist" here in the wide sense includes substances which interfere a normal metabolic change to take place due to its similar structure or function to metabolites (vitamins, coenzymes, amino acids, sugars, etc.) that are the important factors in organisms, and substances which prevent the production of high-energy intermediates by inhibiting an electron transport system. Examples of the "antitumor antimetabolites" include methotrexate, 6-mercaptopurine riboside, mercaptopurine, 5-fluorouracil, tegafur, doxifluridine, carmofur, cytarabine, cytarabine ocphosphate, enocitabine, S-1, gemcitabine, fludarabine, pemetrexed disodium, and the like.

The term "antitumor antibiotics" as used in the present specification refers to an antibiotic having antitumor activity, and the "antibiotics" here is prepared by microorganisms, and includes substances that inhibit the growth or other functions of cells in microorganisms or other organisms. Examples of the "antitumor antibiotics" include actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, valrubicin, and the like.

The term "plant-derived antitumor agents" as used in the present specification includes compounds having antitumor activity, originated in plants, and those compounds which are subject to a chemical modification. Examples of the "plant-derived antitumor agents" include vincristine, vinblastine, vindesine, etoposide, sobuzoxane, docetaxel, paclitaxel, vinorelbine, and the like.

The term "antitumor camptothecin derivatives" as used in the present specification includes camptothecin per se, and refers to an inhibitory compound against proliferation of cancerous cells, which is structurally related to camptothecin. The "antitumor camptothecin derivatives" is not particularly limited to, but may be exemplified by, camptothecin, 10-hydroxy camptothecin, topotecan, irinotecan, 9-aminocamptothecin, or the like. The irinotecan is metabolized in vivo and exhibits antitumor activity as SN-38. The camptothecin derivative is thought to have almost similar mechanism of action and activity to camptothecin (Nitta et al, cancer and chemotherapeutics, 14, 850-857 (1987), etc.).

The term "antitumor platinum complex compounds" as used in the present specification refers to a platinum complex compound having antitumor activity, and the "platinum complex compound" here means a platinum complex compound that provides platinum in the form of ion. Preferred examples of the platinum compound include cisplatin; cis-diammine diaquo platinum(II)-ion; chloro(diethylenetriamine)-platinum(II) chloride; dichloro(ethylenediamine)-platinum(II); diammine(1,1-cyclobutanedicarboxylato) platinum(II)(carboplatin); spiroplatin; iproplatin; diammine(2-ethylmalonato)platinum(II); ethylenediamine malonato platinum(II); aqua(1,2-diamino dicyclohexane)sulphato platinum(II); aqua(1,2-diamino dicyclohexane)malonato platinum(u); (1,2-diaminocyclohexane) malonato platinum(II); (4-carboxyphthalate)(1,2-diaminocyclohexane)platinum(II); (1,2-diaminocyclohexane)-(isocitrate)platinum(II); (1,2-diaminocyclohexane)oxalato platinum(II); ormaplatin; tetraplatin; carboplatin; nedaplatin; and oxaliplatin. In addition, other antitumor platinum complex compounds exemplified in the present specification are generally known and are commercially available, and/or can be from those having ordinary skill in the art in accordance with conventional techniques.

The term "antitumor tyrosine kinase inhibitors" as used in the present specification refers to a tyrosine kinase inhibitor having antitumor activity, and the "tyrosine kinase inhibitor" here refers to a chemical substance for inhibiting a "tyrosine kinase" which involves in transferring a γ-phosphate group of ATP to a hydroxyl group of a specific tyrosine in proteins. Examples of the "antitumor tyrosine kinase inhibitors" include gefitinib, imatinib, erlotinib, and the like.

The term "monoclonal antibodies" as used in the present specification refers to an antibody produced from monoclonal antibody-forming cells, and examples include cetuximab, bevacizumab, rituximab, alemtuzumab, trastuzumab, and the like.

The term "interferons" as used in the present specification refers to an interferon having antitumor activity, and generally in the case of viral infection, is a glycoprotein having the molecular weight of about 20,000 which is produced/secreted from the most of animal cells. As well as inhibiting viral proliferation, the interferon inhibits proliferation of cells (tumor cells in particular) and exhibits various immunity effector activities including the enhancement of natural killer activity; and it is known as one of cytokines. Examples of the "interferon" include interferon α, interferon α-2a, interferon α-2b, interferon β, interferon γ-1a, interferon γ-nl, and the like.

The term "biological response modifiers" as used in the present specification is also abbreviated as BRM, and generally is a generic term of substances or drugs which lead to achieve individual benefits against tumors, infections, or other diseases by regulating biological reactions such as a defense mechanism possessed by organisms, and survival, proliferation, or differentiation of tissue cells. Examples of the "biological response modifiers" include krestin, lentinan, schizophyllan, picibanil, ubenimex, and the like.

The term "other antitumor agents" as used in the present specification refers to an antitumor agent having antitumor activity which is not included in any of the above. Examples of the "other antitumor agents" include mitoxantrone, L-asparaginase, procarbazine, dacarbazine, hydroxycarbamide, pentostatin, tretinoin, alefacept, darbepoetin alfa, anastrozole, exemstane, bicalutamide, leuproreline, flutamide, fulvestrant, pegaptanib octasodium, denileukin diftitox, aldesleukin, thyrotropin alfa, arsenic trioxide, bortezomib, capecitabine, goserelin, and the like.

All of the above "antitumor alkylating agents", "antitumor antimetabolites", "antitumor antibiotics", "plant-derived antitumor agents", "antitumor platinum complex compounds", "antitumor camptothecin derivatives", "antitumor tyrosine kinase inhibitors", "monoclonal antibodies", "interferons", "biological response modifiers", and "other antitumor agents" are generally known and commercially available, or can be from those having ordinary skill in the art in accordance with methods known per se or commonly known/used methods. There is disclosed a process for producing gefitinib, for example, in the specification of U.S. Pat. No. 5,770,599; a process for producing cetuximab, for example, in International Publication WO96/40210; a process for producing bevacizumab, for example, in International Publication WO94/10202; a process for producing oxaliplatin, for example, in the specifications of U.S. Pat. Nos. 5,420,319 and 5,959,133; a process for producing gemcitabine, for example, in the specifications of U.S. Pat. Nos. 5,434,254 and 5,223,608; a process for producing camptothecin in the specifications of U.S. Pat. Nos. 5,162,532, 5,247,089, 5,191,082, 5,200,524, 5,243,050, and 5,321,140; a process for producing irinotecan, for example, in the specification of U.S. Pat. No. 4,604,463; a process for producing topotecan, for example, in the specification of U.S. Pat. No. 5,734,056; a process for producing temozolomide, for example, in the specification of Japanese Unexamined Patent Publication No. H4-5029; and a process for producing rituximab in the specification of Japanese Unexamined Patent Publication No. H2-503143.

For the antitumor alkylating agents, for example, nitrogen mustard N-oxide is commercially available under the product name Nitromin from Mitsubishi Pharma Corporation; cyclophosphamide is commercially available under the product name Endoxan from Shionogi & Co., Ltd.; ifosfamide is commercially available under the product name ifomide from Shionogi & Co., Ltd.; melphalan is commercially available under the product name Alkeran from GlaxoSmithKline; busulfan is commercially available under the product name Mablin from Takeda pharmaceutical; mitobronitol is commercially available under the product name Myebrol from Kyorin Pharmaceutical Co., Ltd; carboquone is commercially available under the product name Esquinon from Sankyo Co., Ltd; thiotepa is commercially available under the product name Tespamin from Sumitomo Pharmaceuticals Co., Ltd; ranimustine is commercially available under the product name Cymerin from Mitsubishi Pharma Corporation; nimustine is commercially available under the product name Nidran from Sankyo Co., Ltd.; temozolomide is commercially available under the product name Temodal from Schering-Plough Co., Ltd.; and carmustine is commercially available under the product name Gliadel wafer from Guilford Pharmaceuticals.

For the antitumor antimetabolites, for example, methotrexate is commercially available under the product name Methotrexate from Takeda pharmaceutical; 6-mercaptopurine riboside is commercially available under the product name Thioinosine from Aventis Co., Ltd.; mercaptopurine is commercially available under the product name Leukerin from Takeda pharmaceutical; 5-fluorouracil is commercially available under the product name 5-FU from Kyowa Hakko Co., Ltd.; tegafur is commercially available under the product name Futraful from Taiho Pharmaceutical Co., Ltd; doxifluridine is commercially available under the product name Furtulon from Roche Japan; carmofur is commercially available under the product name Yamafur from Yamanouchi Pharmaceutical; cytarabine is commercially available under the product name Cylocide from Nippon Shinyaku Co., Ltd.; cytarabine ocfosfate is commercially available under the product name Starasid from Nippon Kayaku Co., Ltd.; enocitabine is commercially available under the product name Sunrabin from Asahi Kasei Corporation; S-1 is commercially available under the product name TS-1 from Taiho Pharmaceutical Col, Ltd; gemcitabine is commercially available under the product name Gemzar from Eli Lily Co., Ltd.; fludarabine is commercially available under the product name Fludara from Japan Schering-Plough K.K.; and pemetrexed disodium is commercially available under the product name Alimta from Eli Lily Co., Ltd.

For the antitumor antibiotics, for example, actinomycin D is commercially available under the product name Cosmegen from Banyu Pharmaceutical Co., Ltd; doxorubicin is commercially available under the product name Adriacin from Kyowa Hakko Co., Ltd.; daunorubicin is commercially available under the product name Daunomycin from Meiji Seika, Ltd.; neocarzinostatin is commercially available under the product name Neocarzinostatin from Yamanouchi Pharmaceutical; bleomycin is commercially available under the product name Bleo from Nippon Kayaku Co., Ltd.; peplomycin is commercially available under the product name Peplo from Nippon Kayaku Co., Ltd.; mitomycin C is commercially available under the product name Mitomycin from Kyowa Hakko Co., Ltd.; aclarubicin is commercially available under the product name Aclacinon from Yamanouchi Pharmaceutical; pirarubicin is commercially available under the product name Pinorubin from Nippon Kayaku Co., Ltd.; epirubicin is commercially available under the product name Farmorubicin from Pharmacia corporation; zinostatin stimalamer is commercially available under the product name Smancs from Yamanouchi Pharmaceutical; idarubicin is commercially available under the product name Idamycin from Pharmacia corporation; sirolimus is commercially available under the product name Rapamune from Wyeth; and valrubucin is commercially available under the product name Valstar from Anthra pharmaceutical.

For the plant-derived antitumor agents, for example, vincristine is commercially available under the product name Oncovin from Shionogi & Co., Ltd.; vinblastin is commercially available under the product name Vinblastin from Kyorin Pharmaceutical Co., Ltd; vindesine is commercially available under the product name Fildesin from Shionogi & Co., Ltd.; etoposide is commercially available under the product name Lastet from Nippon Kayaku Co., Ltd.; sobzoxan is commercially available under the product name Perazolin from Zenyaku Kogyo; docetaxel is commercially available under the product name Taxotere from Aventis Co., Ltd.; paclitaxel is commercially available under the product name Taxol from Bristol-Myers K.K.; and vinorelbine is commercially available under the product name Navelbine from Kyowa Hakko Co., Ltd.

For the antitumor platinum complex compounds, for example, cisplatin is commercially available under the product name Randa from Nippon Kayaku Co., Ltd.; carboplatin is commercially available under the product name Paraplatin from Bristol-Myers K.K.; nedaplatin is commercially available under the product name Aqupla from Shionogi & Co., Ltd.; and oxaliplatin is commercially available under the product name Eloxatin from Sanofi K.K.

For the antitumor camptothecin derivatives, for example, irinotecan is commercially available under the product name Campto from Yakult Co., Ltd.; topotecan is commercially available under the product name Hycamtin from GlaxoSmithKline; and camptothecin is commercially available from Aldrich Chemical Company, U.S.A., etc.

For the antitumor tyrosine kinase inhibitors, for example, gefitinib is commercially available under the product name Iressa from AstraZeneca; imatinib is commercially available under the product name Gleevec from Novartis pharma K.K; and erlotinib is commercially available under the product name Tarceva from OSI pharmaceutical, Inc.

For the monoclonal antibodies, for example, cetuximab is commercially available under the product name Erbitux from Bristol-Myers Squibb Company; bevacizumab is commercially available under the product name Avastin from Genentech Inc.; rituximab is commercially available under the product name Rituxan from Biogen Idec Inc.; alemtuzumab is commercially available under the product name Campath from Berlex, Inc.; and trastuzumab is commercially available under the product name Herceptin from Chugai Pharmaceutical Co., Ltd.

For the interferons, for example, interferon α is commercially available under the product name Sumiferon from Sumitomo Pharma Co., Ltd.; interferon α-2a is commercially available under the product name Canferon-A from Takeda pharmaceutical; interferon α-2b is commercially available under the product name Intron A from Schering-Plough Co., Ltd.; interferon β is commercially available under the product name IFN β from Mochida Pharmaceutical Co., Ltd.; interferon γ-1a is commercially available under the product name Immunomax-γ from Shionogi & Co., Ltd.; and interferon γ-nl is commercially available under the product name Ogamma from Otsuka Pharmaceutical Co., Ltd.

For the biological response modifiers, for example, krestin is commercially available under the product name Krestin from Sankyo Co., Ltd.; lentinan is commercially available under the product name Lentinan from Aventis Co., Ltd.; schizophyllan is commercially available under the product name Sonifilan from Kaken Pharmaceutical Co., Ltd.; picibanil is commercially available under the product name Picibanil from Chugai Pharmaceutical Co., Ltd.; and ubenimex is commercially available under the product name Bestatin from Nippon Kayaku Co., Ltd.

For the other antitumor agents, for example, mitoxantrone is commercially available under the product name Novantron from Wyeth-Lederie Japan; L-asparaginase is commercially available under the product name Leunase from Kyowa Hakko Co., Ltd.; procarbazine is commercially available under the product name Natulan from Roche Japan; dacarbazine is commercially available under the product name Dacarbazine from Kyowa Hakko Co., Ltd.; hydroxycarbamide is commercially available under the product name Hydrea from Bristol K.K.; pentostatin is commercially available under the product name Coforin from Chemo-Sero-Therapeutic Research Institute; tretinoin is commercially available under the product name Vesanoid from Roche Japan; alefacept is commercially available under the product name Amevive from Biogen Idec Inc.; darbepoetin alfa is commercially available under the product name Aranesp from Amgen Inc.; anastrozole is commercially available under the product name Arimidex from AstraZeneca; exemestane is commercially available under the product name Aromasin from Pfizer Inc.; bicalutamide is commercially available under the product name Casodex from AstraZeneca; leuproreline is commercially available under the product name Lupulin from Takeda pharmaceutical; flutamide is commercially available under the product name Eulexin from Schering-Plough Co., Ltd.; fulvestrant is commercially available under the product name Faslodex from AstraZeneca; pegaptanib octasodium is commercially available under the product name Macugen from Guilead Sciences Inc.; denileukin diftitox is commercially available under the product name Ontak from Ligand Pharmaceuticals Inc.; aldesleukin is commercially available under the product name Proleukin from Chiron Corporation; Thyrotropin alpha is commercially available under the product name Thyrogen from Genzyme; Arsenic trioxide is commercially available under the product name Trisenox from Cell Therapeutics, Inc.; bortezomib is produced under the product name Velcade from Millenium; capecitabine is produced under the product name Xeloda from Roche; and goserelin is produced under the product name Zoladex from AstraZeneca.

The term "antitumor agents" as used in the present specification include antitumor agents selected from "antitumor alkylating agents", "antitumor antimetabolites", "antitumor antibiotics", "plant-derived antitumor agents", "antitumor platinum complex compounds", "antitumor camptothecin derivatives", "antitumor tyrosine kinase inhibitors", "monoclonal antibodies", "interferons", "biological response modifiers", and "other antitumor agents".

Embodiments of the compound represented by the above Formula (I) will be described in more detail.

$R_1$ and $R_2$, which may be the same or different, are each a hydrogen atom; a substituent selected from the group consisting of a halogen atom, a hydroxy group, a nitro group, a cyano group, an amino group, a carbamoyl group, an aminosulfonyl group, an imino group, a lower alkylamino group, a di-lower alkylamino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, and a carboxyl group, (hereinafter, referred to as <Substituent Group α>); a lower alkyl group which may be substituted with one or more substituents selected from <Substituent Group α>; or a cycloalkyl group having 3 to 6 carbon atoms, which may be substituted.

$R_1$ is preferably a substituent selected from <Substituent Group α>; a lower alkyl group which may be substituted with one or more substituents selected from <Substituent Group α>; or a cyclopropyl group, where the <Substituent Group α> is a halogen atom.

$R_1$ is more preferably a lower alkyl group having 1 to 2 carbon atom(s) which may be substituted with 1 to 3 fluorine atom(s); a cyclopropyl group; or a chlorine atom.

$R_1$ is further preferably a methyl group, an ethyl group, a difluoromethyl group, a trifluoromethyl group, a cyclopropyl group, or a chlorine atom.

$R_1$ is even further preferably an ethyl group, a difluoromethyl group, a trifluoromethyl group, a cyclopropyl group, or a chloride atom.

$R_2$ is preferably a hydrogen atom.

$R_3$ and $R_4$, which may be the same or different, are each:
a) a hydrogen atom;
b) a lower alkyl group substituted with $NR_aR_b$, where $R_a$ and $R_b$, which may be the same or different, are each a hydrogen atom, a lower alkyl group which may be substituted, a benzyl group which may be substituted, or a cycloalkyl group which may be substituted;
c) a substituent selected from the group consisting of a halogen atom, a hydroxy group, a nitro group, a cyano group, an amino group, a carbamoyl group, an aminosulfonyl group, an imino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, a carboxyl group, and a benzyl group (hereinafter, referred to as <Substituent Group β>);
d) a lower alkyl group which may be substituted with one or more substituents selected from the <Substituent Group β>;
e) a lower alkenyl group which may be substituted with one or more substituents selected from the <Substituent Group β>;
f) a phenyl group;
g) a lower alkyl group substituted with a phenyl group;
h) a 4- to 7-membered aliphatic heterocyclic group;
i) a lower alkyl group substituted with a 4- to 7-membered aliphatic heterocyclic group;
j) a 5- or 6-membered aromatic heterocyclic group; or
k) a lower alkyl group substituted with a 5- or 6-membered aromatic heterocyclic group,
wherein the phenyl group, the aliphatic heterocyclic group, and the aromatic heterocyclic group each independently may be substituted with one or more substituents, which may be the same or different, selected from the following 1) to 4):
1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group >, and the aliphatic heterocyclic group may include an unsaturated bond, and the lower alkyl group as defined in the b), g), i), and k) above may be suitably substituted,
or alternatively, $R_3$ and $R_4$ are taken together to form a 4- to 7-membered aliphatic heterocyclic group,
wherein the aliphatic heterocyclic group may be substituted with one or more substituents, which may be the same or different, selected from the following 1) to 4):
1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group β>,
and the aliphatic heterocyclic group may include an unsaturated bond.

$R_3$ and $R_4$ preferably, which may be the same or different, are each:
a) a hydrogen atom;
b) a lower alkyl group substituted with $NR_aR_b$, where $R_a$ and $R_b$, which may be the same or different, are each a hydrogen atom, a lower alkyl group, a benzyl group, or a cycloalkyl group, wherein the benzyl group and the cycloalkyl group each independently may be substituted with one or more substituents, which may be the same or different, selected from the following 1) to 3):
1) a lower alkyl group;
2) a substituent selected from <Substituent Group β>; and
3) a lower alkyl group substituted with one or more substituents selected from <Substituent Group β>; and the cycloalkyl group may include an unsaturated bond;
c) a substituent selected from the <Substituent Group β>;
d) a lower alkyl group which may be substituted with one or more substituents selected from the <Substituent Group β>;
e) a lower alkenyl group which may be substituted with one or more substituents selected from the <Substituent Group β>;
f) a phenyl group;
g) a lower alkyl group substituted with a phenyl group;
h) a 4- to 6-membered aliphatic heterocyclic group selected from an azetidinyl group, a pyrrolidinyl group, a piperidinyl group, and a piperazinyl group;
i) a lower alkyl group substituted with a 4- to 6-membered aliphatic heterocyclic group selected from an azetidinyl group, a pyrrolidinyl group, a piperidinyl group, and a piperazinyl group;
j) a 5- or 6-membered aromatic heterocyclic group selected from a pyrrolyl group, an imidazolyl group, a pyrazolyl group, a pyridyl group, a pyrazinyl group, and a pyrimidinyl group; or
k) a lower alkyl group substituted with a 5- or 6-membered aromatic heterocyclic group selected from a pyrrolyl group, an imidazolyl group, a pyrazolyl group, a pyridyl group, a pyrazinyl group, and a pyrimidinyl group, wherein the phenyl group, the aliphatic heterocyclic group, and the aromatic heterocyclic group each independently may be substituted with one or more substituents, which may be the same or different, selected from the following 1) to 4):
1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group β>,
and the aliphatic heterocyclic group may include an unsaturated bond,
or alternatively, $R_3$ and $R_4$ are taken together to form a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituents, which may be the same or different, selected from the following 1) to 4):

1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group β>, and the aliphatic heterocyclic group may include an unsaturated bond.

For $R_3$ and $R_1$, it is more preferable that one of $R_3$ and $R_4$ is a hydrogen atom, and the other one of $R_3$ and $R_4$ is:

a) a lower alkyl group substituted with $NR_aR_b$, where $R_a$ and $R_b$, which may be the same or different, are each a hydrogen atom, a lower alkyl group, a benzyl group, or a cycloalkyl group having three to six carbon atoms, wherein the cycloalkyl group may be substituted with one or more substituents, which may be the same or different, selected from the following 1) to 3):

1) a lower alkyl group;
2) a substituent selected from <Substituent Group β>; and
3) a lower alkyl group substituted with one or more substituents selected from <Substituent Group β>; and the cycloalkyl group may include an unsaturated bond;

b) a 4- to 6-membered aliphatic heterocyclic group selected from an azetidinyl group, a pyrrolidinyl group, a piperidinyl group, and a piperazinyl group; or c) a lower alkyl group substituted with a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituents, which may be the same or different, selected from the following 1) to 4):

1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group β>.

For $R_3$ and $R_4$, it is even more preferable that one of $R_3$ and $R_4$ is a hydrogen atom, and the other one of $R_3$ and $R_4$ is:

a) a lower alkyl group substituted with $NR_aR_b$, where $R_a$ and $R_b$, which may be the same or different, are each a hydrogen atom a lower alkyl group, or a cycloalkyl group having five to six carbon atoms, wherein the cycloalkyl group may be substituted with one or more substituents, which may be the same or different, selected from the following 1) to 3):

1) a lower alkyl group;
2) a substituent selected from <Substituent Group β>; and
3) a lower alkyl group substituted with one or more substituents selected from <Substituent Group β>; or b) a 4- or 6-membered aliphatic heterocyclic group selected from an azetidinyl group, a pyrrolidinyl group and a piperidinyl group, wherein the aliphatic heterocyclic group may be substituted with one or more substituents, which may be the same or different, selected from the following 1) to 3):

1) a lower alkyl group;
2) a substituent selected from the <Substituent Group β>; and
3) a lower alkyl group substituted with one or more substituents selected from the <Substituent Group β>.

The <Substituent Group β> for $R_3$ and $R_4$ is preferably a group consisting of a halogen atom, a hydroxy group, an amino group, a lower alkylsulfonyl group, and a lower alkoxy group.

For $R_3$ and $R_4$, it is particularly preferable that one of $R_3$ and $R_4$ is a hydrogen atom, and the other one of $R_3$ and $R_4$ is an amino lower alkyl group (wherein said lower alkyl is a linear or branched alkyl group having 1 to 3 carbon atom(s)) which is N-substituted or N, N-di-substituted with a linear or branched alkyl group having 1 to 5 carbon atom(s); a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cycloalkyl group having five to six carbon atoms, wherein the piperidinyl group, the pyrrolidinyl group, and the azetidinyl group each independently may be further substituted with a linear or branched alkyl group having 1 to 3 carbon atom(s), and the cycloalkyl group may be substituted with a linear or branched alkyl group having 1 to 3 carbon atom(s) optionally having a hydroxy group. Here, the piperidinyl group is preferably N-substituted piperidin-3-yl, N-substituted piperidin-4-yl, or the like. The pyrrolidinyl group is preferably N-substituted pyrrolidin-2-yl, N-substituted pyrrolidin-3-yl, or the like, and more preferably N-substituted pyrrolidin-2-yl. The azetidinyl group is preferably N-substituted azetidin-3-yl, or the like. The cycloalkyl group is preferably cyclopentyl, cyclohexyl, or the like, more preferably cyclopentyl.

For $R_3$ and $R_4$, it is even more particularly preferable that one of $R_3$ and 4 is a hydrogen atom, and the other one of $R_3$ and $R_4$ is a linear or branched alkyl group having 1 to 3 carbon atom(s) which is substituted with a dimethylamino group, an isopropylamino group, 1,1-dimethylpropylamino group, or t-butylamino group; a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cyclopentyl group which may be substituted with a methyl group or a hydroxymethyl group, wherein the piperidinyl group, the pyrrolidinyl group, and the azetidinyl group may be further substituted with a linear or branched alkyl group having 1 to 3 carbon atom(s).

$R_5$ is a hydrogen atom, a cyano group, a halogen atom, or a lower alkyl group.

$R_5$ is preferably a hydrogen atom, a cyano group, a halogen atom, or a methyl group, more preferably a cyano group, a halogen atom, or a methyl group, particularly preferably a cyano group, a fluorine atom, or a methyl group.

For $R_1$ to $R_5$, from the viewpoint of exhibiting a cell proliferation inhibitory effect on the basis of a PLK1 inhibitory effect, the following case (A) is preferable, the following case (B) is more preferable, and the following case (C) is even more preferable.

(A) Case where:

$R_1$ is a lower alkyl group having 1 or 2 carbon atom(s) which may be substituted with 1 to 3 fluorine atom(s); a cyclopropyl group; or a halogen atom;

$R_2$ is a hydrogen atom;

one of $R_3$ and $R_4$ is a hydrogen atom, while the other one of $R_3$ and $R_4$ is an amino lower alkyl group (wherein said lower alkyl is a linear or branched alkyl group having 1 to 3 carbon atom(s)) which is N-substituted or N,N-di-substituted with a linear or branched alkyl group having 1 to 5 carbon atom(s);

a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cycloalkyl group having five to six carbon atoms, wherein the piperidinyl group, the pyrrolidinyl group, and the azetidinyl group each independently may be further substituted with a linear or branched alkyl group having 1 to 3 carbon atom(s), and the cycloalkyl group may be substituted with a linear or branched alkyl group having 1 to 3 carbon atom(s) optionally having a hydroxy group; and $R_5$ is a cyano group, a halogen atom, or a methyl group.

(B) Case where:

$R_1$ is a methyl group, an ethyl group, a difluoromethyl group, a trifluoromethyl group, a cyclopropyl group, or a chlorine atom;

$R_2$ is a hydrogen atom;

one of $R_3$ and $R_4$ is a hydrogen atom, while the other one of $R_3$ and $R_4$ is a linear or branched alkyl group having 1 to 3 carbon atom(s) which is substituted with a dimethylamino group, an isopropylamino group, 1,1-dimethylpropylamino group, or t-butylamino group; a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cyclopentyl group which may be substituted with a methyl group or a hydroxymethyl group, wherein the piperidinyl group, the pyrrolidinyl group, and the azetidinyl group each independently may be further substituted with a linear or branched alkyl group having 1 to 3 carbon atom(s); and $R_5$ is a cyano group, a fluorine atom, or a methyl group.

(C) Case where:

$R_1$ is an ethyl group, a difluoromethyl group, a trifluoromethyl group, a cyclopropyl group, or a chlorine atom;

$R_2$ is a hydrogen atom;

one of $R_3$ and $R_4$ is a hydrogen atom, while the other one of $R_3$ and $R_4$ is a t-butylaminomethyl group; 1-methyl-dimethylaminoethyl group; a piperidin-3-yl group which is N-substituted with a linear or branched alkyl group having 1 to 5 carbon atom(s); a piperidin-4-yl group which is N-substituted with a linear or branched alkyl group having 1 to 5 carbon atom(s); a pyrrolidin-2-yl group which is N-substituted with a linear or branched alkyl group having 1 to 5 carbon atom(s); an azetidin-3-yl group which is N-substituted with a linear or branched alkyl group having 1 to 5 carbon atom(s); or a cyclopentyl group which may be substituted with a methyl group or a hydroxymethyl group, wherein the piperidin-3-yl group, the piperidin-4-yl group, the pyrrolidin-2-yl group, and the azetidin-3-yl group may be further substituted with a methyl group; and $R_5$ is a cyano group, or a fluorine atom.

The <Substituent Group α> is a group consisting of a halogen atom, a hydroxy group, a nitro group, a cyano group, an amino group, a carbamoyl group, an aminosulfonyl group, an imino group, a lower alkylamino group, a di-lower alkylamino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, and a carboxyl group.

The <Substituent Group α> is preferably a halogen atom, and more preferably a chlorine atom.

The <Substituent Group β> is a group consisting of a halogen atom, a hydroxy group, a nitro group, a cyano group, an amino group, a carbamoyl group, an aminosulfonyl group, an imino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, a carboxyl group, and a benzyl group.

The <Substituent Group β> is preferably a group consisting of a halogen atom, a hydroxy group, an amino group, a lower alkylsulfonyl group, and a lower alkoxy group.

In relation with the arrowed asymmetric carbon atom in the following substructure, the compound represented by the Formula (I) is preferably an S-form.

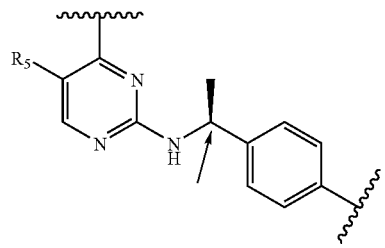

The compound of above Formula (I) is preferably (a)  2-[((1S)-1-{4-[2-(tert-butylamino)-1-hydroxyethyl]phenyl}ethyl)amino]-4-(8-ethylimidazo[1,2-a]pyridin-3-yl)pyrimidine-5-carbonitrile (Examples 5 and 6);

(b)  (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol (Example 11);

(c)  2-[((1S)-1-{4-[hydroxy(pyridin-2-yl)methyl]phenyl}ethyl)amino]-4-(8-methylimidazo[1,2-a]pyridin-3-yl)pyrimidine-5-carbonitrile (Example 12);

(d)  4-(8-ethylimidazo[1,2-a]pyridin-3-yl)-2-({(1S)-1-[4-(4-hydroxy-1-methylpiperidin-4-yl) phenyl]ethyl}amino)pyrimidine-5-carbonitrile (Example 20);

(e)  4-(8-ethylimidazo[1,2-a]pyridin-3-yl)-2-[((1S)-1-{4-[hydroxy(1-isopropylpiperidin-4-yl) methyl]phenyl}ethyl)amino]pyrimidine-5-carbonitrile (Examples 26 and 27);

(f)  4-(8-cyclopropylimidazo[1,2-a]pyridin-3-yl)-2-[((1S)-1-{4-[hydroxy(1-methylpiperidin-4-yl) methyl]phenyl}ethyl)amino]pyrimidine-5-carbonitrile (Example 36);

(g)  4-(8-chloroimidazo[1,2-a]pyridin-3-yl)-2-[((1S)-1-{4-[(1-cyclopropylpiperidin-4-yl) (hydroxy)methyl]phenyl}ethyl)amino]pyrimidine-5-carbonitrile (Example 37);

(h)  4-(8-ethylimidazo[1,2-a]pyridin-3-yl)-2-[((1S)-1-{4-[hydroxy(1-methylpiperidin-3-yl) methyl]phenyl}ethyl)amino]pyrimidine-5-carbonitrile (Examples 41, 42, 43, and 44);

(i)  2-{[(1S)-1-(4-{hydroxy[1-methylpyrrolidin-2-yl]methyl}phenyl)ethyl]amino}-4-(8-methylimidazo[1,2-a]pyridin-3-yl)pyrimidine-5-carbonitrile (Examples 50, 51, 52, and 53);

(j)  2-[((1S)-1-{4-[2-(tert-butylamino)-1-hydroxyethyl]phenyl}ethyl)amino]-4-(8-chloroimidazo[1,2-a]pyridin-3-yl)pyrimidine-5-carbonitrile (Examples 9 and 61);

(k)  2-[((1S)-1-{4-[2-(tert-butylamino)-1-hydroxyethyl]phenyl}ethyl)amino]-4-[8-(difluoromethyl) imidazo[1,2-a]pyridin-3-yl]pyrimidine-5-carbonitrile (Examples 10 and 60);

(l) 4-(8-cyclopropylimidazo[1,2-a]pyridin-3-yl)-2-[((1S)-1-{4-[(1,2-dimethylpyrrolidin-2-yl) (hydroxy)methyl]phenyl}ethyl)amino]pyrimidine-5-carbonitrile (Examples 63, 64, 65, and 66);

(m) (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol (Example 67);

(n) (1S)-1-[4-((1S)-1-{[4-(8-chloroimidazo[1,2-a]pyridin-3-yl)-5-fluoropyrimidin-2-yl]amino}ethyl)phenyl]-2-[(1,1-dimethylpropyl)amino]ethanol (Example 68);

(o) (1S)-1-[4-((1S)-1-{[4-(8-chloroimidazo[1,2-a]pyridin-3-yl)-5-fluoropyrimidin-2-yl]amino}ethyl)phenyl]-2-[(1-methylcyclopentyl)amino]ethanol (Example 71);

(p) (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol (Example 73);

(q) (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol (Example 74);

(r) (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol (Example 79);

(s) (1S)-2-(tert-butylamino)-1-{4-[(1S)-1-({5-fluoro-4-[8-(trifluoromethyl)imidazo[1,2-a]pyridin-3-yl]pyrimidin-2-yl} amino)ethyl]phenyl}ethanol (Example 81);

(t) [4-((1S)-1-{[4-(8-chloroimidazo[1,2-a]pyridin-3-yl)-5-fluoropyrimidin-2-yl]amino}ethyl)phenyl](1,2-dimethylpyrrolidin-2-yl)methanol (Examples 82 and 83);

(u) 1-[4-((1S)-1-{[4-(8-chloroimidazo[1,2-a]pyridin-3-yl)-5-fluoropyrimidin-2-yl]amino}ethyl) phenyl]-2-(dimethylamino)-2-methylpropan-1-ol (Examples 84 and 85);

(v) [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol (Examples 88 and 89);

(w) [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol (Examples 90 and 91);

(x) (1S)-2-(tert-butylamino)-1-{4-[(1S)-1-({4-[8-(difluoromethyl)imidazo[1,2-a]pyridin-3-yl]-5-fluoropyrimidin-2-yl} amino)ethyl]phenyl}ethanol (Example 93), or a pharmaceutically acceptable salt or ester thereof.

In addition, the preferred aspects of the present invention can also be represented as follows.

(1) A compound of above Formula (I) or a pharmaceutically acceptable salt or ester thereof, in which $R_1$ is a substituent selected from the <Substituent Group α>; a lower alkyl group which may be substituted with one or more substituents selected from the <Substituent Group α>; or a cyclopropyl group, where the <Substituent Group α> is a halogen atom; and $R_2$ is a hydrogen atom; or (2) The compound of (1) above or a pharmaceutically acceptable salt or ester thereof, in which $R_3$ and $R_4$, which may be the same or different, are each:

a) a hydrogen atom;

b) a lower alkyl group substituted with $NR_aR_b$, where $R_a$ and $R_b$, which may be the same or different, are each a hydrogen atom, a lower alkyl group, a benzyl group, or a cycloalkyl group, wherein the benzyl group and the cycloalkyl group each independently may be substituted with one or more substituents, which may be the same or different, selected from the following 1) to 3):

1) a lower alkyl group;
   2) a substituent selected from <Substituent Group β>; and
   3) a lower alkyl group substituted with one or more substituents selected from <Substituent Group β>; and the cycloalkyl group may include an unsaturated bond;

c) a substituent selected from the <Substituent Group β>;

d) a lower alkyl group which may be substituted with one or more substituents selected from the <Substituent Group β>;

e) a lower alkenyl group which may be substituted with one or more substituents selected from the <Substituent Group β>;

f) a phenyl group;

g) a lower alkyl group substituted with a phenyl group;

h) a 4- to 6-membered aliphatic heterocyclic group selected from an azetidinyl group, a pyrrolidinyl group, a piperidinyl group, and a piperazinyl group;

i) a lower alkyl group substituted with a 4- to 6-membered aliphatic heterocyclic group selected from an azetidinyl group, a pyrrolidinyl group, a piperidinyl group, and a piperazinyl group;

j) a 5- or 6-membered aromatic heterocyclic group selected from a pyrrolyl group, an imidazolyl group, a pyrazolyl group, a pyridyl group, a pyrazinyl group, and a pyrimidinyl group; or k) a lower alkyl group substituted with a 5- or 6-membered aromatic heterocyclic group selected from a pyrrolyl group, an imidazolyl group, a pyrazolyl group, a pyridyl group, a pyrazinyl group, and a pyrimidinyl group, wherein the phenyl group, the aliphatic heterocyclic group, and the aromatic heterocyclic group each independently may be substituted with one or more substituents, which may be the same or different, selected from the following 1) to 4):

1) a lower alkyl group;
   2) a substituent selected from the <Substituent Group β>;
   3) a lower alkyl group substituted with one or more substituents selected from the <Substituent Group β>; and
   4) a cycloalkyl group having 3 to 6 carbon atoms, which may be substituted with one or more substituents selected from the <Substituent Group β>, and the aliphatic heterocyclic group may include an unsaturated bond, or alternatively, $R_3$ and $R_4$ are taken together to form a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituents, which may be the same or different, selected from the following 1) to 4):

1) a lower alkyl group;
   2) a substituent selected from the <Substituent Group β>;
   3) a lower alkyl group substituted with one or more substituents selected from the <Substituent Group β>; and
   4) a cycloalkyl group having 3 to 6 carbon atoms, which may be substituted with one or more substituents selected from the <Substituent Group 1>, and the aliphatic heterocyclic group may include an unsaturated bond; or (3) The compound described in (1) or (2) above or a pharmaceutically acceptable salt or ester thereof, in which $R_5$ is a hydrogen atom, a cyano group, a halogen atom, or a methyl group; or (4) The compound described in any one of (1) to (3) above or a pharmaceutically acceptable salt or ester thereof, in which one of $R_3$ and $R_4$ is a hydrogen atom, and the other one of $R_3$ and $R_4$ is:

a) a lower alkyl group substituted with $NR_aR_b$, where $R_a$ and $R_b$, which may be the same or different, are each a hydrogen atom, a lower alkyl group, a benzyl group, or a cycloalkyl group having three to six carbon atoms, wherein the cycloalkyl group may be substituted with one or more substituents, which may be the same or different, selected from the following 1) to 3):

1) a lower alkyl group;
2) a substituent selected from <Substituent Group β>; and
3) a lower alkyl group substituted with one or more substituents selected from <Substituent Group β>; and the cycloalkyl group may include an unsaturated bond;
b) a 4- to 6-membered aliphatic heterocyclic group selected from an azetidinyl group, a pyrrolidinyl group, a piperidinyl group, and a piperazinyl group; or
c) a lower alkyl group substituted with a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituents, which may be the same or different, selected from the following 1) to 4):
1) a lower alkyl group;
2) a substituent selected from the <Substituent Group β>;
3) a lower alkyl group substituted with one or more substituents selected from the <Substituent Group β>; and
4) a cycloalkyl group having 3 to 6 carbon atoms, which may be substituted with one or more substituents selected from the <Substituent Group β>; or
(5) The compound described in any one of (1) to (4) above or a pharmaceutically acceptable salt or ester thereof, in which $R_1$ is a lower alkyl group having one or two carbon atom(s), which may be substituted with 1 to 3 fluorine atom(s); a cyclopropyl group; or a chlorine atom; or
(6) The compound described in any one of (1) to (5) above or a pharmaceutically acceptable salt or ester thereof, in which the <Substituent Group β> is a halogen atom, a hydroxy group, an amino group, a lower alkylsulfonyl group, and a lower alkoxy group; or
(7) The compound described in any one of (1) to (6) above or a pharmaceutically acceptable salt or ester thereof, in which one of $R_3$ and $R_4$ is a hydrogen atom, and the other one of $R_3$ and $R_4$ is:
a) a lower alkyl group substituted with $NR_aR_b$, where $R_a$ and $R_b$, which may be the same or different, are each a hydrogen atom a lower alkyl group, or a cycloalkyl group having five to six carbon atoms, wherein the cycloalkyl group may be substituted with one or more substituents, which may be the same or different, selected from the following 1) to 3):
1) a lower alkyl group;
2) a substituent selected from <Substituent Group β>; and
3) a lower alkyl group substituted with one or more substituents selected from <Substituent Group β>; or
b) a 4- or 6-membered aliphatic heterocyclic group selected from an azetidinyl group, a pyrrolidinyl group and a piperidinyl group, wherein the aliphatic heterocyclic group may be substituted with one or more substituents, which may be the same or different, selected from the following 1) to 4):
1) a lower alkyl group;
2) a substituent selected from the <Substituent Group β>; and
3) a lower alkyl group substituted with one or more substituents selected from the <Substituent Group β>; or
(8) The compound described in any one of (1) to (7) above or a pharmaceutically acceptable salt or ester thereof, in which:
$R_1$ is a lower alkyl group having 1 or 2 carbon atom(s) which may be substituted with 1 to 3 fluorine atom(s); a cyclopropyl group; or a halogen atom;
$R_2$ is a hydrogen atom;
one of $R_3$ and $R_4$ is a hydrogen atom, while the other one of $R_3$ and $R_4$ is an amino lower alkyl group (wherein said lower alkyl is a linear or branched alkyl group having 1 to 3 carbon atom(s)) which is N-substituted or N,N-di-substituted with a linear or branched alkyl group having 1 to 5 carbon atom(s); a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cycloalkyl group having five to six carbon atoms, wherein the piperidinyl group, the pyrrolidinyl group, and the azetidinyl group each independently may be further substituted with a linear or branched alkyl group having 1 to 3 carbon atom(s), and the cycloalkyl group may be substituted with a linear or branched alkyl group having 1 to 3 carbon atom(s) optionally having a hydroxy group; and
$R_5$ is a cyano group, a halogen atom, or a methyl group; or
(9) The compound described in any one of (1) to (8) above or a pharmaceutically acceptable salt or ester thereof, in which:
$R_1$ is a methyl group, an ethyl group, a difluoromethyl group, a trifluoromethyl group, a cyclopropyl group, or a chlorine atom;
$R_2$ is a hydrogen atom;
one of $R_3$ and $R_4$ is a hydrogen atom, while the other one of $R_3$ and $R_4$ is a linear or branched alkyl group having 1 to 3 carbon atom(s) which is substituted with a dimethylamino group, an isopropylamino group, 1,1-dimethylpropylamino group, or t-butylamino group; a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cyclopentyl group which may be substituted with a methyl group or a hydroxymethyl group, wherein the piperidinyl group, the pyrrolidinyl group, and the azetidinyl group each independently may be further substituted with a linear or branched alkyl group having 1 to 3 carbon atom(s); and
$R_5$ is a cyano group, a fluorine atom, or a methyl group.
Also, another embodiment of the present invention may be expressed as (1x) to (3x) below:
(1x) A compound of Formula [I]:

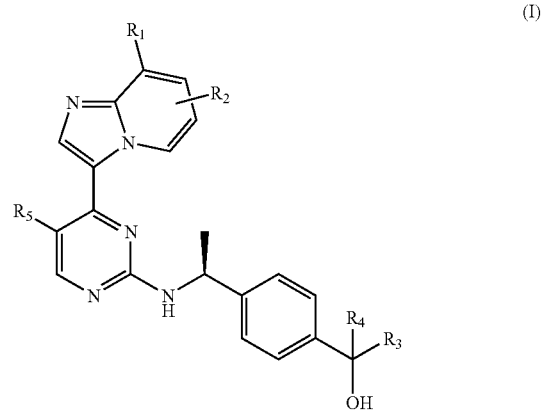

(I)

or a pharmaceutically acceptable salt or ester thereof wherein:
$R_1$ and $R_2$, which may be the same or different, are each a hydrogen atom; a substituent selected from <Substituent Group α>; a lower alkyl group which may be substituted with one or more substituents selected from <Substituent Group α>; or a cycloalkyl group having 3 to 6 carbon atoms, which may be substituted;

$R_3$ and $R_4$, which may be the same or different, are each:
a) a hydrogen atom;
b) a lower alkyl group substituted with $NR_aR_b$, where $R_a$ and $R_b$, which may be the same or different, are each a hydrogen atom, a lower alkyl group which may be substituted, or a benzyl group which may be substituted;
c) a substituent selected from <Substituent Group β>;
d) a lower alkyl group which may be substituted with one or more substituents selected from <Substituent Group β>;
e) a lower alkenyl group which may be substituted with one or more substituents selected from <Substituent Group β>;
f) a phenyl group;
g) a lower alkyl group substituted with a phenyl group;
h) a 4- to 7-membered aliphatic heterocyclic group;
i) a lower alkyl group substituted with a 4- to 7-membered aliphatic heterocyclic group;
j) a 5- or 6-membered aromatic heterocyclic group; or
k) a lower alkyl group substituted with a 5- or 6-membered aromatic heterocyclic group,
   wherein the phenyl group, the aliphatic heterocyclic group, and the aromatic heterocyclic group may be substituted with one or more substituents, which may be the same or different, selected from the following 1) to 4):
   1) a lower alkyl group;
   2) a substituent selected from <Substituent Group β>;
   3) a lower alkyl group substituted with one or more substituents selected from <Substituent Group β>; and
   4) a cycloalkyl group having 3 to 6 carbon atoms, which may be substituted with one or more substituents selected from <Substituent Group β>,
   and the aliphatic heterocyclic group may include an unsaturated bond, and the lower alkyl group as defined in the b), g), i), and k) above may be suitably substituted,
or alternatively, $R_3$ and $R_4$ are taken together to form a 4- to 7-membered aliphatic heterocyclic group,
   wherein the aliphatic heterocyclic group may be substituted with one or more substituents, which may be the same or different, selected from the following 1) to 4):
   1) a lower alkyl group;
   2) a substituent selected from <Substituent Group β>;
   3) a lower alkyl group substituted with one or more substituents selected from <Substituent Group β>; and
   4) a cycloalkyl group having 3 to 6 carbon atoms, which may be substituted with one or more substituents selected from <Substituent Group β>,
   and the aliphatic heterocyclic group may include an unsaturated bond;

$R_5$ is a cyano group, a halogen atom, or a lower alkyl group; and

<Substituent Group α> and <Substituent Group β> are defined as below:

<Substituent Group α>: a halogen atom, a hydroxy group, a nitro group, a cyano group, an amino group, a carbamoyl group, an aminosulfonyl group, an imino group, a lower alkylamino group, a dilower alkylamino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, and a carboxyl group; and <Substituent Group β>: a halogen atom, a hydroxy group, a nitro group, a cyano group, an amino group, a carbamoyl group, an aminosulfonyl group, an imino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, a carboxyl group, and a benzyl group; or (2x) The compound according to (1x) above or a pharmaceutically acceptable salt or ester thereof, wherein:
$R_1$ is a lower alkyl group having 1 or 2 carbon atom(s), which may be substituted with 1 to 3 fluorine atoms; a cyclopropyl group; or a chlorine atom;
$R_2$ is a hydrogen atom;
one of $R_3$ and $R_4$ is a hydrogen atom, while the other one of $R_3$ and $R_4$ is:
a) a lower alkyl group substituted with $NR_aR_b$, where $R_a$ and $R_b$, which may be the same or different, are each a hydrogen atom, a lower alkyl group, or a benzyl group;
b) a 4- to 6-membered aliphatic heterocyclic group selected from an azetidinyl group, a pyrrolidinyl group, a piperidinyl group, and a piperazinyl group; or
c) a lower alkyl group substituted with a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituent(s), which may be the same or different, selected from the following 1) to 4):
  1) a lower alkyl group;
  2) a substituent selected from the <Substituent Group β>;
  3) a lower alkyl group substituted with one or more substituent(s) selected from the <Substituent Group β>; and
  4) a cycloalkyl group having 3 to 6 carbon atoms, which may be substituted with one or more substituent(s) selected from the <Substituent Group β>; and
$R_5$ is a cyano group; or (3x) The compound according to (1x) or (2x) above or a pharmaceutically acceptable salt or ester thereof, wherein:
the <Substituent Group 3> is a halogen atom, a hydroxyl group, an amino group, a lower alkylsulfonyl group, and a lower alkoxy group;
one of $R_3$ and $R_4$ is a hydrogen atom, while the other one of $R_3$ and $R_4$ is:
a) a lower alkyl group substituted with $NR_aR_b$, where $R_a$ and $R_b$, which may be the same or different, are each a hydrogen atom or a lower alkyl group; or
b) a 5- or 6-membered aliphatic heterocyclic group selected from a pyrrolidinyl group and a piperidinyl group, wherein the aliphatic heterocyclic group may be substituted with one or more substituent(s), which may be the same or different, selected from the following 1) to 3):
  1) a lower alkyl group;
  2) a substituent selected from the <Substituent Group β>; and
  3) a lower alkyl group substituted with one or more substituent(s) selected from the <Substituent Group β>.

For the combined preparation according to the invention, which is formed with two separate preparations, it is preferable that one or both of the two separate preparations is/are oral preparation(s) or parental preparation(s).

In the combined preparation according to the invention which is formed with two separate preparations, preferably one preparation, together with a pharmaceutically acceptable carrier or diluent, is a preparation comprising:
(a)  2-[((1S)-1-{4-[2-(tert-butylamino)-1-hydroxyethyl]phenyl}ethyl)amino]-4-(8-ethylimidazo[1,2-a]pyridin-3-yl)pyrimidine-5-carbonitrile;
(b)  (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol;

(c) 2-[((S)-1-{4-[hydroxy(pyridin-2-yl)methyl]phenyl}ethyl)amino]-4-(8-methylimidazo[1,2-a]pyridin-3-yl) pyrimidine-5-carbonitrile;
(d) 4-(8-ethylimidazo[1,2-a]pyridin-3-yl)-2-({(1S)-1-[4-(4-hydroxy-1-methylpiperidin-4-yl) phenyl]ethyl}amino)pyrimidine-5-carbonitrile;.
(e) 4-(8-ethylimidazo[1,2-a]pyridin-3-yl)-2-[((1S)-1-{4-[hydroxy(1-isopropylpiperidin-4-yl) methyl]phenyl}ethyl)amino]pyrimidine-5-carbonitrile;
(f) 4-(8-cyclopropylimidazo[1,2-a]pyridin-3-yl)-2-[((S)-1-{4-[hydroxy(1-methylpiperidin-4-yl) methyl]phenyl}ethyl)amino]pyrimidine-5-carbonitrile;
(g) 4-(8-chloroimidazo[1,2-a]pyridin-3-yl)-2-[((1S)-1-{4-[(1-cyclopropylpiperidin-4-yl) (hydroxy)methyl]phenyl}ethyl)amino]pyrimidine-5-carbonitrile;
(h) 4-(8-ethylimidazo[1,2-a]pyridin-3-yl)-2-[((1S)-1-{4-[hydroxy(1-methylpiperidin-3-yl) methyl]phenyl}ethyl)amino]pyrimidine-5-carbonitrile;
(i) 2-{[(1S)-1-(4-{hydroxy[1-methylpyrrolidin-2-yl]methyl}phenyl)ethyl]amino}-4-(8-methylimidazo[1,2-a]pyridin-3-yl)pyrimidine-5-carbonitrile;
(j) 2-[((1S)-1-{4-[2-(tert-butylamino)-1-hydroxyethyl]phenyl}ethyl)amino]-4-(8-chloroimidazo[1,2-a]pyridin-3-yl)pyrimidine-5-carbonitrile;
(k) 2-[((1S)-1-{4-[2-(tert-butylamino)-1-hydroxyethyl]phenyl}ethyl)amino]-4-[8-(difluoromethyl) imidazo[1,2-a]pyridin-3-yl]pyrimidine-5-carbonitrile;
(l) 4-(8-cyclopropylimidazo[1,2-a]pyridin-3-yl)-2-[((1S)-1-{4-[(1,2-dimethylpyrrolidin-2-yl) (hydroxy)methyl]phenyl}ethyl)amino]pyrimidine-5-carbonitrile;
(m) (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol;
(n) (1S)-1-[4-((1S)-1-{[4-(8-chloroimidazo[1,2-a]pyridin-3-yl)-5-fluoropyrimidin-2-yl]amino}ethyl)phenyl]-2-[(1,1-dimethylpropyl)amino]ethanol;
(o) (1S)-1-[4-((1S)-1-{[4-(8-chloroimidazo[1,2-a]pyridin-3-yl)-5-fluoropyrimidin-2-yl]amino}ethyl)phenyl]-2-[(1-methylcyclopentyl)amino]ethanol;
(p) (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol;
(q) (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol;
(r) (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol;
(s) (1S)-2-(tert-butylamino)-1-{4-[(1S)-1-({5-fluoro-4-[8-(trifluoromethyl)imidazo[1,2-a]pyridin-3-yl]pyrimidin-2-yl} amino)ethyl]phenyl}ethanol;
(t) [4-((1S)-1-{[4-(8-chloroimidazo[1,2-a]pyridin-3-yl)-5-fluoropyrimidin-2-yl]amino}ethyl)phenyl](1,2-dimethylpyrrolidin-2-yl)methanol;
(u) 1-[4-((1S)-1-{[4-(8-chloroimidazo[1,2-a]pyridin-3-yl)-5-fluoropyrimidin-2-yl]amino}ethyl) phenyl]-2-(dimethylamino)-2-methylpropan-1-ol;
(v) [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol;
(w) [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol; or
(x) (1S)-2-(tert-butylamino)-1-{4-[(1S)-1-({4-[8-(difluoromethyl)imidazo[1,2-a]pyridin-3-yl]-5-fluoropyrimidin-2-yl} amino)ethyl]phenyl}ethanol,
or a pharmaceutically acceptable salt or ester thereof.

The combined preparation according to the invention which comprises two separate preparations may be further combined with at least one preparation including, together with a pharmaceutically acceptable carrier or diluent, an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents (here, the definition of each antitumor agent has the same meaning as defined above), or a pharmaceutically acceptable salt or ester thereof.

A pharmaceutical composition according to the invention preferably includes, together with a pharmaceutically acceptable carrier or diluent,
(a) 2-[((1S)-1-{4-[-2-(tert-butylamino)-1-hydroxyethyl]phenyl}ethyl)amino]-4-(8-ethylimidazo[1,2-a]pyridin-3-yl)pyrimidine-5-carbonitrile;
(b) (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol;
(c) 2-[((S)-1-{4-[hydroxy(pyridin-2-yl)methyl]phenyl}ethyl)amino]-4-(8-methylimidazo[1,2-a]pyridin-3-yl) pyrimidine-5-carbonitrile;
(d) 4-(8-ethylimidazo[1,2-a]pyridin-3-yl)-2-({(1S)-1-[4-(4-hydroxy-1-methylpiperidin-4-yl) phenyl]ethyl}amino)pyrimidine-5-carbonitrile;
(e) 4-(8-ethylimidazo[1,2-a]pyridin-3-yl)-2-[((1S)-1-{4-[hydroxy(1-isopropylpiperidin-4-yl) methyl]phenyl}ethyl)amino]pyrimidine-5-carbonitrile;
(f) 4-(8-cyclopropylimidazo[1,2-a]pyridin-3-yl)-2-[((S)-1-{4-[hydroxy(1-methylpiperidin-4-yl) methyl]phenyl}ethyl)amino]pyrimidine-5-carbonitrile;
(g) 4-(8-chloroimidazo[1,2-a]pyridin-3-yl)-2-[((1S)-1-{4-[(1-cyclopropylpiperidin-4-yl) (hydroxy)methyl]phenyl}ethyl)amino]pyrimidine-5-carbonitrile;
(h) 4-(8-ethylimidazo[1,2-a]pyridin-3-yl)-2-[((1S)-1-{4-[hydroxy(1-methylpiperidin-3-yl) methyl]phenyl}ethyl)amino]pyrimidine-5-carbonitrile;
(i) 2-{[(1S)-1-(4-{hydroxy[1-methylpyrrolidin-2-yl]methyl}phenyl)ethyl]amino}-4-(8-methylimidazo[1,2-a]pyridin-3-yl)pyrimidine-5-carbonitrile;
(j) 2-[((1S)-1-{4-[2-(tert-butylamino)-1-hydroxyethyl]phenyl}ethyl)amino]-4-(8-chloroimidazo[1,2-a]pyridin-3-yl)pyrimidine-5-carbonitrile;
(k) 2-[((1S)-1-{4-[2-(tert-butylamino)-1-hydroxyethyl]phenyl}ethyl)amino]-4-[8-(difluoromethyl) imidazo[1,2-a]pyridin-3-yl]pyrimidine-5-carbonitrile;
(l) 4-(8-cyclopropylimidazo[1,2-a]pyridin-3-yl)-2-[((1S)-1-{4-[(1,2-dimethylpyrrolidin-2-yl) (hydroxy)methyl]phenyl}ethyl)amino]pyrimidine-5-carbonitrile;
(m) (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol;
(n) (1S)-1-[4-((1S)-1-{[4-(8-chloroimidazo[1,2-a]pyridin-3-yl)-5-fluoropyrimidin-2-yl]amino}ethyl)phenyl]-2-[(1,1-dimethylpropyl)amino]ethanol;
(o) (1S)-1-[4-((1S)-1-{[4-(8-chloroimidazo[1,2-a]pyridin-3-yl)-5-fluoropyrimidin-2-yl]amino}ethyl)phenyl]-2-[(1-methylcyclopentyl)amino]ethanol;
(p) (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol;
(q) (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol;

(r) (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol;

(s) (1S)-2-(tert-butylamino)-1-{4-[(1S)-1-({5-fluoro-4-[8-(trifluoromethyl)imidazo[1,2-a]pyridin-3-yl]pyrimidin-2-yl}amino)ethyl]phenyl}ethanol;

(t) [4-((1S)-1-{[4-(8-chloroimidazo[1,2-a]pyridin-3-yl)-5-fluoropyrimidin-2-yl]amino}ethyl)phenyl](1,2-dimethylpyrrolidin-2-yl)methanol;

(u) 1-[4-((1S)-1-{[4-(8-chloroimidazo[1,2-a]pyridin-3-yl)-5-fluoropyrimidin-2-yl]amino}ethyl) phenyl]-2-(dimethylamino)-2-methylpropan-1-ol;

(v) [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol;

(w) [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol; or (x) (1S)-2-(tert-butylamino)-1-{4-[(1S)-1-({4-[8-(difluoromethyl)imidazo[1,2-a]pyridin-3-yl]-5-fluoropyrimidin-2-yl}amino)ethyl]phenyl}ethanol, or a pharmaceutically acceptable salt or ester thereof.

Hereinafter, representative processes for producing the compound of the present invention will be described.

Scheme 1a: Process for Producing Compound of Formula (I) from Compound of Formula (IIa)

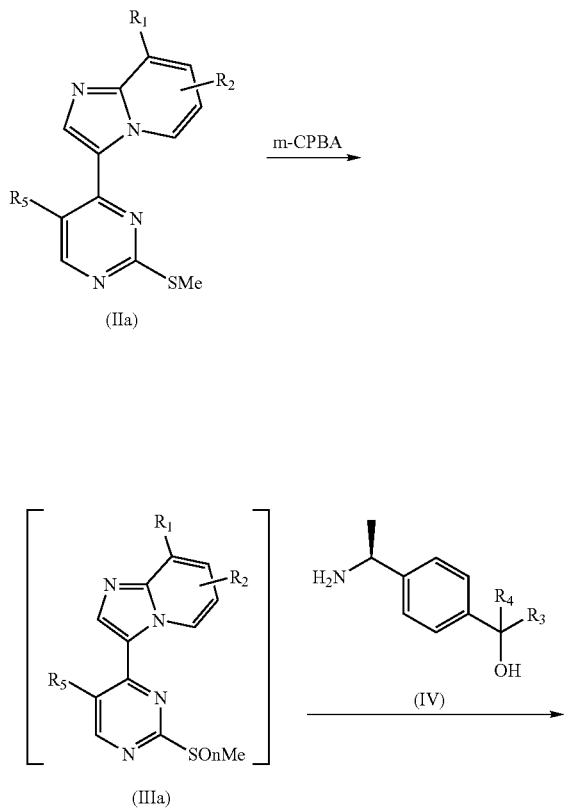

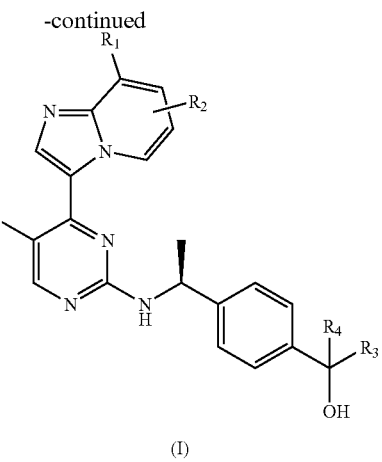

The compound of Formula (I) according to the invention (where $R_1$, $R_2$, $R_3$, $R_4$, and $R_5$ are the same as defined above) can be synthesized by first subjecting the compound of Formula (IIa) (where $R_1$, $R_2$, and $R_5$ are the same as defined above) to an oxidation reaction to obtain the compound of Formula (IIIa) (where $R_1$, $R_2$, and $R_5$ are the same as defined above, and n is 1 or 2) and then conducting a substitution reaction between the compound of Formula (IIIa) and phenethylamine represented by the above Formula (IV) (where $R_3$ and $R_4$ are the same as defined above).

The compound of Formula (IIIa) can be synthesized by oxidizing the compound of Formula (IIa) in a solvent such as dichloromethane, chloroform, N,N-dimethylformamide, or the like, with the use of an oxidizing agent such as m-chloroperbenzoic acid (m-CPBA), benzoyl peroxide, hydrogen peroxide solution, sodium periodate, or the like, preferably with the use of m-chloroperbenzoic acid. In the reaction, m-chloroperbenzoic acid (m-CPBA) is used in the amount of 2 to 5 moles, preferably 2 moles, to 1 mole of the compound of Formula (IIa). The reaction temperature can be appropriately selected by those having ordinary skill in the art in accordance with the starting compound used or the reaction solvent, but the reaction temperature is usually from 0° C. to room temperature. The reaction is usually completed in 1 to 24 hours, but the duration of the reaction can be appropriately increased or decreased. In addition, the obtained compound of the above Formula (IIIa) can be subject to the following reaction without being separated and purified.

The substitution reaction between the compound of above Formula (IIIa) and phenethylamine of above Formula (IV) is preferably carried out in the presence of a base (e.g., an inorganic base such as potassium carbonate and sodium hydrogen carbonate, or an organic base such as triethylamine and diisopropylethylamine). The reaction solvent for use includes chloroform, tetrahydrofuran, N,N-dimethylformamide, dimethylsulfoxide, and the like, and preferably includes chloroform and tetrahydrofuran. In the reaction, phenethylamine of above Formula (IV) is used in an amount of 0.5 to 3 moles, to 1 mole of the compound represented by Formula (IIIa). The reaction temperature can be appropriately selected by those having ordinary skill in the art in accordance with the starting compound used or the reaction solvent, but the reaction temperature is usually from room temperature to the boiling point of the solvent, preferably room temperature. The reaction is usually completed in 1 to 24 hours, but the duration of the reaction can be appropriately increased or decreased.

Scheme 1b: Process for Producing Compound of Formula (I) from Compound of Formula (IIb)

Scheme 2a: Representative Process for Producing Compound of Formula (IIa)

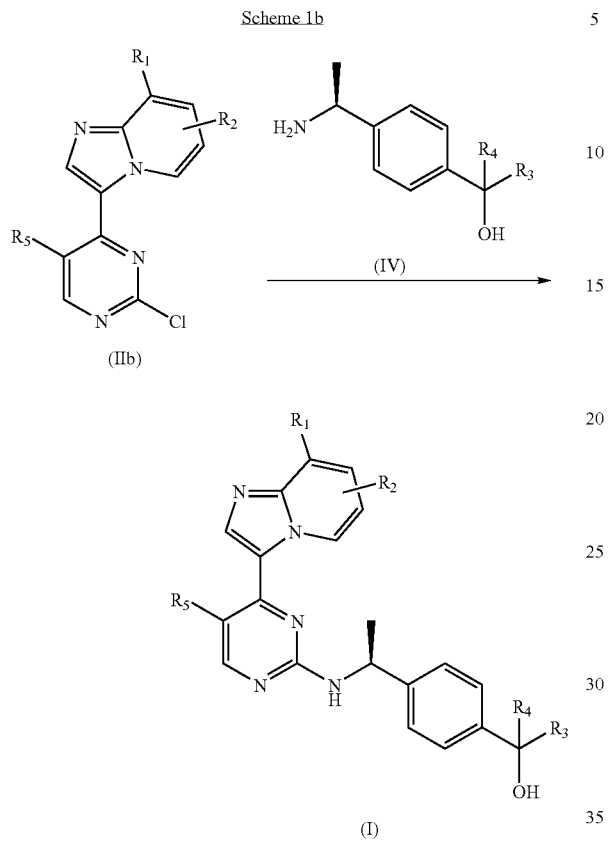

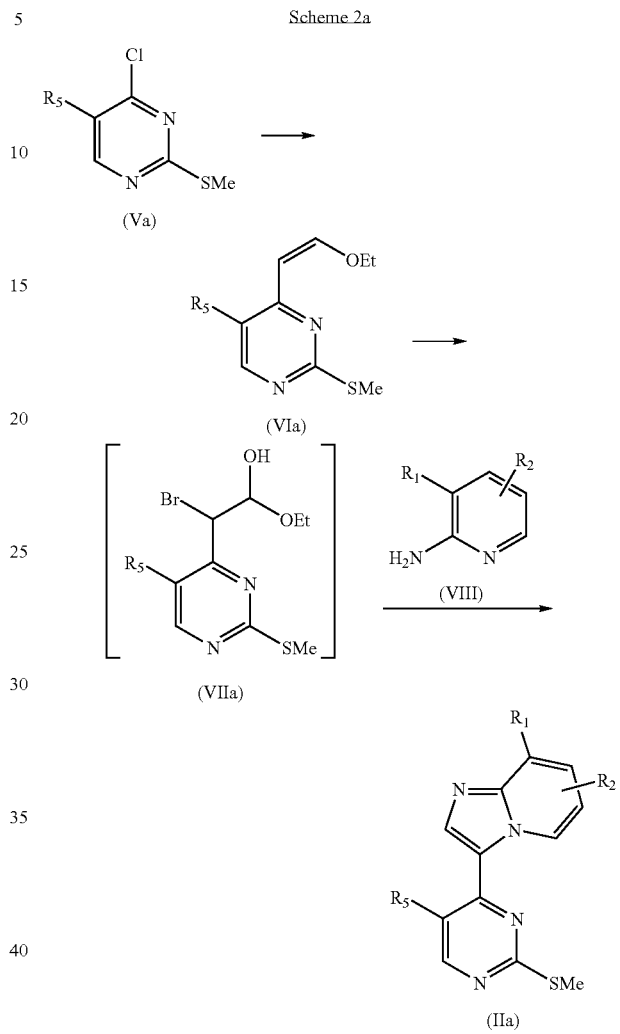

The compound of Formula (I) according to the invention (where $R_1$, $R_2$, $R_3$, $R_4$, and $R_5$ are the same as defined above) can be synthesized by conducting a substitution reaction between the compound of Formula (IIa) (where $R_1$, $R_2$, and $R_5$ are the same as defined above) and phenethylamine represented by the above Formula (IV) (where $R_3$ and $R_4$ are the same as defined above).

The substitution reaction between the compound of above Formula (IIb) and phenethylamine of above Formula (IV) is preferably carried out in the presence of a base (e.g., an inorganic base such as potassium carbonate, sodium carbonate, sodium cesium, and sodium hydrogen carbonate, or an organic base such as triethylamine and diisopropylethylamine). The reaction solvent for use includes chloroform, tetrahydrofuran, N,N-dimethylformamide, N,N-dimethylacetoamide, N-methyl-2-pyrrolidinone, dimethylsulfoxide, and the like, and preferably includes N, N-dimethylformamide, N,N-dimethylacetoamide, N-methyl-2-pyrrolidinone. In the reaction, phenethylamine of above Formula (IV) is used in an amount of 0.5 to 3 moles, to 1 mole of the compound represented by Formula (IIb). The reaction temperature can be appropriately selected by those having ordinary skill in the art in accordance with the starting compound used or the reaction solvent, but the reaction temperature is usually from room temperature to the boiling point of the solvent, preferably 80 to 200° C. The reaction is usually completed in 1 to 24 hours, but the duration of the reaction can be appropriately increased or decreased.

The compound of above Formula (VIa) (where $R_5$ is the same as defined above) can be synthesized by Still coupling reaction between cis-1-ethoxy-2-tri-n-butyltin (which can be synthesized according to the method disclosed in J. Am. Chem. Soc., 1977, 99, 7365) and the compound of above Formula (Va) (where $R_5$ is the same as defined above), using dichlorobis(triphenylphosphine)palladium (II) as a catalyst. The reaction solvent is preferably acetonitrile, and the reaction temperature is usually from room temperature to the boiling point of the solvent, and preferably the boiling point of the solvent. The reaction is usually completed in 1 to 24 hours, but the duration of the reaction can be appropriately increased or decreased.

The compound of above Formula (VIIa) (where $R_5$ is the same as defined above) can be prepared by reacting the compound of above Formula (VIa) with N-bromosuccinimide in 1,4-dioxane. In the reaction, 1 to 3 mole(s), preferably 1 mole of N-bromosuccinimide, to 1 mole of the compound of Formula (VIa) is used. The reaction temperature can be appropriately selected by those having ordinary skill in the art in accordance with the starting compound used, but the reaction temperature is preferably from 0° C. to room temperature.

The reaction is usually completed in 1 to 12 hours, but the duration of the reaction can be appropriately increased or decreased. The obtained Compound of Formula (VIIa) can be subject to the subsequent reaction without further isolation and purification.

The compound of above Formula (IIa) (where $R_1$, $R_2$, and $R_5$ are the same as defined above) can be synthesized from the compound of above Formula (VIIa) and the compound of above Formula (VIII) (where $R_1$ and $R_2$ are the same as defined above) in 1,4-dioxane. In the reaction, 1 to 3 mole(s), preferably 1 mole of the compound of above Formula (VIII), to 1 mole of the compound of Formula (VIIa) is used. The reaction temperature can be appropriately selected by those having ordinary skill in the art in accordance with the starting compound used, but the reaction temperature is usually from room temperature to the boiling point of the solvent, and preferably from room temperature to 50° C. The reaction is usually completed in 1 to 24 hours, but the duration of the reaction can be appropriately increased or decreased.

The compound of above Formula (Va), for example, is 4-chloro-2-(methylsulfanil)-5-pyrimidinecarbonitrile, or the like, and the compound of above Formula (VIII), for example, is 2-amino-3-picoline, or the like. These compounds are either commercially available or can be synthesized from a commercially available compound by a method generally known by those having ordinary skill in the art or a method analogous thereto (Literature: International Publication WO2004/043936, page 32-33, etc.).

Scheme 2b: Representative Process for Producing Compound of Formula (IIb)

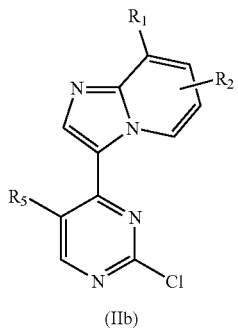

(IIb)

The compound of above Formula (IIb) (where $R_1$, $R_2$, and $R_5$ are the same as defined above) can be synthesized using the same method as shown in Scheme 2a from the compound of above Formula (Vb) (where $R_5$ is as defined above) as a starting material, in place of the compound of above Formula (Va) in Scheme 2a; refer to Scheme 2b.

The compound of above Formula (Vb), for example, is 2,4-dichloro-5-methylpyridine, and the like, and also the compound of above Formula (VIII), for example, is 2-aminopicolin, and the like, both of which are either commercially available or can be synthesized from a commercially available compound by a method generally known by those having ordinary skill in the art or a method analogous thereto (Literature: International Publication WO2004/043936, page 32 to 33, etc.).

Scheme 3: Representative Process for Producing Compound of Formula (IV)

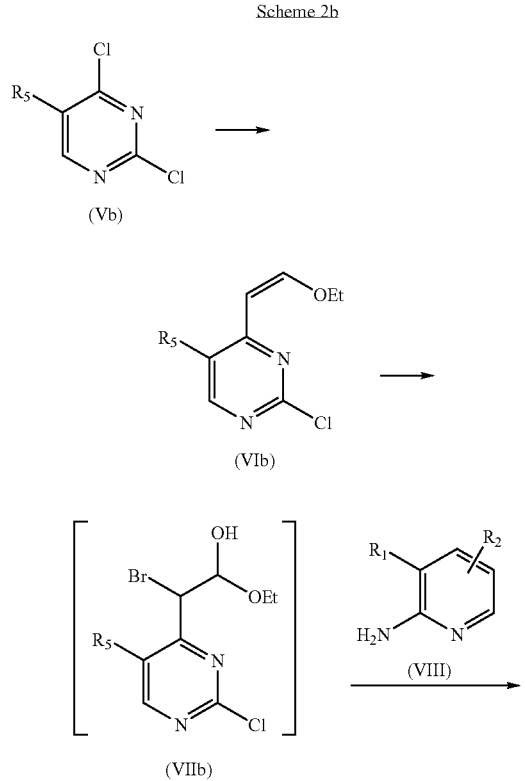

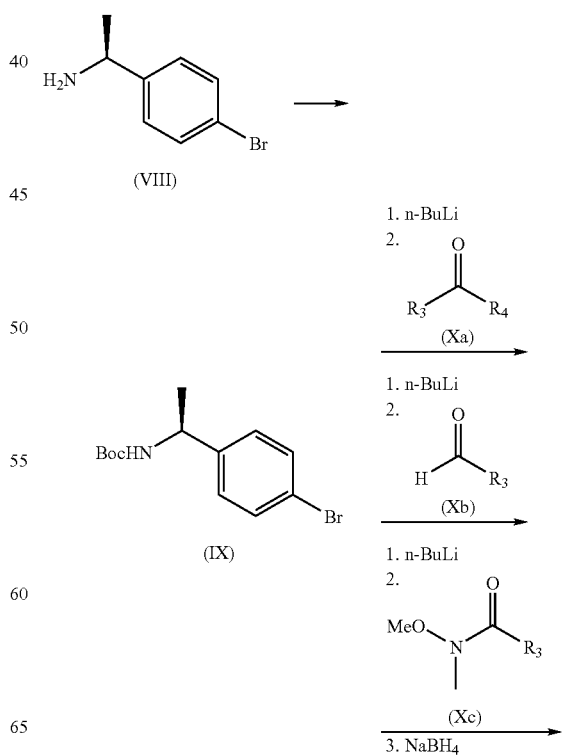

-continued

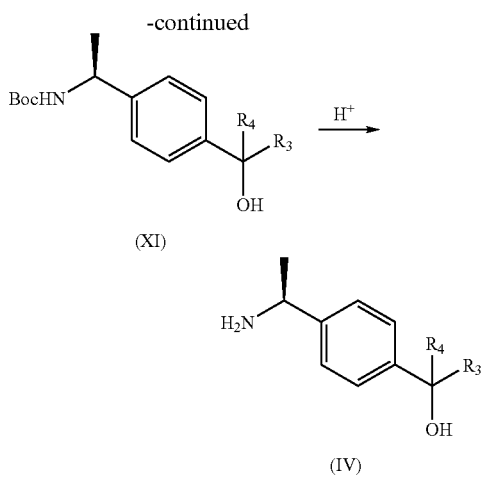

The compound of above Formula (IX) (where Boc is a tert-butoxycarbonyl group) can be synthesized using commercially available (S)-(−)-1-(4-bromophenyl)ethylamine (above compound (VIII)) in accordance with the method generally known by those having ordinary skill in the art (Literature: Protective Groups in Organic Synthesis, the third edition, written by T. W. Greene, John Wiley & Sons Publication, page 518-524, etc.).

Next, the compound of above Formula (XI) (where Boc, $R_3$, and $R_4$, are the same as defined above) can be synthesized by first subjecting n-butyllithium to the compound of above Formula (IX) in tetrahydrofuran to obtain aryllithium as a reaction intermediate and then reacting with a ketone of above Formula (Xa) (where $R_3$ and $R_4$ are the same as defined above) or an aldehyde of above Formula (Xb) (where $R_4$ is the same as defined above), both of which are an electrophile. In the reaction, 2 to 5 moles, preferably 2 moles of n-butyllithium, to 1 mole of the compound of Formula (IX) is used. In addition, 1 to 3 mole(s) of the ketone of above Formula (Xa) or the aldehyde of above Formula (Xb), to 1 mole of the compound of Formula (IX) is used. The reaction temperature is usually from −78° C. to 0° C., and preferably −78° C. The reaction is usually completed in 1 to 24 hours, but the duration of the reaction can be appropriately increased or decreased.

In addition, the compound of above Formula (XI) can also be synthesized by the following method. That is, the compound of above Formula (IX) is subject to n-butyllithium to obtain aryllithium as a reaction intermediate, which is then reacted with an electrophile such as Weinrebamide (Xc) (where $R_3$ is the same as defined above). The obtained compound is subjected to a reduction reaction with the use of sodium boronhydride to synthesize the compound of above Formula (XI). In the reaction, 2 to 5 moles, preferably 2 moles of n-butyllithium, to 1 mole of the compound of Formula (IX) is used. In addition, 1 to 3 mole(s) of the amide of above Formula (Xc), to 1 mole of the compound of Formula (IX) is used. The reaction temperature is usually from −78° C. to 0° C., and preferably −78° C. The reaction is usually completed in 1 to 24 hours, but the duration of the reaction can be appropriately increased or decreased. In the reduction reaction, 1 to 3 mole(s), preferably 1 mole of sodium boronhydride, to 1 mole of the compound of Formula (IX) is used.

The compound of above Formula (IV) (where $R_3$ and $R_4$ are the same as defined above) can be synthesized using the compound of above Formula (XI) in accordance with the method generally known by those having ordinary skill in the art (Literature: Protective Groups in Organic Synthesis, the third edition, written by T. W. Greene, John Wiley & Sons Publication, page 518-524, etc.).

The compound of above Formula (Xa), for example, is 1-methyl-4-piperidone, or the like, and the compound of above Formula (Xb), for example, is benzyl 2-formylpyrrolidine-1-carboxylate, or the like. The compound of above Formula (Xc), for example, is benzyl 4-(N-methoxy-N-methylcarbamoyl)piperidine-1-carboxylate, or the like. These compounds are either commercially available or can be synthesized from a commercially available compound by a method generally known by those having ordinary skill in the art or a method analogous thereto (Literature: Bioorg. Med. Chem., 2003, 11, 3153, Pamphlet of International Publication WO03/011285, page 60-61, etc.).

Scheme 4: Representative Process for Producing Compound of Formula (XVI)

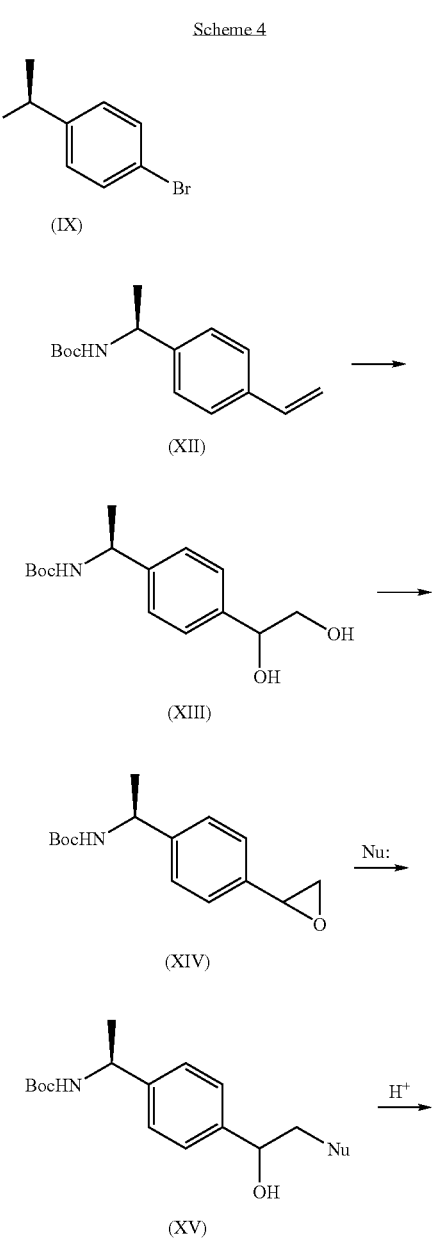

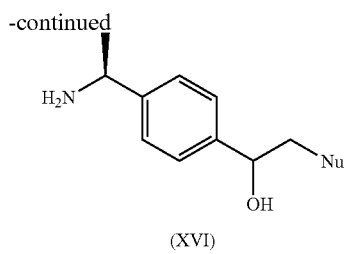

(XVI)

The compound of above Formula (XII) (where Boc is a tert-butoxycarbonyl group) can be obtained by subjecting to a coupling reaction the compound of above Formula (IX) (where Boc is the same as defined above) and potassium vinyltrifluoroborate or vinyltributyltin, in a solvent such as N,N-dimethylformamide, 1,4-dioxane, toluene, tetrahydrofuran, methanol, dimethoxyethane, or the like, in the presence of a palladium catalyst such as tetrakis(triphenylphosphine)palladium (0) or dichlorobis(triphenylphosphine)palladium (II). When potassium vinyltrifluoroborate is used herein, the reaction is preferably carried out in the presence of an inorganic base such as sodium carbonate, sodium hydrogen carbonate, or potassium carbonate, or an organic base such as triethylamine or diisopropylethylamine. In the reaction, the reaction temperature can be appropriately selected by those having ordinary skill in the art in accordance with the reagent used or the reaction solvent, but the reaction temperature is usually from room temperature to the boiling point of the solvent. The reaction is usually completed in 1 to 24 hours, but the duration of the reaction can be appropriately increased or decreased.

The compound of above Formula (XIII) (where Boc is the same as defined above) can be synthesized by subjecting the compound of above Formula (XII) to a dihydroxylation reaction in a mixed solvent of acetone and water with the use of osmium tetroxide and N-methylmorpholine N-oxide. It is preferable that the reaction is carried out usually from 0° C. to room temperature. The reaction is usually completed in 1 to 48 hours, but the duration of the reaction can be appropriately increased or decreased.

An optically active substance of the compound of above Formula (XIII) can be synthesized by subjecting the compound of above Formula (XII) to a sharpless asymmetric dihydroxylation reaction (Literature: Chem, Rev., 1994, 94, 2483, etc.) with the use of AD-mix-α or β (available from Aldrich Corporation), instead of osmium tetroxide, as an oxidizing agent.

The compound of above Formula (XIV) (where Boc is the same as defined above) can be synthesized by selectively introducing a leaving group to a primary hydroxyl group of the compound of above Formula (XIII) and then subjecting the resultant to a cyclization reaction by heating, in a solvent such as dichloromethane, chloroform, toluene, tetrahydrofuran, or the like, in the presence of either an inorganic base such as sodium hydroxide, potassium hydroxide, potassium carbonate, or the like, or an organic base such as triethylamine, diisopropylamine, pyridine, or the like. In this case, a methanesulphonyl group, p-toluenesulfonyl group, or the like can be used as a leaving group. In the reaction of introducing a leaving group, 1 to 3 mole(s), preferably 1.1 moles of methanesulphonyl chloride or p-toluenesulfonyl chloride, to 1 mole of the compound of above Formula (XIII) is used. The reaction temperature is from 0° C. to room temperature, and preferably 0° C. The reaction is usually completed in 1 to 24 hours, but the duration of the reaction can be appropriately increased or decreased.

The compound of above Formula (XV) (where Nu is a substituent derived from a nucleophilic agent such as a tert-butylamino group, and Boc is the same as defined above) can be synthesized by reacting an epoxide represented by the above Formula (XIV) with a nucleophilic agent in a solvent such as methanol, ethanol, or water. In the reaction, 1 mole to excessive amount, preferably about 10 moles of the nucleophilic agent, to 1 mole of the compound of above Formula (XV) is used. The reaction temperature can be appropriately selected by those having ordinary skill in the art in accordance with the starting compound used or the reaction solvent, but the reaction temperature is usually from room temperature to the boiling point of the solvent, and preferably from 40° C. to the boiling point of the solvent. The reaction is usually completed in 1 to 24 hours, but the duration of the reaction can be appropriately increased or decreased. The nucleophilic agent in the reaction, for example, is tert-butylamine, piperazine, or the like. These are either commercially available or can be synthesized from a commercially available compound by a method generally known by those having ordinary skill in the art or a method analogous thereto.

The compound of above Formula (XVI) (where Nu is the same as defined above) can be synthesized from the compound of above Formula (XV) in accordance with the method generally known by those having ordinary skill in the art (Literature: Protective Groups in Organic Synthesis, the third edition, written by T. W. Greene, John Wiley & Sons Publication, page 518-524, etc.).

In the production processes described in the above Schemes 1 to 4, desirable compounds can also be obtained by using the method commonly used in synthetic organic chemistry such as protecting or deprotecting methods of functional groups [for example, see Protective Groups in Organic Synthesis, the third edition, written by T. W. Greene, John Wiley & Sons Publication] as necessary.

Next, the PLK 1 inhibitory effect and cell proliferation inhibitory effect of the compound of Formula (I) will be explained.

1. Measurement of the Inhibitory Effect against PLK 1 Activity (Method A)

(1) Preparation of PLK1-T210D

It has been known that $210^{th}$ codon of human PLK1 which originally codes for threonine can be changed to an active type by altering the site into aspartic acid [Molecular and Cell Biology (Mol. Cell. Biol.), 17th edition, 3408 (1997)]. In order to obtain a human active type PLK1 protein, cDNA of mutated PLK1 (PLK1-T210D) of which the $210^{th}$ codon codes for aspartic acid by substituting a base in the $210^{th}$ codon of human PLK1 cDNA, was prepared. A baculovirus for which the N terminus of the PLK1-T210D cDNA is fused with GST (glutathione S-transferase) was prepared, and then the PLK1-T210D transfected into a *Spodoptera frugiperda* (Sf) 9 insect cell was highly expressed as a GST-fused protein. The cells were recovered and suspended in a lysis buffer (50 mM tris-hydrochloric acid buffer (pH 7.4)/150 mM sodium chloride/1 mM EDTA (ethylenediamine tetraacetic acid)/1 mM dithiothreitol/0.1% polyoxyethylene sorbitan monolaurate) to break cells with sonicator, and supernatant was recovered after a centrifugation. The supernatant was reacted on glutathione sepharose beads, and then the beads were washed with a lysis buffer. Thereafter, the beads were reacted in a lysis buffer containing Precision Protease (available from GE Healthcare Bioscience Company) to recover supernatant.

(2) Measurement of PLK1-T210D Activity

For the measurement of the PLK1-T210D activity, a synthetic peptide (arginine-arginine-arginine-aspartic acid-glutamic acid-leucine-methionine-glutamic acid-alanine-serine-phenylalanine-alanine-aspartic acid-glutamine-glutamic acid-alanine-lysine-valine) (SEQ. ID. NO.: 1) in which the serine surrounding sequence of the amino acid sequence No. 198 of CDC25C having been reported as the site for PLK1 substrate [EMBO Report, 3$^{rd}$ edition, 341 (2002)] is altered, was used as a substrate.

The reaction was carried out in accordance with the method of Toyoshima-Morimoto et al. [Nature, Vol. 410, 215-220, (2001)]. The volume of the reaction solution was 21.1 µL and the composition of the reaction buffer was 20 mM tris-hydrochloric acid buffer (pH 7.4)/10 mM magnesium chloride/0.5 mM dithiothreitol/1 mM EGTA (ethylene glycol-bis (beta-aminoethylether)-N,N,N',N',-tetraacetic acid). Thereto, purified PLK 1, 50 µM of the substrate peptide, 50 µM of non-labeled adenosine triphosphate (ATP), and 1 µCi of [γ-$^{33}$P]-labeled ATP (2000 to 4000 Ci/mmole) were added to carry out the reaction at 25° C. for 20 minutes. Then, 10 µL of 350 mM phosphate buffer was added to the reaction system to terminate the reaction. The resultant solution was spotted onto a multi-screen phosphocellulose filter on a 96-well plate. After washing the phosphocellulose filter with 75 mM phosphate buffer, the filter was dried to measure the radioactivity with a liquid scintillation counter. The non-labeled ATP and [γ-$^{33}$P]-labeled ATP were purchased from Amersham Bioscience Corp., and the multi-screen phosphocellulose filter was purchased from Millipore Corp.

The addition of the compound according to the invention to the reaction system was carried out by adding 1.1 µL of the solution prepared by preliminarily dissolving in dimethylsulfoxide at a 20-fold concentration of the final concentration. A control was provided by adding 1.1 µL of dimethylsulfoxide to the reaction system.

$IC_{50}$ value of the compound according to the invention for the PLK1-T210D activity was determined, and the results are shown in Table 1 below.

TABLE 1

| EXAMPLE No. of Compounds according to the present invention | PLK1-T210D inhibitory effect (nM) |
|---|---|
| 24 | 4.1 |
| 43 | 7.0 |
| 55 | 11 |

2. Measurement of Inhibitory Effect against PLK1 Activity (Method B)

(1) Preparation of PLK1 (Wild Type)

Human PLK1 was purchased from Carna Biosciences Inc. According to the Product Information from Carna Biosciences Inc., the present enzyme is an enzyme obtained by preparing a baculovirus for which the N terminus of a full-length cDNA of a wild type PLK1 is fused with GST (glutathione S-transferase), followed by highly expressing PLK1 transfected into an insect cell as a GST-fused protein, and then carrying out a purification with the use of glutathione sepharose chromatography.

(2) Measurement of PLK1 (Wild Type) Activity

For the measurement of the PLK1 activity, a synthetic peptide (arginine-arginine-arginine-aspartic acid-glutamic acid-leucine-methionine-glutamic acid-alanine-serine-phenylalanine-alanine-aspartic acid-glutamine-glutamic acid-alanine-lysine-valine) (SEQ. ID. NO.: 1) in which the serine surrounding sequence of the amino acid sequence No. 198 of CDC25C having been reported as the site for PLK1 substrate [EMBO Report, 3$^{rd}$ edition, 341 (2002)] is altered, was used as a substrate for the PLK1.

The reaction was carried out in accordance with the method as described by Toyoshima-Morimoto et al. [Nature, Vol. 410, 215-220, (2001)]. The volume of the reaction solution was 10.5 µl and the composition of the reaction buffer was a 20 mM Tris-HCl buffer (pH 7.4)/10 mM magnesium chloride/ 0.5 mM dithiothreitol/1 mM EGTA (ethylene glycol-bis (beta-aminoethylether-N,N,N',N'-tetraacetic acid). Thereto, purified PLK1, 20 µM of the substrate peptide, 10 µM of non-labeled adenosine triphosphate (ATP), and 0.3 µCi [γ-$^{33}$P]-labeled ATP (>2500 Ci/mmole) were added to perform the reaction at a reaction temperature of 25° C. for 120 minutes. Thereafter, 20 µl of a 350 mM phosphate buffer was added to the reaction system to terminate the reaction, and the resultant solution was spotted onto a multi-screen phosphocellulose filter on a 384-well plate. After the phosphocellulose filter is washed with a 75 mM phosphate buffer and then dried, the radioactivity was measured with a liquid cintillation counter. The non-labeled and [γ-$^{33}$P]-labeled ATPs, and the multi-screen phosphocellulose filter were purchased from GE Healthcare Bio-Sciences, and Millipore Corporation, respectively.

Addition of the compound of the present invention to the reaction system was carried out by adding 0.5 µl of the solution prepared by preliminarily dissolving the compound in dimethylsulfoxide at a 20-fold concentration of the final concentration. A control was provided by adding 0.5 µl of dimethylsulfoxide to the reaction system.

$IC_{50}$ value of the compound of the present invention for the PLK 1 activity was determined, and the results are shown in Table 2 below.

TABLE 2

| EXAMPLE No. of Compounds according to the present invention | PLK1 (Wild Type) inhibitory effect (nM) |
|---|---|
| 5 | 2.3 |
| 24 | 1.4 |
| 43 | 1.4 |
| 66 | 1.8 |
| 67 | 2.6 |
| 71 | 2.2 |
| 73 | 10 |
| 85 | 3.4 |
| 89 | 2.4 |

As shown above, the same results on the inhibitory activity of the compound of the invention against PLK1 can be obtained by any of Method A and Method B, and it is clear that the inhibitory activity is remarkably high.

3. Measurement of the Inhibitory Effect against Cell Proliferation: Measurement of the Inhibitory Activity Against PLK1 at Cellular Level (1) Method of Cell Culture For the measurement of the PLK 1 inhibitory activity of the compound at a cellular level, human uterine cervix cancer cell lines HeLaS3 cells were used. The HeLaS3 cell was obtained from American Type Culture Collection (ATTC), and cultured in a $CO_2$-incubator of saturated steam by using Dulbecco's Modified Eagle's Medium containing 10% fetal calf serum at 37° C. in the presence of 5% $CO_2$.

(2) Measurement of Inhibitory Activity of the Compound According to the Invention It has been reported that PLK 1 plays an important role in various stages of mitotic phase (M-phase) in mammalian cells (Nature Review Molecular Cell Biology (Nat. Rev. Mol. Cell. Biol.), Vol. 5, 429, (2004)). In fact, when mammalian cells are treated with PLK 1 siRNA to control the expression level, the cell cycle progression is inhibited and thus the cells are arrested at M phase. At the time, when the phosphorylation level of $10^{th}$ serine residue on histone H3, which is thought to be required for a chromosome condensation in M phase, is examined, then it is observed that the level is enhanced to a high level. Thus, after treating the cells with the compound according to the invention, the phosphorylation level of histone H3 was examined by the indirect fluorescent antibody technique; the M phase cells were identified by using the level thereof as an indicator to analyze the ratio of cells arrested at M phase; and further EC50 value of each compound was calculated to evaluate the PLK1 inhibitory activity at a cellular level.

First, HeLaS3 cells were seeded into a lysine-treated 96-well plate (Falcon Corp.) in the proportion of 3,000 per one well, and allowed to stand still in the above-mentioned $CO_2$ incubator. 24 hours after the seeding, the compound according to the invention, which is diluted in series, was added into each well of the plate, and further allowed to stand still in the $CO_2$ incubator. 18 hours after the addition of the compound according to the invention, the culture medium containing the compound according to the invention in each well of the plate was removed, and then 100 μL of ice-cold 100% methanol (Wako Pure Chemical Industries, Ltd.) was added, to carry out cell fixation for 10 minutes and treatment of increasing the membrane permeability. Subsequently, to the wells in which the methanol was removed, 50 μL of 1% BSA/PBS was added, and then blocking was carried out for 30 minutes. Thereafter, for the primary antibody reaction, 50 μL of 1% BSA/PBS containing a 2.5 mg/mL Anti-phospho Histone H3 (Ser10) antibody (Upstate Corp.) was added to the wells, and the plate was left over at room temperature for 90 minutes. After terminating the reaction, each well was once washed with PBS; and for the second antibody reaction, 50 μL of 1% BSA/PBS containing 1.5 mg/mL Cy5-labelled antirabbit IgG (H+L) antibody (Chemicon) and 10 ug/mL DAPI (Sigma) which is a nucleus staining regent, was added, and further left over at room temperature for 90 minutes. After terminating the reaction, the reaction solution in wells was removed and replaced with 100 μL of PBS, and then fluorescence images were captured by using IN Cell Analyzer 1000 (manufactured by GE Amersham) to analyze the ratio of M phase cells (Mitotic index) in each view. When the maximum value of the ratio of cells arrested at M phase which can be induced by each drug is assumed as 100%, the drug concentration required for inducing 50% out of that 100% is defined as EC50.

$EC_{50}$ values obtained by the above-mentioned method are shown in Table 3 below.

TABLE 3

| EXAMPLE No. of Compounds according to the present invention | Inhibitory effect against cell proliferation (nM) |
|---|---|
| 5 | 2.6 |
| 24 | 4.6 |
| 43 | 4.0 |
| 55 | 5.0 |
| 66 | 2.9 |
| 67 | 4.0 |
| 71 | 3.5 |
| 73 | 5.7 |

TABLE 3-continued

| 85 | 11 |
| 89 | 13.9 |

| EXAMPLE No. of Compounds disclosed in WO2006/025567 | Inhibitory effect against cell proliferation (nM) |
|---|---|
| 105 | 118.4 |
| 152 | 555.6 |
| 153 | 72.3 |

As shown in Table 3, since the compound of the invention exhibits a strong inhibitory effect against cell proliferation, it is considered to be extremely useful as an antitumor agent. As compared with the compounds disclosed in International Publication WO2006/025567, it is apparent that the compound of the invention exhibits remarkably more excellent inhibitory activity against cell proliferation, due to having the following partial structure:

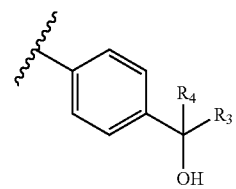

As mentioned above, the compound according to the invention has an excellent PLK1 inhibitory activity and also has a strong inhibitory effect against cell proliferation. Therefore, it is believed to be useful as an antitumor agent for strongly inhibiting the proliferation of cancerous cells. That is, a pharmaceutical composition containing the novel substituted aminopyrimidine derivative according to the invention or a pharmaceutically acceptable salt or ester thereof, or an antitumor agent containing the novel substituted aminopyrimidine derivative according to the invention or a pharmaceutically acceptable salt or ester thereof, is believed to be effective for the treatment of cancer patients. In addition, the pharmaceutical composition or the antitumor agent may contain pharmaceutically acceptable carriers or diluents. Here, the term "pharmaceutically acceptable carriers or diluents" refers to excipients [e.g., fats, bees wax, semi-solid or liquid polyol, natural or hydrogenated oil, etc.]; water (e.g., distilled water, especially distilled water for injection, etc.), physiological brine, alcohol (e.g., ethanol), glycerol, polyol, aqueous glucose solution, mannitol, vegetable oil, or the like; additives [e.g. bulking agent, disintegrant, binder, lubricant, wetting agent, stabilizer, emulsifier, dispersant, preservative, sweetener, colorant, flavoring agent or aromatic substance, thickening agent, diluent, buffering substance, solvent or solubilizer, drug for attaining storage effect, salt for adjusting osmotic pressure, coating agent, or antioxidant], and the like.

The compound according to the invention can also be used as a prodrug containing ester. Here, the term "prodrug" generally refers to a derivative in which a certain drug molecule is chemically modified, which itself shows no physiological activity but after being administered in vivo, transforms back to its original drug molecule to exhibit drug efficacy. As the prodrug of the compound according to the invention, a compound of above Formula (I) in which the hydroxyl group is acylated with a phosphate group or the like can be exemplified. The prodrug and ester can be produced in accordance with the method commonly known or used by those having ordinary skill in the art.

Furthermore, for tumors suitable for expecting a therapeutic effect of the compound according to the invention, for example, human solid tumors and the like may be mentioned. Examples of the human solid tumors include cerebral cancer, head and neck cancer, esophageal cancer, thyroid cancer, small cell cancer, non-small cell cancer, breast cancer, gastric cancer, gall bladder/bile duct cancer, hepatic cancer, pancreatic cancer, colon cancer, rectal cancer, ovarian cancer, chorioepithelioma, uterine cancer, cervical cancer, renal pelvic/ureteral cancer, urinary bladder cancer, prostate cancer, penile cancer, testicular cancer, embryonal cancer, Wilms' tumor, skin cancer, malignant melanoma, neuroblastoma, osteosarcoma, Ewing's sarcoma, soft tissue sarcoma, and the like.

Next, the "pharmaceutically acceptable salt or ester thereof" described above will be explained.

When the compound according to the invention is used as an antitumor agent or the like, the compound can be used in the form of a pharmaceutically acceptable salt thereof. Typical examples of the pharmaceutically acceptable salt include inorganic acid salts such as salts with alkali metals, e.g., sodium, potassium, and the like, hydrochloride, sulfate, nitrate, phosphate, carbonate, hydrogen carbonate, and hyperchlorate; organic acid salts such as acetate, propionate, lactate, maleate, fumarate, tartrate, malate, citrate, and ascorbate; sulfonates such as methanesulfonate, isethionate, benzenesulfonate, and toluenesulfonate; acidic amino acid salts such as aspartate and glutamate; and the like. A preferred salt of the compound according to the invention is a hydrochloride salt, and the like.

Preparation of the Pharmaceutically Acceptable Salts of the Compound According to the invention can be carried out by appropriately combining methods that are conventionally used in the field of organic synthetic chemistry. Specifically, a method of neutrally titrating a solution of the compound according to the invention in a free form using an alkaline solution or an acidic solution, or the like, may be mentioned.

Examples of the ester of the compound according to the invention include methyl ester, ethyl ester, and the like. These esters can be prepared by esterifying a free carboxyl group according to standard methods.

For the administration form used when administering the compound according to the invention as an antitumor agent or the like, various forms can be selected. For example, oral preparations such as tablet, capsule, powder, granule, and liquid; and sterilized liquid parenteral preparations such as solution and suspension, and the like may be mentioned.

Here, solid preparations can be prepared, without modifications, in the form of tablet, capsule, granule, or powder according to standard methods, but can be also prepared using appropriate additives. Examples of the additives include sugars such as lactose and glucose; starches such as those from corn, wheat, and rice; fatty acids such as stearic acid; inorganic salts such as sodium metasilicate, magnesium aluminate, and anhydrous calcium phosphate; synthetic polymers such as polyvinylpyrrolidone and polyalkylene glycol; fatty acid salts such as calcium stearate and magnesium stearate; alcohols such as stearyl alcohol and benzyl alcohol; and synthetic cellulose derivatives such as methylcellulose, carboxymethylcellulose, ethylcellulose, and hydroxypropylmethylcellulose. In addition to these, generally used additives such as water, gelatin, talc, vegetable oils, and gum arabic, and the like, may be mentioned.

These solid preparations such as tablet, capsule, granule, and powder may usually contain 0.1 to 100% by weight, preferably 5 to 100% by weight, of the active ingredient.

Liquid preparations can be prepared in the form of suspension, syrup, injectable preparation, or the like, using appropriate additives which are generally used for liquid preparations, such as water, alcohols, plant-derived oils e.g., soybean oil, peanut oil, sesame oil, and the like.

In particular, examples of appropriate solvent or diluent useful in the case of parenterally administering via intramuscular injection, intravenous injection, or subcutaneous injection, include distilled water for injection, aqueous solution of lidocaine hydrochloride (for intramuscular injection), physiological brine, aqueous glucose solution, ethanol, fluid for intravenous injection (e.g., aqueous solution of citric acid, sodium citrate, and the like), electrolyte solution (e.g., fluid for infusion or for intravenous injection), and the like, and mixed solutions thereof.

These injectable preparations may be in a form of powder or compound with suitable additives which is to be dissolved at the time of use, in addition to the form that preliminarily dissolved. Such injectable liquid can usually contain 0.1 to 10% by weight of the active ingredient.

The liquid for oral administration, such as suspension, syrup or the like, can contain 0.5 to 10% by weight of the active ingredient.

For the treatment according to the invention, the preferred course of medication may be varied in accordance with the administration form of the compound represented by Formula (I), the kind of compound represented by Formula (I) to be used, the formulation comprising the compound represented by Formula (I) to be used; the kind, administration form, and formulation of other antitumor agent(s) to be used in combination; and cancerous cells to be treated and the conditions of the patient. The most suited treatment under a predetermined condition can be determined by those having ordinary skill in the art on the basis of a commonly used therapy course and/or considering the present specification.

The preferred amount of the compound according to the invention to be administered in practice can be appropriately increased or decreased in accordance with the kind of the compound to be used, the kind of the composition mixed, the frequency of administration, the specific site to be treated, and conditions of the patient. For example, the daily dose for an adult is, in the case of oral administration, 10 to 500 mg, and in the case of parenteral administration, preferably intravenous injection, 10 to 100 mg, per day. In addition, the dose frequency may vary depending on the mode of administration and symptoms, but the administration can be conducted once, or divided into 2 to 5 portions.

The course of the compound represented by the Formula (I) and other antitumor agents to be used in combination is not particularly limited, but can be appropriately determined in accordance with the public literature: as necessary by those having ordinary skill in the art. For example, the course can be determined as follows.

For the course of 5-fluorouracil (5-FU), for example, in the case of oral administration, 200 to 300 mg/day thereof are given 1 to 3 times daily, and in the case of injection, 5 to 15 mg/kg/day thereof are given once daily for the first 5 days via intravenous infusion or drip infusion and thereafter 5 to 7.5 mg/kg thereof are given once on every other day via intravenous infusion or drip infusion (dosage may be appropriately increased or reduced).

For the course of S-1 (tegafur, CDHP, and potassium oxonate), for example, the initial dosage (single dose) is adjusted to a body surface area as the standard for the next time, and oral administration of 28-day course is given twice daily each after having breakfast and dinner and then discontinued for 14 days. This mode of administration as one course is repeated. The initial dosage per body surface area (tegafur equivalent) is (if the area is under 1.25 m$^2$) 40 mg/frequency; (if the area is 1.25 m$^2$ or more to less than 1.5 m$^2$) 50 mg/frequency; and (if the area is 1.5 m$^2$ or more) 60 mg/frequency, which can be appropriately increased or decrease in accordance with the conditions of the patient.

For the course of gemcitabine, for example, 1 g/m$^2$ of gemcitabine are given over 30 minutes via drip infusion, once per a week for 3 weeks continuously, and then discontinued on the fourth week. This mode of administration as one course is repeated. The dosage is appropriately decreased in accordance with age, symptoms, and occurrence of side effects.

For the course of doxorubicin (for example, doxorubicin hydrochloride), in the case of intravenous injection, for example, 10 mg/day (0.2 mg/kg) (titer) of doxorubicin are given once daily for 4 to 6 days all at one shot into the vein, and then discontinued for 7 to 10 days. This mode of administration as one course is repeated for 2 or 3 times. The total dosage is preferably 500 mg or less (titer)/m$^2$ (body surface area), which may be appropriately increased or decreased within the given range.

For the course of etoposide, in the case of intravenous injection, for example, 60 to 100 mg/m$^2$ (body surface area) of etoposide are given daily for 5 days, and discontinued for 3 weeks (dosage may be appropriately increased or decreased). This mode of administration as one course is repeated. On the other hand, in the case of oral administration, for example, 175 to 200 mg/day thereof are given continuously for 5 days, and discontinued for 3 weeks (dosage may be appropriately increased or decreased). This mode of administration as one course is repeated.

For the course of docetaxel (docetaxel hydrate), for example, 60 mg/m$^2$ (body surface area) of docetaxel are given once a day over 1 or more hour(s) at a 3- or 4-week interval via drip infusion (dosage can be appropriately increased or decreased).

For the course of paclitaxel, for example, 210 mg/m$^2$ (body surface area) thereof are given once a day over 3 hours via drip infusion, and then discontinued for at least 3 weeks. This mode of administration as one course is repeated. The dosage can be appropriately increased or decreased.

For the course of cisplatin, in the case of intravenous injection, for example, 50 to 70 mg/m$^2$ (body surface area) thereof are given once a day, and then discontinued for 3 or more weeks (dosage may be appropriately increased or decreased). This mode of administration as one course is repeated.

For the course of carboplatin, for example, 300 to 400 mg/m$^2$ thereof are given once a day over 30 minutes or more via drip infusion, and discontinued for at least 4 weeks (dosage may be appropriately increased or decreased). This mode of administration as one course is repeated.

For the course of oxaliplatin, 85 mg/m$^2$ thereof are given once a day via intravenous infusion, and then discontinued for 2 weeks. This mode of administration as one course is repeated.

For the course of irinotecan (for example, irinotecan hydrochloride), for example, 100 mg/m$^2$ thereof are given once a day at weekly intervals via drip infusion for 3 or 4 times, and then discontinued for at least 2 weeks.

For the course of topotecan, for example, 1.5 mg/m$^2$ thereof are given once a day for 5 days via drip infusion, and then discontinued for at least 3 weeks.

For the course of cyclophosphamide, in the case of intravenous infusion, for example, 100 mg thereof are given daily via intravenous infusion, and the dosage may be increased to 200 mg/day if the patient can tolerate it. The total dosage to be given is from 3000 to 8000 mg, but may be appropriately increased or decreased. In addition, it may be administered via intramuscular, intrathoracic, or intratumor, injection or infusion. Alternatively, in the case of oral administration, for example, 100 to 200 mg thereof are given once a day.

For the course of gefitinib, for example, 250 mg of gefitinib are given once a day via oral administration.

For the course of cetuximab, for example, 400 mg/m$^2$ thereof are given on a first day via drip infusion, and then 250 mg/m$^2$ thereof are given weekly via drip infusion.

For the course of bevacizumab, for example, 3 mg/kg thereof are given weekly via drip infusion.

For the course of trastuzumab, for example, 4 mg/kg (body weight) thereof at the first administration and 2 mg/kg thereof at the next administrations are given once a day for an adult, over 90 minutes or more at weekly intervals via drip infusion.

For the course of exemestane, for example, 25 mg thereof are given once a day after a meal via oral administration for an adult.

For the course of leuproreline (for example, acetic acid leuproreline), for example, 11.25 mg thereof are given once every 12 weeks via subcutaneous administration for an adult.

For the course of imatinib, for example, 400 mg thereof are usually given once a day after a meal via oral administration for an adult with chronic phase chronic myelogenous leukemia.

For the course of combined preparation of 5-FU and leucovorin, for example, 425 mg/m$^2$ of 5-FU and 200 mg/m$^2$ of leucovorin are given on the first to fifth day via drip infusion, which then repeated at a 4-week interval.

EXAMPLES

Hereinafter, the present invention will be described in more detail with reference to Examples, but the invention is not intended to be limited by the Examples by any means. In Examples, thin layer chromatography was performed using Silica gel$_{60}$F$_{254}$ (Merck & Co., Inc.) or NH (Fuji Silysia Chemical, Ltd.) for the plate, and a UV detector for the detection. Wakogel™C-300 or C-200 (Wako Pure Chemical Industries, Ltd.), NH (Fuji Silysia Chemical, Ltd.), Biotage Si or Biotage NH (Biotage), or Purif-Pack (MORITEX) was used as the silica gel for column. In a preparative reversed phase liquid chromatography, CombiPrep Pro C18 (YMC) was used for a column, and 0.1% trifluoroacetic acid aqueous solution and 0.1% trifluoroacetic acid acetonitrile solution were used for a mobile phase. For the MS spectra, JMS-SX102A (JEOL, Co. Ltd.), or QUATTRO II (Micromass) was used, or for the LC-MS, ZMD (Micromass) was used, for the measurement. For the NMR spectra, dimethylsulfoxide was used as the internal standard in the case of measuring in a deuterated dimethylsulfoxide solution, tetramethylsilane was used as the internal standard in the case of measuring in a deuterated chloroform solution, and methanol was used as the internal standard in the case of measuring in a deuterated methanol solution. In addition, a spectrometer such as Mercury 400 (400 MHz; Varian, Inc.), Inova 400 (400 MHz; Varian, Inc.), or JNM-AL400 (400 MHz; JEOL, Co. Ltd.) was used for the measurement. All δ values were expressed in ppm.

The meanings of the abbreviations used in Examples are given below.

s: Singlet
d: Doublet
dd: Double doublet
t: Triplet
dt: Double triplet q: Quartet
dq: Double quartet
quint: Quintet
m: Multiplet
br: Broad
brs: Broad singlet
J: Coupling constant
Hz: Hertz
DMSO-$d_6$: Deuterated dimethylsulfoxide
$CDCl_3$: Deuterated chloroform
$CD_3OD$: Deuterated methanol
RT: Retention time Hereinbelow, structural formulae of compounds of Examples 1 to 93 will be shown in Tables 4 to 15. In the tables, compounds marked with * near by an asymmetric carbon atom to which $R_3$, $R_4$, and OH are bonded, indicate that one of their asymmetric carbon atoms is in an R-form and the other one is in an S-form.

However, Examples 41 to 44 are shown as follows. In Table 9, compounds marked with  near by an asymmetric carbon atom to which $R_3$, $R_4$, and OH are bonded, indicate that the asymmetric carbon atoms are the same isomers of either an R-form or an S-form. Meanwhile, compounds marked with * indicate that their asymmetric carbon atoms are the same isomers of either an R-form or an S-form, but they are the different isomers from the compounds marked with **.

TABLE 4

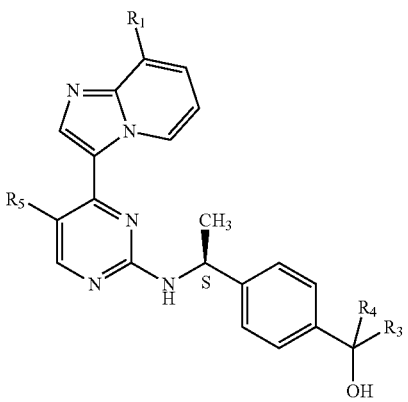

| Example | $R_1$ | $R_5$ | (structure) |
|---|---|---|---|
| 1 | $CH_3$ | CN | 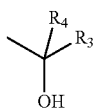 |
| 2 | $CH_3$ | CN | 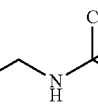 |
| 3 | $CH_3$ | CN | 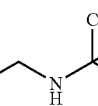 |

TABLE 4-continued

| Example | $R_1$ | $R_5$ | (structure) |
|---|---|---|---|
| 4 | $CH_3$ | CN | 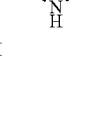 |
| 5 | $CH_2CH_3$ | CN | 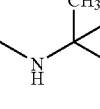 |
| 6 | $CH_2CH_3$ | CN | 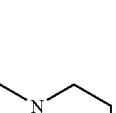 |
| 7 | $CH_2CH_3$ | CN | 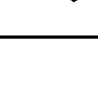 |
| 8 | $CH_2CH_3$ | CN |  |

TABLE 5

| Example | R₁ | R₅ | $\overset{R_4}{\underset{OH}{\overset{|}{C}}}R_3$ |
|---------|-----|-----|---|
| 9 | Cl | CN | CH₃CH(R)(OH)CH₂NHC(CH₃)₃ |
| 10 | CHF₂ | CN | CH₃CH(R)(OH)CH₂NHC(CH₃)₃ |
| 11 | CH₂CH₃ | Br | CH₃CH(R)(OH)CH₂NHC(CH₃)₃ |
| 12 | CH₃ | CN | 1-(pyridin-2-yl)ethanol |
| 13 | CH₃ | CN | 1-phenylethanol |
| 14 | CH₃ | CN | 1-(1-methyl-1H-imidazol-2-yl)ethanol |
| 15 | CH₃ | CN | 1-(pyridin-4-yl)ethanol |

TABLE 5-continued

| Example | R₁ | R₅ | $\overset{R_4}{\underset{OH}{\overset{|}{C}}}R_3$ |
|---------|-----|-----|---|
| 16 | CH₃ | CN | 1-phenylpropan-2-ol |

TABLE 6

| Example | R₁ | R₅ | $\overset{R_4}{\underset{OH}{\overset{|}{C}}}R_3$ |
|---------|-----|-----|---|
| 17 | CH₃ | CN | 1-(1-methylpiperidin-4-yl)propan-2-ol |
| 18 | CH₃ | CN | 4-methylpiperidin-4-ol |
| 19 | CH₃ | CN | 3-methyl-1-methylpyrrolidin-3-ol |

TABLE 6-continued

[Structure: Imidazopyridine-pyrimidine-phenyl-C(R3)(R4)OH scaffold with R1, R5 substituents]

| Example | R1 | R5 | (R3/R4 group) |
|---|---|---|---|
| 20 | CH₂CH₃ | CN | 4-hydroxy-4-methyl-1-methylpiperidine |
| 21 | CH₂CH₃ | CN | 3-hydroxy-3-methyl-1-methylazetidine |
| 22 | CH₂CH₃ | CN | 4-(2-hydroxypropan-2-yl)piperidine |
| 23 | CH₂CH₃ | CN | 1-(1-methylpiperidin-4-yl)ethanol (*) |
| 24 | CH₂CH₃ | CN | 1-(1-methylpiperidin-4-yl)ethanol (*) |

TABLE 7

[Structure: Imidazopyridine-pyrimidine-phenyl-C(R3)(R4)OH scaffold with R1, R5 substituents, S-configuration]

| Example | R1 | R5 | (R3/R4 group) |
|---|---|---|---|
| 25 | CH₂CH₃ | CN | 1-[1-(2-methoxyethyl)piperidin-4-yl]ethanol |
| 26 | CH₂CH₃ | CN | 1-(1-isopropylpiperidin-4-yl)ethanol (*) |
| 27 | CH₂CH₃ | CN | 1-(1-isopropylpiperidin-4-yl)ethanol (*) |
| 28 | CH₂CH₃ | CN | 1-(1-cyclopentylpiperidin-4-yl)ethanol |

TABLE 7-continued

Core structure: R1-substituted imidazopyridine linked to pyrimidine (with R5) and NH-C*(S)(CH3)-phenyl-C(R3)(R4)-OH

| Example | R1 | R5 | (substituent at phenyl) |
|---|---|---|---|
| 29 | CH2CH3 | CN | 4-(1-hydroxyethyl)piperidin-1-yl-CH2-C(CH3)3 (neopentyl) |
| 30 | CH2CH3 | CN | 1-ethyl-4-(1-hydroxyethyl)piperidine (*) |
| 31 | CH2CH3 | CN | 1-ethyl-4-(1-hydroxyethyl)piperidine (*) |
| 32 | CH2CH3 | CN | 1-propyl-4-(1-hydroxyethyl)piperidine |

TABLE 8

Core structure: R1,R2-disubstituted imidazopyridine linked to pyrimidine (with R5) and NH-C*(S)(CH3)-phenyl-C(R3)(R4)-OH

| Example | R1 | R2 | R5 | (substituent) |
|---|---|---|---|---|
| 33 | CH2CH3 | Br | CN | 1-isopropyl-4-(1-hydroxyethyl)piperidine |
| 34 | CH3 | H | CN | 1-methyl-4-(1-hydroxyethyl)-1,2,3,6-tetrahydropyridine |
| 35 | Cl | H | CN | 1-methyl-4-(1-hydroxyethyl)piperidine |
| 36 | cyclopropyl | H | CN | 1-methyl-4-(1-hydroxyethyl)piperidine |
| 37 | Cl | H | CN | 1-cyclopropyl-4-(1-hydroxyethyl)piperidine |
| 38 | Cl | H | CN | 1-(2-(methylsulfonyl)ethyl)-4-(1-hydroxyethyl)piperidine |

TABLE 8-continued
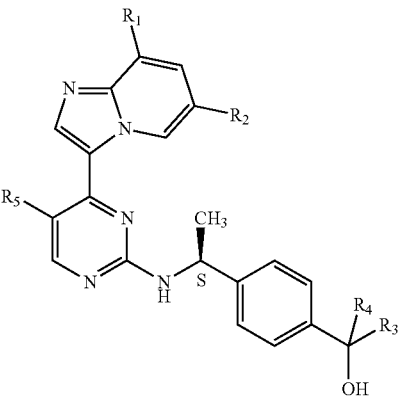
| Example | $R_1$ | $R_2$ | $R_5$ | |
|---|---|---|---|---|
| 39 | $CHF_2$ | H | CN | 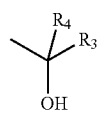 |
| 40 | Cl | H | CN | 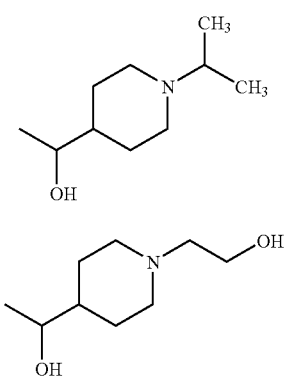 |
TABLE 9
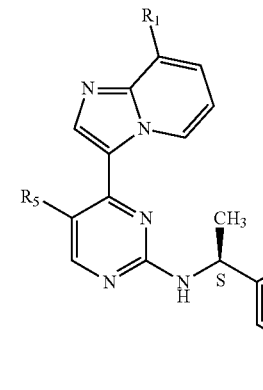
| Example | $R_1$ | $R_5$ | |
|---|---|---|---|
| 41 | $CH_2CH_3$ | CN | 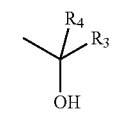 |
TABLE 9-continued
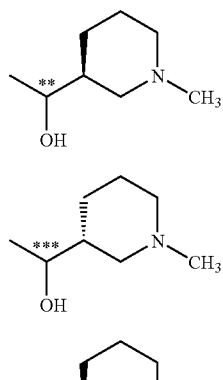
| Example | $R_1$ | $R_5$ | |
|---|---|---|---|
| 42 | $CH_2CH_3$ | CN | 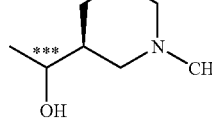 |
| 43 | $CH_2CH_3$ | CN | 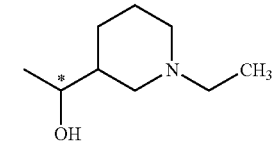 |
| 44 | $CH_2CH_3$ | CN | 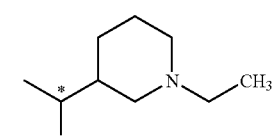 |
| 45 | $CH_2CH_3$ | CN | 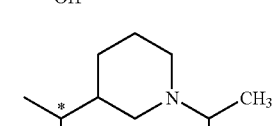 |
| 46 | $CH_2CH_3$ | CN | 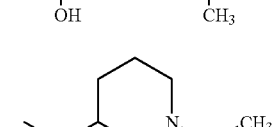 |
| 47 | $CH_2CH_3$ | CN | 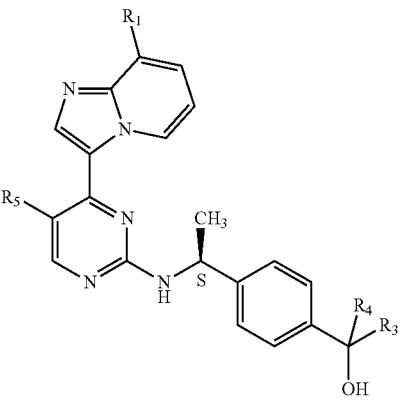 |
| 48 | $CH_2CH_3$ | CN | 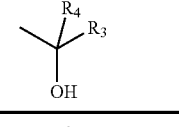 |

TABLE 10

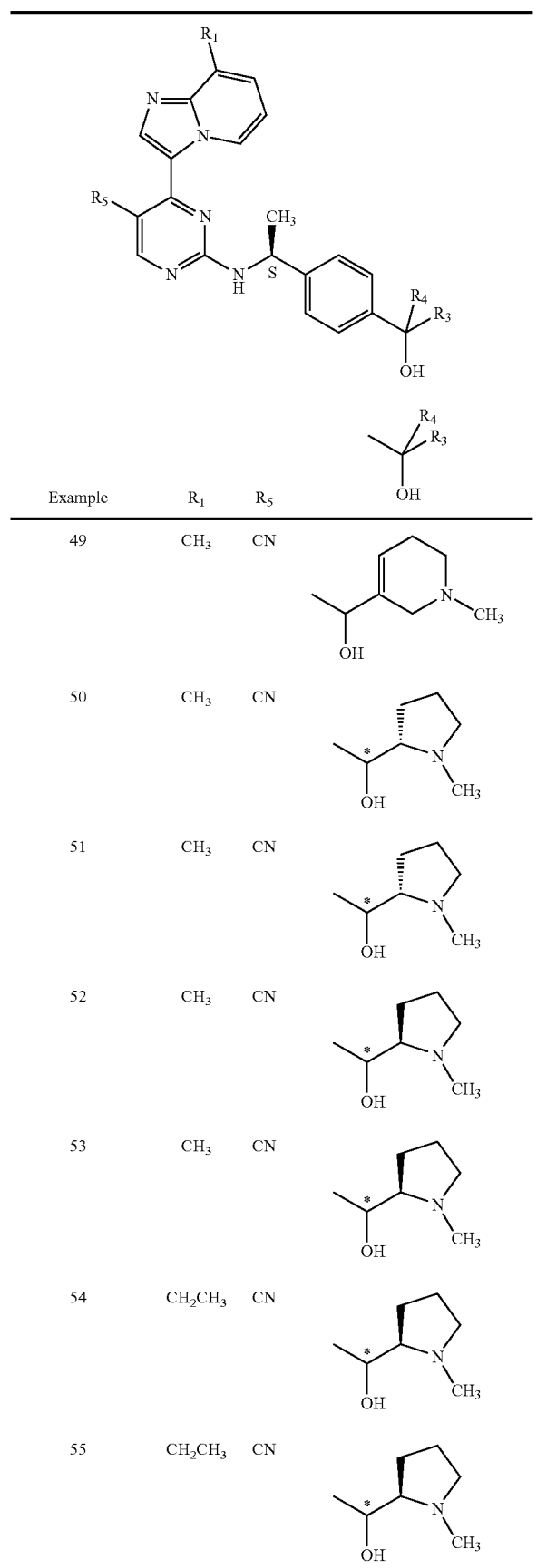

| Example | R₁ | R₅ | (R₃/R₄ group) |
|---|---|---|---|
| 49 | CH₃ | CN | 1-methyl-1,2,3,6-tetrahydropyridin-3-yl ethanol |
| 50 | CH₃ | CN | 1-(1-methylpyrrolidin-2-yl)ethanol |
| 51 | CH₃ | CN | 1-(1-methylpyrrolidin-2-yl)ethanol |
| 52 | CH₃ | CN | 1-(1-methylpyrrolidin-2-yl)ethanol |
| 53 | CH₃ | CN | 1-(1-methylpyrrolidin-2-yl)ethanol |
| 54 | CH₂CH₃ | CN | 1-(1-methylpyrrolidin-2-yl)ethanol |
| 55 | CH₂CH₃ | CN | 1-(1-methylpyrrolidin-2-yl)ethanol |

TABLE 10-continued

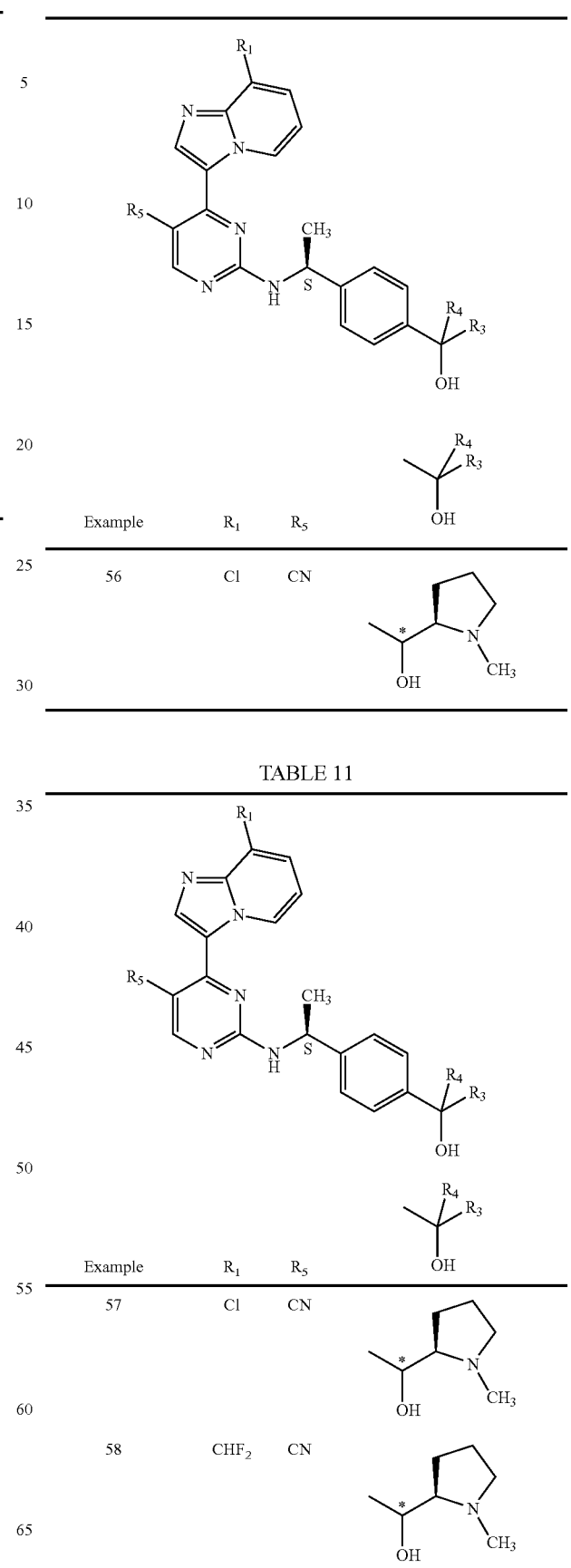

| Example | R₁ | R₅ | (R₃/R₄ group) |
|---|---|---|---|
| 56 | Cl | CN | 1-(1-methylpyrrolidin-2-yl)ethanol |

TABLE 11

| Example | R₁ | R₅ | (R₃/R₄ group) |
|---|---|---|---|
| 57 | Cl | CN | 1-(1-methylpyrrolidin-2-yl)ethanol |
| 58 | CHF₂ | CN | 1-(1-methylpyrrolidin-2-yl)ethanol |

TABLE 11-continued
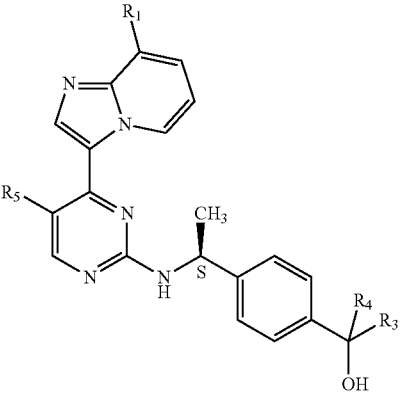
| Example | R₁ | R₅ | (R₃/R₄/OH group) |
|---|---|---|---|
| 59 | CHF₂ | CN | 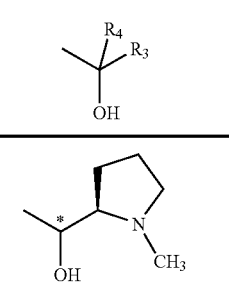 |
| 60 | CHF₂ | CN | 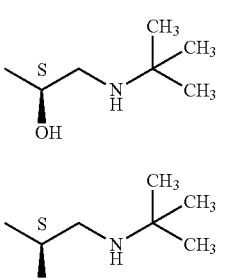 |
| 61 | Cl | CN |  |
| 62 | cyclopropyl | CN | 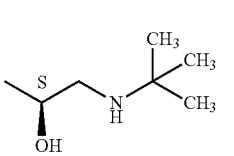 |
TABLE 12
| Example | R₁ | R₅ | (R₃/R₄/OH group) |
|---|---|---|---|
| 63 | cyclopropyl | CN |  |
| 64 | cyclopropyl | CN | 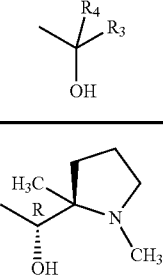 |
TABLE 12-continued
| Example | R₁ | R₅ | (R₃/R₄/OH group) |
|---|---|---|---|
| 65 | cyclopropyl | CN |  |
| 66 | cyclopropyl | CN | 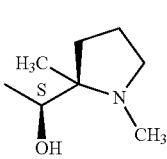 |
| 67 | Cl | F |  |
| 68 | Cl | F | 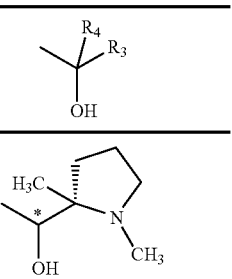 |
| 69 | Cl | F |  |
| 70 | Cl | F | 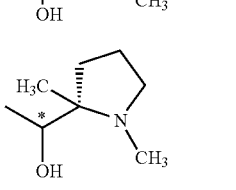 |

TABLE 13

| Example | R₁ | R₅ | R₃R₄C(OH)- group |
|---|---|---|---|
| 71 | Cl | F | (S)-1-((1-methylcyclopentyl)amino)propan-2-ol substituent |
| 72 | Cl | F | (S)-1-((1-(hydroxymethyl)cyclopentyl)amino)propan-2-ol substituent |
| 73 | cyclopropyl | CH₃ | (S)-1-(tert-butylamino)propan-2-ol substituent |
| 74 | Cl | CH₃ | (S)-1-(tert-butylamino)propan-2-ol substituent |
| 75 | Cl | H | (S)-1-(tert-butylamino)propan-2-ol substituent |
| 76 | cyclopropyl | H | (S)-1-(tert-butylamino)propan-2-ol substituent |
| 77 | cyclopropyl | Cl | (S)-1-(tert-butylamino)propan-2-ol substituent |

TABLE 13-continued

| Example | R₁ | R₅ | R₃R₄C(OH)- group |
|---|---|---|---|
| 78 | Cl | Cl | (S)-1-(tert-butylamino)propan-2-ol substituent |

TABLE 14

| Example | R₁ | R₅ | R₃R₄C(OH)- group |
|---|---|---|---|
| 79 | cyclopropyl | F | (S)-1-(tert-butylamino)propan-2-ol substituent |
| 80 | H | F | (S)-1-(tert-butylamino)propan-2-ol substituent |

TABLE 14-continued

| Example | R₁ | R₅ | (substituent) |
|---|---|---|---|
| 81 | CF₃ | F | (S)-CH(CH₃)CH₂NH-C(CH₃)₃ with OH |
| 82 | Cl | F | (R)-2-methyl-2-(1-hydroxyethyl)-1-methylpyrrolidine |
| 83 | Cl | F | 2-(1-hydroxyethyl)-1-methylpyrrolidine (*) |
| 84 | Cl | F | CH(OH)C(CH₃)₂N(CH₃)₂ (*) |
| 85 | Cl | F | CH(OH)C(CH₃)₂N(CH₃)₂ (*) |
| 86 | Cl | F | CH(OH)C(CH₃)₂NHCH₃ |

TABLE 15

| Example | R₁ | R₅ | (substituent) |
|---|---|---|---|
| 87 | Cl | F | 1-(tert-butyl)-4-(1-hydroxyethyl)piperidine |
| 88 | Cl | F | 1-isopropyl-3-(1-hydroxyethyl)azetidine (*) |
| 89 | Cl | F | 1-isopropyl-3-(1-hydroxyethyl)azetidine (*) |
| 90 | Cl | F | 1-isopropyl-4-(1-hydroxyethyl)piperidine (*) |

TABLE 15-continued

| Example | R₁ | R₅ | (substituent) |
|---|---|---|---|
| 91 | Cl | F | 4-(1-isopropylpiperidinyl) with OH, * chiral |
| 92 | Cl | F | 1-(tert-butyl)azetidin-3-yl ethanol |
| 93 | CHF₂ | F | (S)-1-((tert-butylamino)methyl)-2-hydroxy |

Example 1

Synthesis of 2-[((1S)-1-{4-[2-(dimethylamino)-1-hydroxyethyl]phenyl}ethyl)amino]-4-(8-methylimidazo[1,2-a]pyridin-3-yl)pyrimidine-5-carbonitrile [1] (hereinafter, referred to as the compound [1])

(1) 2 g of (S)-(−)-1-(4-bromophenyl)ethylamine was dissolved in 20 mL of chloroform, and 4.18 mL of triethylamine was added. Thereto, 2.62 g of di-tert-butyl dicarbonate was added under an ice-cold condition, and the mixture was stirred for 30 minutes at room temperature. The reaction solution was diluted in 300 mL of ethyl acetate and washed with water and saturated brine in that order, and the resulting organic layer was dried over anhydrous magnesium sulfate. The insolubles were filtered, the filtrate was concentrated under reduced pressure, and the resulting residue was dissolved in a small amount of chloroform and solidified with hexane, to obtain 2.6 g of tert-butyl[(1S)-1-(4-bromophenyl)ethyl]carbamate [1-1] (hereinafter, referred to as the compound [1-1]) as a white solid.

(2) A mixture of 600 mg of the compound [1-1], 75 mg of dichlorobis(triphenylphosphine)palladium (II), 743 μL of tributyl (1-ethoxyvinyl)tin, and 3 mL of 1,4-dioxane, was stirred overnight at 100° C. After standing to cool, the insolubles were filtered and the filtrate was concentrated under reduced pressure. The resulting residue was purified by silica gel column chromatography (eluent: hexane/ethyl acetate=8/2) to obtain 367 mg of tert-butyl[(1S)-1-(4-acetylphenyl)ethyl]carbamate [1-2] (hereinafter, referred to as the compound [1-2]) as a colorless solid.

(3) 984 mg of benzyl tributyl ammonium bromide was dissolved in a mixed solvent of 3 mL of chloroform and 2 mL of methanol, and then 141 μL of bromine was added. Thereto, a solution prepared by dissolving 363 mg of the compound [1-2] in a mixed solvent of 4 mL of chloroform and 0.8 mL of methanol was added. The reaction mixture was stirred for 30 minutes at 40° C. After standing to cool, water was added to the reaction solution, which was extracted with chloroform. The organic layer was washed with saturated brine, and dried over anhydrous sodium sulfate. The insolubles were filtered, the filtrate was concentrated under reduced pressure, and the resulting residue was purified by silica gel column chromatography (eluent: hexane/ethyl acetate=7/3), to obtain 170 mg of tert-butyl{(1S)-1-[4-(bromoacetyl)phenyl]ethyl} carbamate [1-3] (hereinafter, referred to as the compound [1-3]) as a colorless oily product.

(4) 50 mg of the compound [1-3] was dissolved in 0.5 mL of N,N-dimethylformamide, and 365 μL of dimethylamine (2.0 M tetrahydrofuran solution) was added thereto. The mixture was stirred overnight at room temperature, and then to the reaction solution was added a saturated aqueous solution of sodium hydrogen carbonate, and the solution was extracted with ethyl acetate. The organic layer was washed with saturated brine and dried over anhydrous sodium sulfate. The insolubles were filtered, the filtrate was concentrated under reduced pressure, and the resulting residue was purified by preparative thin-layer chromatography, to obtain 26.3 mg of tert-butyl {(1S)-1-[4-(N,N-dimethylglycyl)phenyl]ethyl}carbamate [1-4] (hereinafter, referred to as the compound [1-4]) as a colorless oily product.

(5) 26.3 mg of the compound [1-4] was dissolved in 1.5 mL of methanol, 16.2 mg of sodium boronhydride was added thereto, and the mixture was stirred for 30 minutes at room temperature. To the reaction solution was added a saturated aqueous solution of sodium hydrogen carbonate, and the solution was extracted with a mixed solvent of chloroform and methanol (mixing ratio: 9/1). The organic layer was washed with saturated brine and dried over anhydrous sodium sulfate. The insolubles were filtered, and the filtrate was concentrated under reduced pressure, to obtain tert-butyl((1S)-1-{4-[2-(dimethylamino)-1-hydroxyethyl]phenyl}ethyl)carbamate [1-5] (hereinafter, referred to as the compound [1-5]). The compound [1-5] was used in the subsequent reaction without further purification.

(6) 10 g of 4-[(Z)-2-ethoxyvinyl]-2-(methylthio)-5-pyrimidinecarbonitrile (synthesized according to the method disclosed in International Publication WO2006/025567, pages 90-91) was dissolved in a mixed solvent of 150 mL of 1,4-dioxane and 30 mL of water and then 8.04 g of N-bromosuccinimide was added thereto under an ice-cold condition, and the mixture was stirred for 1.5 hours at room temperature. To the reaction solution, 4.89 g of 2-amino-3-picoline was added, and the mixture was further stirred for 2.5 hours. 200 mL of water was added to the reaction solution to extract with 2 L of a mixed solvent of chloroform and methanol (mixing ratio: 9/1). The organic layer was washed with water, and dried over anhydrous magnesium sulfate. Thereafter, the insolubles were filtered, and the filtrate was concentrated under reduced pressure. The resulting residue was dissolved in a small amount of chloroform and solidified with hexane to obtain 4.02 g of 4-(8-methylimidazo[1,2-a]pyridin-3-yl)-2-(methylthio)pyrimidine-5-carbonitrile [1-6] (hereinafter, referred to as the compound [1-6]) as a light brown solid.

(7) 20.1 mg of the compound [1-6] was dissolved in 1.5 mL of chloroform and then 24.7 mg of m-chloroperbenzoic acid was added thereto under an ice-cold condition, and the mixture was stirred for 30 minutes at 0° C. To the reaction solution was added a saturated aqueous solution of sodium hydrogen carbonate was added, and the solution was extracted with chloroform. The resulting organic layer was washed with saturated brine, and then dried over anhydrous sodium sulfate. The insolubles were filtered and the filtrate was concentrated under reduced pressure to obtain the oxidized form of the compound [1-6]. In a separate flask, the compound [1-5] was dissolved in 1.5 mL of chloroform, and 1.5 mL of trifluoroacetic acid was added thereto. The mixture was stirred for 1 hour at room temperature. The reaction solution was concentrated under reduced pressure, and the resulting residue was dissolved in methanol, which was passed through a weak anion exchange resin (Bond Elut Regular type PSA, GL Sciences Inc.) to remove the trifluoroacetic acid, and the solvent was distilled off under reduced pressure. The resulting residue was dissolved in 0.5 mL of tetrahydrofuran, and to the resultant solution was added a solution prepared by mixing 9.9 µL of triethylamine and the previously obtained oxidized form in 1 mL of chloroform, and the solution was stirred for 3 hours at room temperature. To the reaction solution was added a saturated aqueous solution of sodium hydrogen carbonate, and the solution was extracted with chloroform. The resulting organic layer was washed with saturated brine, and then dried over anhydrous sodium sulfate. The insolubles were filtered, the filtrate was concentrated under reduced pressure, and then purified by preparative thin-layer chromatography (developing solvent: chloroform/methanol=20/1), to obtain 14.5 mg of the title compound [1] as a yellow solid.

The spectral data of the compound [1] are presented below.
$^1$H-NMR (CDCl$_3$) δ: 9.64-9.62 (m, 1H×1/5), 8.95-8.74 (m, 1H+1H×4/5), 8.56 (s, 1H×1/5), 8.53 (s, 1H×4/5), 7.43-7.15 (m, 5H), 6.64-6.63 (m, 1H), 6.02-6.01 (m, 1H×4/5), 5.85-5.76 (m, 1H×1/5), 5.42-5.33 (m, 1H+1H×1/5), 5.16-5.12 (m, 1H×4/5), 4.74-4.69 (m, 1H), 2.69 (s, 1H×3/5), 2.64 (s, 2H+1H×2/5), 2.36 (s, 3H), 2.03-1.80 (m, 2H), 1.63 (d, J=6.8 Hz, 3H)
mass: 442 (M+1)$^+$.

Example 2

Synthesis of 2-[((1S)-1-{4-[1-hydroxy-2-(methylamino)ethyl]phenyl}ethyl)amino]-4-(8-methylimidazo[1,2-a]pyridin-3-yl)pyrimidine-5-carbonitrile [2] (hereinafter, referred to as the compound [2])

(1) 1.01 g of Z-SAR-OH (available from Kokusan Chemical Co., Ltd.), 4.72 mL of diisopropylethylamine, 1.83 g of 1-hydroxybenzotriazole monohydrate, and 1.32 g of N,O-dimethyl hydroxylamine hydrochloride were dissolved in 15 mL of N,N-dimethylformamide, then 2.6 g of 1-ethyl-3-(3-dimethylaminopropyl)carbodiimide hydrochloride was added thereto under an ice-cold condition, and the mixture was stirred for 2.5 hours at room temperature. To the reaction solution was added a saturated aqueous solution of sodium hydrogen carbonate, and the solution was extracted with ethyl acetate. The resulting organic layer was washed with saturated brine, and then dried over anhydrous sodium sulfate. The insolubles were filtered, the filtrate was concentrated under reduced pressure, and the resulting residue was purified by silica gel column chromatography (eluent: hexane/ethyl acetate=1/1), to obtain 1.02 g of benzyl{2-[methoxy(methyl)amino]-2-oxoethyl}methylcarbamate [2-1] (hereinafter, referred to as the compound [2-1]) as a pale yellow oily product.

(2) 200 mg of the compound [1-1] was dissolved in 4 mL of tetrahydrofuran, and the mixture was cooled to −78° C. and then 626 µL of n-butyllithium (2.66 M hexane solution) was added thereto. After a 1 hour stirring at the same temperature, 0.6 mL of tetrahydrofuran solution containing 177 mg of the compound [2-1] was added thereto, and the mixture was further stirred for 2 hours. To the reaction mixture was added a saturated aqueous solution of sodium hydrogen carbonate, and the mixture was extracted with ethyl acetate. The resulting organic layer was washed with saturated brine and dried over anhydrous sodium sulfate. The insolubles were filtered, the filtrate was concentrated under reduced pressure, and the resulting residue was purified by silica gel column chromatography (eluent: hexane/ethyl acetate=6/4), to obtain 36.2 mg of benzyl[2-(4-{(1S)-1-[(tert-butoxycarbonyl)amino]ethyl}phenyl)-2-oxoethyl]methylcarbamate [2-2] (hereinafter, referred to as the compound [2-2]) as a colorless oily product.

(3) 159 mg of the compound [2-2] was dissolved in a mixed solvent of 4 mL of tetrahydrofuran and 2 mL of methanol, then 48 mg of 10% palladium carbon catalyst was added thereto, and the mixture was further stirred for 2 hours under hydrogen atmosphere. Thereto, 95 mg of 10% palladium carbon catalyst was further added and stirred for 3.5 hours under hydrogen atmosphere. The insolubles were filtered through celite and the filtrate was concentrated under reduced pressure, to obtain tert-butyl{(1S)-1-[4-(N-methylglycyl)phenyl]ethyl}carbamate [2-3] (hereinafter, referred to as the compound [2-3]) as crude and purified products. The compound [2-3] was used in the subsequent reaction without further purification.

(4) The compound [2-3] was dissolved in 3 mL of chloroform, and 76 µL of benzaldehyde and 158 mg of sodium triacetoxyborohydride were added thereto. After an overnight stirring at room temperature, to the mixture was added a saturated aqueous solution of sodium hydrogen carbonate, and the mixture was extracted with a mixed solvent of chloroform and methanol (mixing ratio: 9/1). The resulting organic layer was washed with saturated brine, and then dried over anhydrous sodium sulfate. The insolubles were filtered, the filtrate was concentrated under reduced pressure, and then the resulting residue was purified by preparative thin-layer chromatography, to obtain 64 mg of tert-butyl{(1S)-1-[4-(N-benzyl-N-methylglycyl)phenyl]ethyl}carbamate [24] (hereinafter, referred to as the compound [2-4]) as a colorless oily product.

(5) 36 mg of 2-{[(1S)-1-(4-{2-[benzyl(methyl)amino]-1-hydroxyethyl}phenyl)ethyl]amino}-4-(8-methylimidazo[1,2-a]pyridin-3-yl)pyrimidine-5-carbonitrile [2-5] (hereinafter, referred to as the compound [2-5]) was obtained as a yellow oily product from 39 mg of the compound [1-6] and 64 mg of the compound [24] according to the method of Example 1-(7).

(6) 18 mg of the compound [2-5] was dissolved in a mixed solvent of 1 mL of tetrahydrofuran and 0.5 mL of methanol, and then 18 mg of a carbon catalyst of 20% palladium hydroxide was added thereto. After the 4 hours stirring under hydrogen atmosphere, the insolubles were filtered through celite and the filtrate was concentrated under reduced pressure. The obtained residue was purified by preparative thin-layer chromatography to obtain 6 mg of the title compound [2] as a pale yellow solid.

The spectral data of the compound [2] are presented below.
$^1$H-NMR (CDCl$_3$) δ: 9.74-9.73 (m, 1H×1/5), 8.88-8.80 (m, 1H+1H×4/5), 8.54 (s, 1H×1/5), 8.52 (s, 1H×4/5), 7.43-6.80 (m, 5H), 6.70-6.65 (m, 1H), 5.32-5.30 (m, 1H+1H×1/5), 5.15-5.10 (m, 1H×4/5), 4.82-4.79 (m, 1H), 2.80-2.76 (m, 2H), 2.66 (s, 1H×3/5), 2.62 (s, 2H+1H×2/5), 2.49 (s, 1H×3/5), 2.46 (s, 2H+1H×2/5), 1.62 (d, J=6.8 Hz, 3H), 1.27 (brs, 1H)
mass: 428 (M+1)$^+$.

Example 3

Synthesis of 2-({(1S)-1-[4-(1-hydroxy-2-pyrrolidin-1-ylethyl)phenyl]ethyl}amino)-4-(8-methylimidazo[1,2-a]pyridin-3-yl)pyrimidine-5-carbonitrile [3] (hereinafter, referred to as the compound [3])

(1) 300 mg of the compound [1-6] was dissolved in 6 mL of chloroform, and 368 mg of m-chloroperbenzoic acid was added thereto under an ice-cold condition. After the 30 minutes stirring at the same temperature, to the reaction mixture was added a saturated aqueous solution of sodium hydrogen carbonate, and the mixture was extracted with chloroform. The resulting organic layer was dried over anhydrous sodium sulfate, then the insolubles were filtered, and the filtrate was concentrated under reduced pressure. The resulting residue was dissolved in 3 mL of chloroform, poured onto 3 mL of a tetrahydrofuran solution containing 257 mg of S-(−)-1-(4-bromophenyl)ethylamine and 224 μL of triethylamine, and the mixture was stirred overnight at room temperature. To the reaction mixture was added a saturated aqueous solution of sodium hydrogen carbonate, and the mixture was extracted with chloroform. The obtained organic layer was washed with saturated brine and dried over anhydrous sodium sulfate. The insolubles were filtered, the filtrate was concentrated under reduced pressure, and then the obtained residue was purified by silica gel column chromatography (eluent: chloroform/methanol=20/1), to obtain 252 mg of 2-{[(1S)-1-(4-bromophenyl)ethyl]amino})-4-(8-methylimidazo[1,2-a]pyridin-3-yl)pyrimidine-5-carbonitrile [3-1] (hereinafter, referred to as the compound [3-1]) as a pale yellow oily product.

(2) A mixture of 252 mg of the compound [3-1], 20 mg of dichlorobis(triphenylphosphine) palladium (II), 216 μL of tributyl (1-ethoxyvinyl)tin, and 3.5 mL of 1,4-dioxane, was stirred overnight at 100° C. The reaction mixture was concentrated under reduced pressure, and then the residue was dissolved in a mixed solvent of 3 mL of tetrahydrofuran and 1 mL of water. Thereto, 135 mg of N-bromosuccinimide was added, and the mixture was stirred for 30 minutes at room temperature. To the reaction mixture was added a saturated aqueous solution of sodium hydrogen carbonate, and the mixture was extracted with chloroform. The resulting organic layer was washed with saturated brine and dried over anhydrous sodium sulfate. The insolubles were filtered, the filtrate was concentrated under reduced pressure, and then the obtained residue was purified by silica gel column chromatography (eluent: hexane/chloroform/ethyl acetate=3/2/5), to obtain 160 mg of 2-({(1S)-1-[4-(bromoacetyl)phenyl]ethyl}amino)-4-(8-methylimidazo[1,2-a]pyridin-3-yl)pyrimidine-5-carbonitrile [3-2] (hereinafter, referred to as the compound [3-2]) as a yellow solid.

(3) 20 mg of the compound [3-2] was dissolved in 0.4 mL of N,N-dimethylformamide, and 7 μL of pyrrolidine was added thereto. The reaction mixture was stirred for 30 minutes at room temperature, and then thereto was added a saturated aqueous solution of sodium hydrogen carbonate, and the mixture was extracted with chloroform. The resulting organic layer was washed with saturated brine, and dried over anhydrous sodium sulfate. The insolubles were filtered, the filtrate was concentrated under reduced pressure, and the resulting residue was purified by preparative thin-layer chromatography, to obtain 3 mg of 4-(8-methylimidazo[1,2-a]pyridin-3-yl)-2-({(1S)-1-[4-(pyrrolidin-1-ylacetyl) phenyl]ethyl}amino)pyrimidine-5-carbonitrile [3-3] (hereinafter, referred to as the compound [3-3]) as a colorless oily product.

(4) 3 mg of the compound [3-3] was dissolved in a mixed solvent of 0.4 mL of tetrahydrofuran and 0.4 mL of methanol, and 9 mg of a carbon catalyst of 20% palladium hydroxide was added thereto. The mixture was stirred for 2 hours at room temperature under hydrogen atmosphere, and the catalyst was filtered through celite. The filtrate was concentrated under reduced pressure and the resulting residue was purified by preparative thin-layer chromatography to obtain 1.5 mg of the title compound [3] as a colorless solid.

The spectral data of the compound [3] are presented below.
$^1$H-NMR (CDCl$_3$) δ: 9.66-9.56 (m, 1H×1/5), 8.95-8.74 (m, 1H+1H×4/5), 8.56 (s, 1H×1/5), 8.52 (s, 1H×4/5), 7.45-7.16 (m, 5H), 6.65-6.64 (m, 1H), 6.08-6.00 (m, 1H×4/5), 5.88-5.80 (m, 1H×1/5), 5.36-5.28 (m, 1H+1H×1/5), 5.13-5.12 (m, 1H×4/5), 4.88-4.86 (m, 1H), 2.92-2.62 (m, 4H), 2.69 (s, 1H×3/5), 2.64 (s, 2H+1H×2/5), 2.15-1.70 (m, 6H), 1.62 (d, J=6.8 Hz, 3H)
mass: 468 (M+1)$^+$.

Example 4

Synthesis of 2-[((1S)-1-{4-[2-(tert-butylamino)-1-hydroxyethyl]phenyl}ethyl)amino]-4-(8-methylimidazo[1,2-a]pyridin-3-yl)pyrimidine-5-carbonitrile [4] (hereinafter, referred to as the compound [4])

2.8 mg of the title compound [4] was obtained as colorless solid from 40 mg of the compound [3-2] and 15.3 μL of N-tert-butylbenzylamine according to the methods of Example 3-(3) and (4).

The spectral data of the compound [4] are presented below.
$^1$H-NMR (CDCl$_3$) δ: 9.65-9.63 (m, 1H×1/5), 8.94-8.72 (m, 1H+1H×4/5), 8.56-8.51 (m, 1H), 7.45-6.94 (m, 5H), 6.67-6.64 (m, 1H), 6.31-6.27 (m, 11H×4/5), 6.00-5.93 (m, 1H×1/5), 5.34-5.25 (m, 1H×1/5), 5.14-5.10 (m, 1H×4/5), 5.04-5.01 (m, 11H), 3.20-2.76 (m, 2H), 2.68 (s, 1H×3/5), 2.62 (s, 2H+1H×2/5), 1.64-1.59 (m, 3H), 1.27 (s, 4H+1H×1/2), 1.25 (s, 4H+1H×1/2)
mass: 470 (M+1)$^+$.

Example 5

Synthesis of 2-[((1S)-1-{4-[(1S)-2-(tert-butylamino)-1-hydroxyethyl]phenyl}ethyl)amino]-4-(8-ethylimidazo[1,2-a]pyridin-3-yl)pyrimidine-5-carbonitrile [5] (hereinafter, referred to as the compound [5])

(1) A mixture of 1.0 g of the compound [1-1], 892 mg of potassium vinyltrifluoroborate, 468 mg of dichlorobis(triphenylphosphine) palladium (II), 10 mL of 2.0M aqueous sodium carbonate solution, and 20 mL of N,N-dimethylformamide, was stirred overnight at 90° C. After standing to cool, water was added to the reaction solution, which was extracted with ethyl acetate. The resulting organic layer was washed with saturated brine and dried over anhydrous sodium sulfate. The insolubles were filtered, the filtrate was concentrated under reduced pressure, and the resulting residue was purified by silica gel column chromatography (eluent: hexane/ethyl acetate=100/0-75/25), to obtain 485 mg of tert-butyl[(1S)-1-(4-vinylphenyl)ethyl]carbamate [5-1] (hereinafter, referred to as the compound [5-1]) as a white solid.

(2) 25.3 g of AD-mix-alpha (available from Aldrich Corporation) was added to a mixed solvent of 110 mL of tert-butanol and 110 mL of water to prepare a suspension. Thereto, 4.34 g of the compound [5-1] was added under an ice-cold condition, and the mixture was stirred for 24 hours at the same temperature. 25 g of sodium sulfite was added to the reaction solution, which was stirred for 30 minutes at 0° C., and then extracted with chloroform. The resulting organic layer was dried over anhydrous sodium sulfate. The insolubles were filtered, the filtrate was concentrated under reduced pressure, and the resulting residue was purified by silica gel column chromatography (eluent: chloroform/methanol=100/0-90/10), to obtain 4.32 g of tert-butyl ((1S)-1-{4-[(1S)-1,2-dihydroxyethyl]phenyl}ethyl)carbamate [5-2] (hereinafter, referred to as the compound [5-2]) as a white solid.

(3) 4.32 g of the compound [5-2] was dissolved in 50 mL of pyridine, and 3.66 g of p-toluenesulfonyl chloride was added thereto under an ice-cold condition. The reaction mixture was stirred overnight at 0° C., water was added thereto, and then the mixture was extracted with ethyl acetate, and the resulting organic layer was dried over anhydrous sodium sulfate. The insolubles were filtered, the filtrate was concentrated under reduced pressure, and then the obtained residue was purified by silica gel column chromatography (eluent:hexane/ethyl acetate=50/50-0/100), to obtain 6.52 g of (2S)-2-(4-{(1S)-1-[(tert-butoxycarbonyl)amino]ethyl}phenyl)-2-hydroxyethyl 4-methylbenzenesulfonate [5-3] (hereinafter, referred to as the compound [5-3]) as a colorless amorphous.

(4) 6.52 g of the compound [5-3] was dissolved in 44.4 mL of chloroform, a solution prepared by dissolving 2.4 g of sodium hydroxide in 5.54 mL of water was added, and 203 mg of tetrabutylammonium hydrogen sulfate was added thereto. The reaction mixture was stirred overnight at room temperature, water was added thereto, and the mixture was extracted with ethyl acetate. The obtained organic layer was washed with saturated brine and dried over anhydrous sodium sulfate. The insolubles were filtered, the filtrate was concentrated under reduced pressure, and the resulting residue was purified by silica gel column chromatography (eluent: 50% chloroform-hexane/ethyl acetate=100/0-75/25), to obtain 4.4. g of tert-butyl((1S)-1-{4-[(2S)-oxiran-2-yl]phenyl}ethyl)carbamate [5-4] (hereinafter, referred to as the compound [54]) as a white solid.

(5) 4.4 g of the compound [5-4] was dissolved in 40 mL of ethanol, 20 mL of tert-butylamine was added thereto, and the mixture was stirred for 3 days at 50° C. The reaction solution was concentrated, and the resulting residue was purified by silica gel column chromatography (eluent: hexane/ethyl acetate=100/0-0/100), to obtain 3.1 g of tert-butyl ((1S)-1-{4-[(1S)-2-(tert-butylamino)-1-hydroxyethyl]phenyl}ethyl)carbamate [5-5] (hereinafter, referred to as the compound [5-5]) as a white solid.

(6) 4.89 g of 4-[(Z)-2-ethoxyvinyl]-2-(methylthio)-5-pyrimidinecarbonitrile (synthesized according to the method disclosed in International Publication WO2006/025567, page 90 to 91) was dissolved in a mixed solvent of 50 mL of 1,4-dioxane and 5 mL of water, then 3.93 g of N-bromosuccinimide was added under an ice-cold condition, and the mixture was stirred for 1 hour at room temperature. To the reaction solution was added 2.7 g of 3-ethylpyridine-2-amine (synthesized according to the method disclosed in International Publication WO2006/025567, page 142), and the solution was stirred overnight at room temperature. To the reaction solution was added a saturated aqueous solution of sodium hydrogen carbonate, the solution was extracted with chloroform, and the resulting organic layer was dried over anhydrous sodium sulfate. The insolubles were filtered, and the filtrate was concentrated under reduced pressure. Diethylether was added to the resulting residue, and the resultant solution was stirred for 3 hours. Thus produced solid was taken by filtration and dried under reduced pressure to obtain 4.46 g of 4-(8-ethylimidazo[1,2-a]pyridin-3-yl)-2-(methylthio)pyrimidine-5-carbonitrile [5-6] (hereinafter, referred to as the compound [5-6]) as a pale yellow solid.

(7) 2 g of the compound [5-6] was dissolved in 150 mL of chloroform, and 1.95 g of m-chloroperbenzoic acid was added thereto under an ice-cold condition. The mixture was stirred for 30 minutes at 0° C. To the reaction solution was added a saturated aqueous solution of sodium hydrogen carbonate, and the solution was extracted with chloroform. The obtained organic layer was washed with saturated brine, and then dried over anhydrous sodium sulfate. The insolubles were filtered and the filtrate was concentrated under reduced pressure, to obtain an oxidized form of the compound [5-6]. In a separate flask, the compound [5-5] was dissolved in 20 mL of chloroform, and 10 mL of trifluoroacetic acid was added thereto under an ice-cold condition. The reaction solution was stirred for 1 hour at room temperature. The reaction solution was concentrated under reduced pressure, the resulting residue was dissolved in 20 mL of tetrahydrofuran, and a solution prepared by mixing 25 mL of triethylamine and the previously obtained oxidized form in 20 mL of chloroform was added thereto, and the mixture was stirred for 1 hour at room temperature. To the reaction solution was added a saturated aqueous solution of sodium hydrogen carbonate, and the solution was extracted with a mixed solvent of chloroform and methanol (mixing ratio: 9/1). The obtained organic layer was washed with water and then washed with anhydrous sodium sulfate. The insolubles were filtered, the filtrate was concentrated under reduced pressure, and the resulting residue was purified by silica gel column chromatography (eluent: chloroform/methanol=100/0-90/10), to obtain 1.2 g of the title compound [5] as a pale yellow solid. 803 mg of the compound [5] was suspended in 20 mL of ethanol, and 1.66 mL of a 1N aqueous hydrochloric acid solution was added thereto, to give a homogeneous solution. The mixture was concentrated under reduced pressure, and 20 mL of ethanol was added to the resulting residue, and the resultant solution was re-concentrated under reduced pressure. Thus produced solid was dried under reduced pressure at 40° C., and 835 mg of hydrochloride salt of the title compound [5] was obtained as a pale yellow solid.

The spectral data of the compound [5] are presented below.
$^1$H-NMR (DMSO-d$_6$) δ: 9.99 (d, J=6.8 Hz, 1H×1/2), 9.10 (d, J=6.3 Hz, 1H×1/2), 9.04 (d, J=7.3 Hz, 1H×1/2), 8.99 (d, J=7.8 Hz, 1H×1/2), 8.89 (brs, 1H), 8.76 (s, 1H), 8.71 (s, 1H×1/2), 8.64 (s, 1H×1/2), 8.42-8.40 (m, 1H), 7.46-7.38 (m, 4H), 7.19 (t, J=7.1 Hz, 1H×1/2), 7.07 (t, J=7.1 Hz, 1H×1/2), 6.10 (m, 1H), 5.24 (t, J=7.3 Hz, 1H×1/2), 5.15 (t, J=7.1 Hz, 1H×1/2), 4.87 (m, 1H), 3.07-2.97 (m, 3H), 2.90-2.85 (m, 1H), 1.53 (d, J=7.3 Hz, 3H×1/2), 1.50 (d, J=6.8 Hz, 3H×1/2), 1.33 (t, J=7.6 Hz, 3H×1/2), 1.30 (t, J=7.3 Hz, 3H×1/2), 1.29 (s, 9H×1/2), 1.26 (s, 9H×1/2)

mass: 484 (M+1)$^+$.

Example 6

Synthesis of 2-[((1S)-1-{4-[(1R)-2-(tert-butylamino)-1-hydroxyethyl]phenyl}ethyl)amino]-4-(8-ethylimidazo[1,2-a]pyridin-3-yl)pyrimidine-5-carbonitrile [6] (hereinafter, referred to as the compound [6])

(1) 2.5 g of tert-butyl((1S)-1-{4-[(1R)-2-(tert-butylamino)-1-hydroxyethyl]phenyl}ethyl)carbamate [6-1]

(hereinafter, referred to as the compound [6-1]) was obtained as a white solid from 4.14 g of the compound [5-1] and 24 g of AD-mix-β (available from Aldrich Corporation) according to the methods of Example 5-(2) to (5).

(2) 1.17 g of hydrochloride salt of the compound [6] was obtained as a pale yellow foamy product from 1.5 g of the compound [5-6] and 1.56 g of the compound [6-1] according to the method of Example 5-(7).

The spectral data of the compound [6] are presented below.
$^1$H-NMR (DMSO-$d_6$) δ: 9.98 (d, J=6.8 Hz, 1H×1/2), 9.04 (d, J=8.3 Hz, 1H), 9.01 (d, J=8.3 Hz, 1H×1/2), 8.97-8.92 (m, 1H), 8.76 (s, 1H×1/2), 8.76 (s, 1H×1/2), 8.71 (s, 1H×1/2), 7.49 (d, J=6.3 Hz, 1H×1/2), 7.44-7.37 (m, 5H), 7.21 (t, J=7.3 Hz, 1H×1/2), 7.08 (t, J=7.3 Hz, 1H×1/2), 6.11 (brs, 1H×1/2), 5.27-5.20 (m, 1H×1/2), 5.17-5.10 (m, 1H×1/2), 4.89-4.85 (m, 1H), 3.05-2.95 (m, 3H+1H×1/2), 2.91-2.80 (m, 1H×1/2), 1.53-1.49 (m, 3H), 1.34-1.30 (m, 3H), 1.28 (s, 9H×1/2), 1.25 (s, 9H×1/2).

mass: 484 (M+1)$^+$.

Example 7

Synthesis of 2-{[(1S)-1-(4-{2-[(1,1-dimethylpropyl)amino]-1-hydroxyethyl}phenyl)ethyl]amino}-4-(8-ethylimidazo[1,2-a]pyridin-3-yl)pyrimidine-5-carbonitrile [7] (hereinafter, referred to as the compound [7])

(1) 485 mg of the compound [5-1] was dissolved in a mixed solvent of 18 mL of acetone and 3 mL of water, then 460 mg of 4-methylmorpholine 4-oxide monohydrate and 590 μL of osmium tetroxide (0.1M aqueous solution) were added in that order, and the mixture was stirred overnight at room temperature. 10 mL of 10% aqueous solution of sodium sulfite was added thereto, and after the 30 minutes stirring, the mixture was extracted with ethyl acetate. The obtained organic layer was washed with saturated brine and dried over anhydrous sodium sulfate. The insolubles were filtered, the filtrate was concentrated under reduced pressure, and the resulting residue was purified by silica gel column chromatography (eluent: hexane/ethyl acetate=100/0-0/100), to obtain 351 mg of tert-butyl{(1S)-1-[4-(1,2-dihydroxyethyl) phenyl]ethyl}carbamate [7-1] (hereinafter, referred to as the compound [7-1]) as a colorless oily product.

(2) 255 mg of tert-butyl[(1S)-1-(4-oxiran-2-ylphenyl) ethyl]carbamate [7-2] (hereinafter, referred to as the compound [7-2]) was obtained as a white solid from 351 mg of the compound [7-1] according to the methods of Example 5-(3) and (4).

(3) 30 mg of the compound [7-2] was dissolved in 2 mL of ethanol, then 2 mL of tert-amylamine was added thereto, and the mixture was stirred overnight at 50° C. The reaction solution was concentrated, and then the resulting residue was purified by silica gel column chromatography (eluent: hexane/ethyl acetate=100/0-20/80), to obtain 31 mg of tert-butyl [(1S)-1-(4-{2-[(1,1-dimethylpropyl) amino]-1-hydroxyethyl}phenyl)ethyl]carbamate [7-3] (hereinafter, referred to as the compound [7-3]) as a colorless oily product.

(4) 20 mg of hydrochloride salt of the title compound [7] was obtained as a yellow solid from 31 mg of the compound [7-3] and 31 mg of the compound [5-6] according to the method of Example 5-(7).

The spectral data of the compound [7] are presented below.
$^1$H-NMR (DMSO-$d_6$) δ: 9.99 (d, J=7.3 Hz, 1H×1/2), 9.08-9.02 (m, 1H×1/2), 9.00-8.90 (brs, 1H), 8.79-8.67 (m, 2H), 8.40-8.30 (brs, 1H), 7.54-7.38 (m, 4H), 7.25 (t, J=6.8 Hz, 1H×1/2), 7.11 (dt, J=3.2 Hz, 7.1 Hz, 1H×1/2), 5.24 (t, J=7.3 Hz, 1H×1/2), 5.13 (t, J=6.1 Hz, 1H×1/2), 4.91-4.88 (m, 1H), 3.07-2.97 (m, 3H), 2.91-2.88 (m, 1H), 1.65 (q, J=7.6 Hz, 2H×1/2), 1.62 (q, J=7.6 Hz, 2H×1/2), 1.54 (d, J=6.8 Hz, 3H×1/2), 1.50 (d, J=7.3 Hz, 3H×1/2), 1.33 (t, J=7.6 Hz, 3H×1/2), 1.30 (d, J=6.8 Hz, 3H×1/2), 1.24 (s, 6H×1/2), 1.22 (s, 6H×1/2), 0.85 (q, J=7.6 Hz, 3H)

mass: 498 (M+1)$^+$.

Example 8

Synthesis of 4-(8-ethylimidazo[1,2-a]pyridin-3-yl)-2-[((1S)-1-{4-[1-hydroxy-2-(4-methylpiperazin-1-yl) ethyl]phenyl}ethyl)amino]pyrimidine-5-carbonitrile [8] (hereinafter, referred to as the compound [8])

(1) 35 mg of tert-butyl((1S)-1-{4-[1-hydroxy-2-(4-methylpiperazin-1-yl) ethyl]phenyl}ethyl)carbamate [8-1] (hereinafter, referred to as the compound [8-1]) was obtained as a colorless oily product from 30 mg of the compound [7-2] and 2 mL of N-methylpiperizine according to the method of Example 7-(3).

(2) 19 mg of hydrochloride salt of the title compound [8] was obtained as a yellow solid from 35 mg of the compound [8-1] and 34 mg of the compound [5-6] according to the method of Example 5-(7).

The spectral data of the compound [8] are presented below.
$^1$H-NMR (DMSO-$d_6$) δ: 10.00 (d, J=6.8 Hz, 1H×1/2), 9.02 (t, J=7.3 Hz, 1H), 8.98 (d, J=7.8 Hz, 1H×1/2), 8.76 (s, 1H), 8.71 (s, 1H×1/2), 8.64 (d, J=1.5 Hz, 1H×1/2), 7.48-7.37 (m, 4H), 7.19 (t, J=6.8 Hz, 1H×1/2), 7.04 (m, 1H×1/2), 5.23 (t, J=7.3 Hz, 1H×1/2), 5.13 (t, J=7.1 Hz, 1H×1/2), 5.11-5.00 (m, 1H), 3.46-3.41 (m, 8H), 3.06-2.96 (m, 3H), 2.77 (m, 4H), 1.53 (d, J=7.3 Hz, 3H×1/2), 1.50 (d, J=7.3 Hz, 3H×1/2), 1.33 (t, J=7.3 Hz, 3H×1/2), 1.30 (t, J=7.3 Hz, 3H×1/2)

mass: 548 (M+1)$^+$.

Example 9

Synthesis of 2-[((1S)-1-{4-[(1R)-2-(tert-butylamino)-1-hydroxyethyl]phenyl}ethyl)amino]-4-(8-chloroimidazo[1,2-a]pyridin-3-yl)pyrimidine-5-carbonitrile [9] (hereinafter, referred to as the compound [9])

(1) 6.3 g of 4-(8-chloroimidazo[1,2-a]pyridin-3-yl)-2-(methylthio)pyrimidine-5-carbonitrile [9-1] (hereinafter, referred to as the compound [9-1]) was obtained as a light brown solid from 4 g of 2-amino-3-chloropyridine and 6.9 g of 4-[(Z)-2-ethoxyvinyl]-2-(methylthio)-5-pyrimidinecarbonitrile according to the method of Example 1-(6).

(2) 15 mg of the title compound [9] was obtained as a white foamy product from 20 mg of the compound [9-1] and 22 mg of the compound [6-1] according to the method of Example 1-(7).

The spectral data of the compound [9] are presented below.
$^1$H-NMR (DMSO-$d_6$) δ: 10.06 (d, J=7.3 Hz, 1H×1/2), 9.06 (d, J=7.3 Hz, 1H×1/2), 8.96 (d, J=7.3 Hz, 1H), 8.78 (s, 1H×1/2), 8.75 (s, 1H×1/2), 8.74 (s, 1H×1/2), 8.61 (s, 1H×1/2), 7.79 (d, J=7.3 Hz, 1H×1/2), 7.71 (d, J=7.3 Hz, 1H×1/2), 7.36-7.29 (m, 4H), 7.19 (t, J=7.3 Hz, 1H×1/2), 6.99 (t, J=7.3 Hz, 1H×1/2), 5.28-5.25 (m, 2H), 4.49-4.44 (m, 1H), 2.56-2.51 (m, 2H), 1.53-1.48 (m, 3H), 1.00 (s, 9H×1/2), 0.93 (s, 9H×1/2)

mass: 490 (M+1)$^+$..

Example 10

Synthesis of 2-[((1S)-1-{4-[(1R)-2-(tert-butylamino)-1-hydroxyethyl]phenyl}ethyl)amino]-4-[8-(difluoromethyl)imidazo[1,2-a]pyridin-3-yl]pyrimidine-5-carbonitrile [10] (hereinafter, referred to as the compound [10])

(1) 7.15 g of 4-(8-formylimidazo[1,2-a]pyridin-3-yl)-2-(methylthio)pyrimidine-5-carbonitrile [10-1] (hereinafter, referred to as the compound [10-1]) was obtained as a light brown solid from 5.69 g of 2-amino-3-formylpyridine and 10 g of 4-[(Z)-2-ethoxyvinyl]-2-(methylthio)-5-pyrimidinecarbonitrile according to the method of Example 1-(6).

(2) 5 g of the compound [10-1] was suspended in 200 mL of chloroform, then 7.8 mL of bis(2-methoxyethyl)aminosulfur trifluoride was added thereto under an ice-cold condition, and the mixture was stirred at the same temperature. After about 30 minutes, the reaction mixture which has turned into a clear brown solution was further stirred for 30 minutes, and then 300 mL of a saturated aqueous solution of sodium hydrogen carbonate was added thereto. The organic layer and the aqueous layer were separated, and the aqueous layer was extracted with a mixed solvent of chloroform and methanol (mixing ratio: 9/1). The resultant was combined with the previous organic layer, which was washed with water and dried over anhydrous magnesium sulfate. The insolubles were filtered, the filtrate was concentrated under reduced pressure, and the resulting residue was purified by silica gel column chromatography (eluent: chloroform/ethyl acetate=100/0-30/70). The solvent was distilled off, then dissolved in a small amount of chloroform, and hexane was added thereto be solidified, thereby obtaining 2.03 g of 4-[8-(difluoromethyl)imidazo[1,2-a]pyridin-3-yl]-2-(methylthio)pyrimidine-5-carbonitrile [10-2] (hereinafter, referred to as the compound [10-2]) as a light brown solid.

(3) 12 mg of the title compound [10] was obtained as a white foamy product from 20 mg of the compound [10-2] and 21 mg of the compound [6-1] according to the method of Example 1-(7).

The spectral data of the compound [10] are presented below.

$^1$H-NMR (DMSO-d$_6$) δ: 10.20 (d, J=7.3 Hz, 1H×1/2), 9.09 (d, J=7.3 Hz, 1H×1/2), 9.05 (d, J=7.3 Hz, 1H×1/2), 8.96 (d, J=7.3 Hz, 1H×1/2), 8.78 (s, 1H×1/2), 8.77 (s, 1H×1/2), 8.74 (s, 1H×1/2), 8.63 (s, 1H×1/2), 7.86 (d, J=7.3 Hz, 1H×1/2), 7.78 (d, J=7.3 Hz, 1H×1/2), 7.51 (t, J=54.6 Hz, 1H×1/2), 7.45 (t, J=54.1 Hz, 1H×1/2), 7.37-7.29 (m, 5H+1H×1/2), 7.12 (t, J=7.3 Hz, 1H×1/2), 5.30-5.04 (m, 2H), 4.51-4.45 (m, 1H), 2.60-2.51 (m, 2H), 1.54-1.49 (m, 3H), 1.00 (s, 9H×1/2), 0.94 (s, 9H×1/2).

mass: 506 (M+1)$^+$.

Example 11

Synthesis of (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol [11] (hereinafter, referred to as the compound [11])

(1) A mixture of 3.11 g of 5-bromo-2,4-dichloropyrimidine, 5.18 g of cis-1-ethoxy-2-tri-n-butylstannylethylene (synthesized according to the method disclosed in J. Am. Chem. Soc., 1977, 99, 7365), 0.479 g of dichlorobis(triphenylphosphine)palladium (II), and 60 mL of N, N-dimethylformamide was stirred for 6 hours at 70° C. After standing to cool, 60 mL of water, 60 mL of ethyl acetate, and 20 g of potassium fluoride were added thereto, and the mixture was stirred overnight at room temperature. The insolubles were filtered through celite and the filtrate was extracted with chloroform. The obtained organic layer was washed with water and saturated brine in that order, and dried over anhydrous sodium sulfate. The insolubles were filtered, the filtrate was concentrated under reduced pressure, and the resulting residue was purified by silica gel column chromatography (eluent: 10% chloroform-hexane/ethylacetate=100/0-0/100), to obtain 1.15 g of 5-bromo-2-chloro-4-[(E)-2-ethoxyvinyl]pyrimidine [11-1] (hereinafter, referred to as the compound [11-1]) as a pale yellow solid.

(2) 137 mg of 3-(5-bromo-2-chloropyrimidin-4-yl)-8-ethylimidazo[1,2-a]pyridine [11-2] (hereinafter, referred to as the compound [11-2]) was obtained as a light brown solid from 347 mg of the compound [11-1] and 118 mg of 3-ethylpyridine-2-amine (synthesized according to the method disclosed in International Publication WO2006/025567, page 142) according to the method of Example 1-(6).

(3) 78 mg of the compound [6-1] was dissolved in 2 mL of chloroform, then 2 mL of trifluoroacetic acid was added thereto, and the mixture was stirred for 1 hour at room temperature. The reaction mixture was concentrated under reduced pressure, dissolved in methanol, and passed through a weak ion exchange resin to remove the trifluoroacetic acid. The solvent was distilled off to obtain 55 mg of (1R)-1-{4-[(1S)-1-aminoethyl]phenyl}-2-(tert-butylamino)ethanol [11-3] as a white solid. The compound [11-3] (hereinafter, referred to as the compound [11-3]) was used in the subsequent reaction without further purification.

(4) 55 mg of the compound [11-3], 78 mg of the compound [11-2], and 81 µL of diisopropylethylamine were dissolved in 4 mL of dimethylsulfoxide, and the mixture was stirred for 12 hours at 120° C. After standing to cool, the reaction mixture was purified by preparative reverse-phase liquid chromatography. To the obtained aqueous solution, a saturated aqueous solution of sodium hydrogen carbonate was added to basify the solution, and then the basified solution was extracted with a mixed solvent of chloroform and methanol (mixing ratio: 9/1). The obtained organic layer was washed with saturated brine and dried over anhydrous sodium sulfate. The insolubles were filtered, the filtrate was concentrated under reduced pressure, and the resulting residue was purified by preparative thin-layer chromatography to obtain 78 mg of the title compound [11] as. a gray solid.

The spectral data of the compound [11] are presented below.

$^1$H-NMR (CDCl$_3$) δ: 8.71 (s, 1H), 8.44 (s, 1H), 7.41-7.31 (m, 5H), 7.10 (d, J=7.2 Hz, 1H), 6.65-6.55 (m, 1H), 5.58-5.50 (m, 1H), 5.10-5.02 (m, 1H), 4.59 (dd, J=8.4 Hz, 3.6 Hz, 1H), 3.07 (q, J=7.2 Hz, 2H), 2.91 (dd, J=11.6 Hz, 3.6 Hz, 1H), 2.59 (dd, J=11.6 Hz, 8.4 Hz, 1H), 1.57 (d, J=6.8 Hz, 3H), 1.37 (t, J=7.2 Hz, 3H), 1.09 (s, 9H)

mass: 537, 539 (M+1)$^+$.

Example 12

Synthesis of 2-[((1S)-1-{4-[hydroxy(pyridin-2-yl)methyl]phenyl}ethyl)amino]-4-(8-methylimidazo[1,2-a]pyridin-3-yl)pyrimidine-5-carbonitrile [12] (hereinafter, referred to as the compound [12])

(1) 500 mg of the compound [1-1] was dissolved in 10 mL of tetrahydrofuran and cooled to −78° C. Thereafter, 2.33 mL of n-butyllithium (1.57M hexane solution) was added thereto.

After the 1 hour stirring at the same temperature, 193 μL of picolinaldehyde was added to the resulting white suspension, and the suspension was stirred overnight while heating back to room temperature. 50 mL of water was added to the reaction mixture, and the mixture was extracted with 200 mL of ethyl acetate. The obtained organic layer was washed with saturated brine and dried over anhydrous magnesium sulfate. Then, the insolubles were filtered and the filtrate was concentrated under reduced pressure. The resulting residue was purified by silica gel column chromatography (eluent: hexane/ethyl acetate=100/0-30/70) to obtain 212 mg of tert-butyl ((1S)-1-{4-[hydroxy (pyridin-2-yl)methyl]phenyl}ethyl) carbamate [12-1] (hereinafter, referred to as the compound [12-1]) as a light brown oily product.

(2) 24 mg of the title compound [12] was obtained as a gray solid from 58 mg of the compound [12-1] and 41 mg of the compound [1-6] according to the method of Example 1-(7).

The spectral data of the compound [12] are presented below.

$^1$H-NMR (DMSO-d$_6$) δ: 9.95 (d, J=6.8 Hz, 1H×1/2), 8.94 (d, J=7.1 Hz, 1H×1/2), 8.88 (d, J=7.8 Hz, 1H×1/2), 8.75-8.70 (m, 1H+1H×1/2), 8.67 (s, 1H×1/2), 8.56-8.55 (m, 1H×1/2), 8.42-8.35 (m, 1H), 7.77-7.67 (m, 1H), 7.56-7.51 (m, 1H), 7.42-7.25 (m, 5H), 7.21-7.15 (m, 1H), 7.11 (t, J=6.8 Hz, 1H×1/2), 6.68-6.61 (m, 1H×1/2), 6.03-6.00 (m, 1H), 5.66-5.65 (m, 1H), 5.19 (quint, J=7.1 Hz, 1H×1/2), 5.02 (quint, J=6.8 Hz, 1H×1/2), 2.58 (s, 3H×1/2), 2.52 (s, 3H×1/2), 1.49 (d, J=7.1 Hz, 3H×1/2), 1.45 (d, J=6.8 Hz, 3H×1/2)

mass: 462 (M+1)$^+$.

Example 13

Synthesis of 2-[((1S)-1-{4-[hydroxy(phenyl)methyl]phenyl}ethyl)amino]-4-(8-methylimidazo[1,2-a]pyridin-3-yl)pyrimidine-5-carbonitrile [13] (hereinafter, referred to as the compound [13])

11 mg of the title compound [13] was obtained as a white solid from 100 mg of the compound [1-1], 51 μL of benzaldehyde, and 38 mg of the compound [1-6], according to the method of Example 12.

The spectral data of the compound [13] are presented below.

$^1$H-NMR (DMSO-d$_6$) δ: 9.98-9.94 (m, 1H×1/2), 8.96-8.94 (m, 1H×1/2), 8.89-8.87 (m, 1H×1/2), 8.80-8.78 (m, 1H×1/2), 8.73-8.71 (m, 1H), 8.68-8.67 (m, 1H×1/2), 8.58-8.56 (m, 1H×1/2), 7.42-7.09 (m, 10H+1H×1/2), 6.69-6.63 (m, 1H×1/2), 5.82 (brs, 1H), 5.65 (brs, 1H), 5.23-5.13 (m, 1H×1/2), 5.06-4.99 (m, 1H×1/2), 2.57 (s, 3H×1/2), 2.52 (s, 3H×1/2), 1.49 (d, J=6.8 Hz, 3H×1/2), 1.46 (d, J=6.8 Hz, 3H×1/2)

mass: 461 (M+1)$^+$.

Example 14

Synthesis of 2-[((1S)-1-{4-[hydroxy(1-methyl-1H-imidazol-2-yl) methyl]phenyl}ethyl)amino]-4-(8-methylimidazo[1,2-a]pyridin-3-yl)pyrimidine-5-carbonitrile [14] (hereinafter, referred to as the compound [14])

23 mg of the title compound [14] was obtained as a white solid from 100 mg of the compound [1-1], 75 mg of 1-methyl-2-imidazolecarboxyaldehyde, and 74 mg of the compound [1-6] according to the method of Example 12.

The spectral data of the compound [14] are presented below.

$^1$H-NMR (DMSO-d$_6$) δ: 9.97 (d, J=7.1 Hz, 1H×1/2), 8.97 (d, J=7.1 Hz, 1H×1/2), 8.92-8.87 (m, 1H×1/2), 8.78-8.69 (m, 1H+1H×1/2), 8.59 (s, 1H×1/4), 8.57 (s, 1H+1H×1/4), 7.43-7.24 (m, 5H+1H×1/2), 712 (t, J=7.2 Hz, 1H×1/2), 7.01-6.96 (m, 1H), 6.87 (t, J=7.0 Hz, 1H×1/4), 6.74-6.72 (m, 1H), 6.63 (t, J=7.0 Hz, 1H×1/4), 6.11-6.08 (m, 1H), 5.83-5.81 (m, 1H), 5.25-5.21 (m, 1H×1/2), 5.09-5.03 (m, 1H×1/2), 3.50 (s, 3H×1/2), 3.37 (s, 3H×1/2), 2.58 (s, 3H×1/2), 2.53 (s, 3H×1/2), 1.52 (d, J=6.8 Hz, 3H×1/2), 1.49 (d, J=7.1 Hz, 3H×1/2), mass: 465 (M+1)$^+$.

Example 15

Synthesis of 2[((1S)-1-{4-[hydroxy(pyridin-4-yl) methyl]phenyl}ethyl)amino]-4-(8-methylimidazo[1,2-a]pyridin-3-yl)pyrimidine-5-carbonitrile [15] (hereinafter, referred to as the compound [15])

(1) 5 g of the compound [1-1] was dissolved in 100 mL of tetrahydrofuran and cooled to −78° C. Thereafter, 31.2 mL of n-butyllithium (1.6 M hexane solution) was added thereto, and the mixture was stirred for 1 hour at the same temperature. 774 μL of N,N-dimethylformamide was added to the produced white suspension, which was stirred for 5 hours while gradually heating back to room temperature. To the reaction mixture was added a saturated aqueous solution of ammonium chloride, and the mixture was extracted with ethyl acetate. The obtained organic layer was washed with saturated brine and dried over anhydrous magnesium sulfate. The insolubles were filtered, the filtrate was concentrated under reduced pressure, and the resulting residue was purified by silica gel column chromatography (eluent: hexane/ethyl acetate=100/0-50/50), to obtain 514 mg of tert-butyl[(1S)-1-(4-formylphenyl) ethyl]carbamate [15-1] (hereinafter, referred to as the compound [15-1]) as a pale yellow amorphous.

(2) To the solution prepared by dissolving 163 mg of 4-bromopyridine in 3 mL of tetrahydrofuran, 514 μL of isopropylmagnesium chloride (2.0M tetrahydrofuran solution) was added, and the mixture was stirred for 1.5 hours at room temperature. Thereafter, 171 mg of the compound [15-1] was added thereto, and the mixture was stirred overnight at room temperature. 100 mL of water was added to the reaction solution, which was extracted with chloroform. The obtained organic layer was dried over anhydrous magnesium sulfate, the insolubles were filtered, and the filtrate was concentrated under reduced pressure. The resulting residue was purified by preparative thin-layer chromatography, and 41 mg of tert-butyl((1S)-1-{4-[(R)-hydroxy(pyridin-4-yl)methyl]phenyl}ethyl)carbamate [15-2] (hereinafter, referred to as the compound [15-2]) was obtained as a pale yellow amorphous.

(3) 8 mg of the title compound [15] was obtained as a gray solid from 41 mg of the compound [15-2] and 32 mg of the compound [1-6] according to the method of Example 1-(7).

The spectral data of the compound [15] are presented below.

$^1$H-NMR (DMSO-d$_6$) δ: 9.95 (d, J=7.1 Hz, 1H×1/2), 8.95 (d, J=7.1 Hz, 1H×1/2), 8.89 (d, J=8.0 Hz, 1H×1/2), 8.80 (d, J=7.1 Hz, 1H×1/4), 8.77 (d, J=7.1 Hz, 1H×1/4), 8.73 (s, 1H×1/2), 8.72 (s, 1H×1/2), 8.68 (s, 1H×1/2), 8.57 (s, 1H×1/2), 8.46-8.44 (m, 1H), 8.41-8.39 (m, 1H), 8.42-8.24 (m, 7H), 7.11 (t, J=7.1 Hz, 1H×2/4), 6.71 (t, J=7.1 Hz, 1H×1/4), 6.60 (t, J=7.1 Hz, 1H×1/4), 6.08-6.05 (m, 1H), 5.67 (brs, 1H), 5.20 (quint, J=7.6 Hz, 1H×1/2), 5.08-5.00 (m, 1H×1/2), 2.58 (s, 3H×1/2), 2.53 (s, 3H×1/2), 1.49 (d, J=7.1 Hz, 3H×1/2), 1.46 (d, J=7.1 Hz, 3H×1/2)

mass: 462 (M+1)$^+$.

Example 16

Synthesis of 2-({(1S)-1-[4-(1-hydroxy-2-phenylethyl)phenyl]ethyl}amino)-4-(8-methylimidazo[1,2-a]pyridin-3-yl)pyrimidine-5-carbonitrile [16] (hereinafter, referred to as the compound [16])

(1) 70 mg of the compound [15-1] was dissolved in 5 mL of tetrahydrofuran and cooled to 0° C. Thereafter, 300 µL of benzylmagnesium chloride (2.0M tetrahydrofuran solution) was added thereto, and the mixture was stirred overnight while gradually heating back to room temperature. To the reaction solution was added a saturated aqueous solution of ammonium chloride, and the solution was extracted with ethyl acetate. The obtained organic layer was washed with water and saturated brine in that order, and dried over anhydrous sodium sulfate. The insolubles were filtered, the filtrate was concentrated under reduced pressure, and then the resulting residue was purified by preparative thin-layer chromatography, to obtain 11 mg of the tert-butyl {(1S)-1-[4-(1-hydroxy-2-phenylethyl) phenyl]ethyl}carbamate [16-1] (hereinafter, referred to as the compound [16-1]) as a colorless oily product.

(2) 4 mg of the title compound [16] was obtained as a gray solid from 11 mg of the compound [16-1] and 10 mg of the compound [1-6] according to the method of Example 1-(7).

The spectral data of the compound [16] are presented below.

$^1$H-NMR (CDCl$_3$) δ: 9.80 (d, J=7.2 Hz, 1H×1/5), 9.12-8.75 (m, 1H+1H×4/5), 8.55 (s, 1H×1/5), 8.50 (s, 1H×4/5), 8.10-7.00 (m, 11H), 6.68-6.60 (m, 1H), 5.80 (brs, 1H), 5.15-5.10 (m, 1H×1/5), 4.94-4.89 (m, 1H×4/5), 2.64 (s, 3H), 1.64 (d, J=6.8 Hz, 3H)

mass: 475 (M+1)$^+$.

Example 17

Synthesis of 2-[((1S)-1-{4-[1-hydroxy-2-(1-methylpiperidin-4-yl) ethyl]phenyl}ethyl)amino]-4-(8-methylimidazo[1,2-a]pyridin-3-yl)pyrimidine-5-carbonitrile [17] (hereinafter, referred to as the compound [17])

(1) 43 mg of benzyl-4-{2-[4-((1S)-1-{[5-cyano-4-(8-methylimidazo[1,2-a]pyridin-3-yl)pyrimidin-2-yl]amino}ethyl)phenyl]-2-hydroxyethyl}piperidine-1-carboxylate [17-1] (hereinafter, referred to as the compound [17-1]) was obtained as a pale yellow solid from 300 mg of the compound [1-1], 516 mg of 1-benzyloxycarbonyl-4-(formylmethyl)piperidine (synthesized according to the method disclosed in specification of European Patent Publication No. 0367110, pages 108 to 109), and 41 mg of the compound [1-6] according to the method of Example 12.

(2) 21 mg of the compound [17-1] was dissolved in a mixed solvent of 3 mL of tetrahydrofuran and 3 mL of methanol, then 20 mg of a carbon catalyst of 20% palladium hydroxide was added thereto, and the mixture was stirred for 2 hours at room temperature under hydrogen atmosphere. The catalyst was filtered through celite, and the filtrate was concentrated under reduced pressure. Diethylether was added to the resulting residue, and thus produced solid was taken by filtration to obtain 6 mg of 2-({(1S)-1-[4-(1-hydroxy-2-piperidin-4-yl-ethyl)phenyl]ethyl}amino)-4-(8-methylimidazo[1,2-a]pyridin-3-yl)pyrimidine-5-carbonitrile [17-2] (hereinafter, referred to as the compound [17-2]).

(3) To a mixture of 2 mg of the compound [17-2] and 100 µL of a 37% formaldehyde solution, 200 µL of methanol solution containing 4 mg of zinc chloride and 4 mg of sodium cyanotrihydroborate was added, and the mixture was stirred overnight at room temperature. To the reaction mixture was added water and chloroform, and the organic layer was separated from the aqueous layer. The obtained organic layer was washed with a saturated aqueous solution of sodium hydrogen carbonate and saturated brine in that order, and dried over anhydrous sodium sulfate. The insolubles were filtered, and the filtrate was concentrated under reduced pressure. Diethylether was added to the resulting residue, and the resulting solid was taken by filtration, to obtain 2.2 mg of the title compound [17] as a gray solid.

The spectral data of the compound [17] are presented below.

$^1$H-NMR (CDCl$_3$) δ: 9.62 (d, J=7.2 Hz, 1H×1/5), 8.92-8.64 (m, 1H+1H×4/5), 8.55 (s, 1H×1/5), 8.41 (s, 1H×4/5), 7.45-6.55 (m, 6H), 6.23-6.20 (m, 1H×4/5), 5.95-5.90 (m, 1H×1/5), 5.40-4.70 (m, 2H), 3.00-2.70 (m, 4H), 2.58 (s, 3H), 2.30 (s, 3H), 2.10-1.40 (m, 7H), 1.62 (d, J=6.8 Hz, 3H)

mass: 496 (M+1)$^+$.

Example 18

Synthesis of 2-({(1S)-1-[4-(4-hydroxypiperidin-4-yl) phenyl]ethyl}amino)-4-(8-methylimidazo[1,2-a]pyridin-3-yl)pyrimidine-5-carbonitrile [18] (hereinafter, referred to as the compound [18])

(1) 171 mg of benzyl-4-(4-{(1S)-1-[(tert-butoxycarbonyl)amino]ethyl}phenyl)-4-hydroxypiperidine-1-carboxylate [18-1] (hereinafter, referred to as the compound [18-1]) was obtained from 200 mg of the compound [1-1] and 186 mg of N-benzyloxycarbonyl-4-piperidone according to the method of Example 12-(1).

(2) 18 mg of benzyl-4-[4-((1S)-1-{[5-cyano-4-(8-methylimidazo[1,2-a]pyridin-3-yl) pyrimidin-2-yl]amino}ethyl)phenyl]-4-hydroxypiperidine-1-carboxylate [18-2] (hereinafter, referred to as the compound [18-2]) from 82 mg of the compound [18-1] and 50 mg of the compound [1-6] according to the method of Example 1-(7).

(3) To a solution prepared by dissolving 14 mg of the compound [18-2] in a mixed solvent of 2 µL of tetrahydrofuran and 0.2 ml of methanol, 15 mg of 10% palladium carbon catalyst was added, and the mixture was stirred overnight at room temperature under hydrogen atmosphere. The catalyst was filtered through celite, the filtrate was concentrated under reduced pressure, and the resulting residue was purified by preparative thin-layer chromatography, to obtain 2 mg of the title compound [18] as a pale yellow amorphous.

The spectral data of the compound [18] are presented below.

$^1$H-NMR (CDCl$_3$) δ: 9.65-9.62 (m, 1H×1/5), 8.95 (s, 1H×1/5), 8.89 (s, 1H×4/5), 8.79 (d, J=7.3 Hz, 1H×4/5), 8.56-8.56 (m, 1H×1/5), 8.52 (s, 1H×4/5), 7.57-7.52 (m, 2H), 7.40-7.38 (m, 2H), 7.27-7.25 (m, 1H×1/5), 7.15 (d, J=6.8 Hz, 1H×4/5), 6.96-6.92 (m, 1H×1/5), 6.59 (t, J=6.8 Hz, 1H×4/5), 6.05-6.03 (m, 1H×4/5), 5.84-5.82 (m, 1H×1/5), 6.36-6.32 (m, 1H×1/5), 5.17-5.10 (m, 1H×4/5), 4.43-4.42 (m, 1H×1/5), 4.29-4.27 (m, 1H×4/5), 3.14-3.08 (m, 2H), 2.98-2.95 (m, 2H), 2.83 (s, 3H×1/5), 2.63 (s, 3H×4/5), 2.06-1.99 (m, 2H), 1.73-1.68 (m, 2H), 1.28-1.25 (m, 3H)

mass: 454 (M+1)$^+$.

Example 19

Synthesis of 2-({(1S)-1-[4-(3-hydroxy-1-methylpyrrolidin-3-yl)phenyl]ethyl}amino)-4-(8-methylimidazo[1,2-a]pyridin-3-yl)pyrimidine-5-carbonitrile [19] (hereinafter, referred to as the compound [19])

(1) 23 mg of benzyl3-[4-((1S)-1-{[5-cyano-4-(8-methylimidazo[1,2-a]pyridin-3-yl)pyrimidin-2-yl]amino}ethyl)phenyl]-3-hydroxypyrrolidine-1-carboxylate [19-1] (hereinafter, referred to as the compound [19-1]) was obtained as a yellow oily product from 164 mg of 1-N-benyzyloxycarbonyl-3-pyrrolidinone, 150 mg of the compound [1-1], and 33 mg of the compound [1-6] according to the method of Example 12.

(2) 6 mg of the title compound [19] was obtained as a white solid from 15 mg of the compound [19-1] according to the methods of Example 1 7-(2) and (3).

The spectral data of the compound [19] are presented below.

$^1$H-NMR (CDCl$_3$) δ: 9.64 (d, J=6.8 Hz, 1H×1/5), 8.94 (s, 1H×1/5), 8.87 (s, 1H×4/5), 8.78 (d, J=6.8 Hz, 1H×4/5), 8.56 (s, 1H×1/5), 8.49 (s, 1H×4/5), 7.56-6.93 (m, 5H), 6.64-6.60 (m, 1H), 6.22-6.12 (m, 1H×4/5), 5.92-5.85 (m, 1H×1/5), 5.38-5.28 (m, 1H×1/5), 5.15-5.11 (m, 1H×4/5), 3.20-3.14 (m, 1H), 2.98-2.93 (m, 1H), 2.68-2.61 (m, 1H), 2.65 (s, 1H×3/5), 2.63 (s, 2H+1H×2/5), 2.54-2.17 (m, 3H), 2.45 (s, 2H+1H×2/5), 2.44 (s, 1H×3/5), 2.10 (brs, 1H), 1.63 (d, J=6.8 Hz, 3H)

mass: 454 (M+1)$^+$.

Example 20

Synthesis of 4-(8-ethylimidazo[1,2-a]pyridin-3-yl)-2-({(1S)-1-[4-(4-hydroxy-1-methylpiperidin-4-yl)phenyl]ethyl}amino)pyrimidine-5-carbonitrile [20] (hereinafter, referred to as the compound [20])

(1) 102 mg of benzyl 4-[4-((1S)-1-{[5-cyano-4-(8-ethylimidazo[1,2-a]pyridin-3-yl) pyrimidin-2-yl]amino}ethyl)phenyl]-4-hydroxypiperidine-1-carboxylate [20-1] (hereinafter, referred to as the compound [20-1]) was obtained from 119 mg of the compound [18-1] and 115 mg of the compound [5-6] according to the method of Example 1-(7).

(2) 8 mg of the title compound was obtained as a white solid from 102 mg of the compound [20-1] according to the methods of Example 1 7-(2) and (3).

The spectral data of the compound [20] are presented below.

$^1$H-NMR (CDCl$_3$) δ: 9.61 (d, J=7.2 Hz, 1H×1/4), 8.92 (s, 1H×1/4), 8.85 (s, 1H×3/4), 8.76 (d, J=7.2 Hz, 1H×3/4), 8.55 (s, 1H×1/4), 8.43 (s, 1H×3/4), 7.60-6.90 (m, 5H+1H×1/4), 6.61 (t, J=6.4 Hz, 1H×3/4), 6.29-6.28 (m, 1H×3/4), 5.96-5.92 (m, 1H×1/4), 5.40-5.30 (m, 1H×1/4), 5.18-5.08 (m, 1H×3/4), 3.48 (s, 3H) 3.10-3.00 (m, 2H), 2.80-2.70 (m, 2H), 2.50-2.40 (m, 2H), 2.20-2.10 (m, 2H), 1.85-1.70 (m, 2H), 1.62 (d, J=7.2 Hz, 3H), 1.56-1.51 (m, 3H), 1.43-1.33 (m, 3H)

mass: 482 (M+1)$^+$.

Example 21

Synthesis of 4-(8-ethylimidazo[1,2-a]pyridin-3-yl)-2-({(1S)-1-[4-(3-hydroxy-1-methylazetidin-3-yl)phenyl]ethyl}amino)pyrimidine-5-carbonitrile [21] (hereinafter, referred to as the compound [21])

(1) 127 mg of tert-butyl((1S)-1-{4-[1-(diphenylmethyl)-3-hydroxyazetidin-3-yl]phenyl}ethyl)carbamate [21-1] (hereinafter, referred to as the compound [21-1]) was obtained as a pale yellow solid from 137 mg of 1-benzhydrylazetidin-3-one and 300 mg of the compound [1-1] according to the method of Example 1 2-(1).

(2) 64 mg of 2-[((1S)-1-{4-[1-(diphenylmethyl)-3-hydroxyazetidin-3-yl]phenyl}ethyl)amino]-4-(8-ethylimidazo[1,2-a]pyridin-3-yl)pyrimidine-5-carbonitrile [21-2] (hereinafter, referred to as the compound [21-2]) was obtained as a pale yellow solid from 96 mg of the compound [21-1] and 62 mg of the compound [5-6] according to the method of Example 1-(7).

(3) 6 mg of the title compound [21] was obtained as a gray solid from 64 mg of the compound [21-2] according to the methods of Example 1 7-(2) and (3).

The spectral data of the compound [21] are presented below.

$^1$H-NMR (CDCl$_3$) δ: 9.63 (d, J=7.2 Hz, 1H×1/5), 9.00-8.70 (m, 1H+1H×4/5), 8.56 (s, 1H×1/5), 8.52 (s, 1H×4/5), 7.68-6.60 (m, 6H), 6.18-6.10 (m, 1H), 5.20-5.15 (m, 1H), 3.70-3.65 (m, 2H), 3.44-3.40 (m, 2H), 3.10-3.00 (m, 2H), 2.44 (s, 3H), 1.62 (d, J=7.0 Hz, 3H), 1.50-1.30 (m, 3H)

mass: 454 (M+1)$^+$.

Example 22

Synthesis of 4-(8-ethylimidazo[1,2-a]pyridin-3-yl)-2-({(1S)-1-[4-(1-hydroxy-1-piperidin-4-yl)ethyl)phenyl]ethyl}amino)pyrimidine-5-carbonitrile [22] (hereinafter, referred to as the compound [22])

(1) 1.26 g of benzyl-4-(4-{(1S)-1-[(tert-butoxycarbonyl)amino]ethyl}benzoyl)piperidine-1-carboxylate [22-1] (hereinafter, referred to as the compound [22-1]) was obtained from 2.39 g of benzyl-4-(N-methoxy-N-methylcarbamoyl)piperidine-1-carboxylate and 2.13 g of the compound [1-1] according to the method of Example 1 2-(1).

(2) 112 mg of the compound [22-1] was dissolved in 5 mL of tetrahydrofuran, and cooled to 0° C. Thereafter, 320 μL of methylmagnesium chloride (3.0M tetrahydrofuran solution) was added thereto, and the mixture was stirred for 1.5 hours while heating back to room temperature. To the reaction solution was added a saturated aqueous solution of ammonium chloride, and the solution was extracted with ethyl acetate. The obtained organic layer was washed with saturated brine and dried over anhydrous magnesium sulfate. The insolubles were filtered, the filtrate was concentrated under reduced pressure, and the resulting residue was purified by silica gel column chromatography (eluent: hexane/ethyl acetate=100/0-30/70), to obtain 53 mg of benzyl-4-[1-(4-{(1S)-1-[(tert-butoxycarbonyl)amino]ethyl}phenyl)-1-hydroxyethyl]piperidine-1-carboxylate [22-2] (hereinafter, referred to as the compound [22-2]).

(3) 17 mg of benzyl-4-{1-[4-((1S)-1-{[5-cyano-4-(8-ethylimidazo[1,2-a]pyridin-3-yl) pyrimidin-2-yl]amino}ethyl)phenyl]-1-hydroxyethyl}piperidine-1-carboxylate [22-3] (hereinafter, referred to as the compound [22-3]) was obtained from 53 mg of the compound [22-2] and 30 mg of the compound [5-6] according to the method of Example 1-(7).

(4) 5 mg of the title compound [22] was obtained as a gray solid from 17 mg of the compound [22-3] according to the method of Example 1 7-(2).

The spectral data of the compound [22] are presented below.

$^1$H-NMR (DMSO-d$_6$) δ: 9.98 (d, J=7.1 Hz, 1H×1/2), 8.96 (d, J=6.8 Hz, 1H×1/2), 8.88 (d, J=8.3 Hz, 1H×1/2), 8.85 (d, J=7.1 Hz, 1H×1/2), 8.74-8.71 (m, 1H+1H×1/2), 8.60 (s,

1H×1/2), 8.59 (s, 1H×1/2), 7.51-7.31 (m, 5H), 7.14 (t, J=7.1 Hz, 1H×1/2), 6.91-6.86 (m, 1H×1/2), 3.46-3.40 (m, 1H), 3.01 (q, J=7.6 Hz, 1H×1/2), 2.96 (q, J=7.6 Hz, 1H×1/2), 2.93-2.17 (m, 2H), 1.53-1.49 (m, 4H), 1.36-1.22 (m, 7H), 1.13-0.96 (m, 4H)

mass: 496 (M+1)$^+$.

Examples 23 and 24

Synthesis of 4-(8-ethylimidazo[1,2-a]pyridin-3-yl)-2-[((1S)-1-{4-[hydroxy(1-methylpiperidin-4-yl)methyl]phenyl}ethyl)amino]pyrimidine-5-carbonitriles [23] (hereinafter, referred to as the compound [23]) and [24] (hereinafter, referred to as the compound [24]), (here, the compound [23] and the compound [24] are diastereomers. Please see Table 6)

(1) To a mixture of 975 mg of magnesium, 100 μL of bromoethane, and 20 μL of tetrahydrofuran, a catalyst amount of iodine was added, and the mixture was stirred for about 10 minutes until the brown color from iodine disappears. Thereto, 20 mL of a tetrahydrofuran solution containing 5.9 g of 4-chloro-1-methylpiperidine was added, and heated for 2.5 hours under reflux. Thus produced white suspension was cooled to 0° C., and 10 mL of a tetrahydrofuran solution containing 2 g of the compound [15-1] was added thereto. After the overnight stirring under gradually heating back to room temperature, a saturated aqueous solution of ammonium chloride was added thereto, and extracted with ethyl acetate. The obtained organic layer was washed with water and saturated brine in that order, and dried over anhydrous magnesium sulfate. The insolubles were filtered, the filtrate was concentrated under reduced pressure, and the resulting residue was purified by silica gel column chromatography (eluent: chloroform/methanol=100/0-90/10), to obtain 2.27 g of tert-butyl((1S)-1-{4-[hydroxy(1-methylpiperidin-4-yl)methyl]phenyl}ethyl)carbamate [23-1] (hereinafter, referred to as the compound [23-1]).

(2) 1.2 g of a mixture of the title compounds [23] and [24] was obtained from 1.42 g of the compound [23-1] and 1 g of the compound [5-6] according to the method of Example 1-(7).

(3) 700 mg of the mixture of the compounds [23] and [24] was resolved using Chiralcel OD-H.

The optical resolution conditions are as follows.

column: Chiralcel OD-H (Daicel Chemical Industries Ltd.), diameter of 20 mm, length of 250 mm;
eluent: hexane/ethanol/diethylamine=85/15/0.1;
flow rate: 15 mL/min.

The obtained solution was concentrated under reduced pressure, and the residue was dissolved in a small amount of chloroform to be solidified with diethylether, thereby obtaining 217 mg of the title compound [23] (RT=18.3 minutes) as a white solid and 230 mg of the title compound [24] (RT=24.3 minutes) as a pale yellow solid.

The spectral data of the compound [23] and the compound [24] are presented below.
Compound [23]
$^1$H-NMR (DMSO-d$_6$) δ: 9.98 (d, J=6.3 Hz, 1H×2/5), 8.97 (d, J=7.1 Hz, 1H×3/5), 8.90 (d, J=7.3 Hz, 1H), 8.73 (s, 1H), 8.70 (s, 1H×2/5), 8.60 (s, 1H×3/5), 7.42 (d, J=6.1 Hz, 1H×2/5), 7.35-7.33 (m, 2H+1H×3/5), 7.26-7.21 (m, 2H), 7.15 (t, J=7.1 Hz, 1H×2/5), 6.89 (t, J=7.1 Hz, 1H×3/5), 5.24 (quint, J=7.1 Hz, 1H×2/5), 5.17-5.05 (m, 1H+1H×3/5), 4.20-4.13 (m, 1H), 3.02 (q, J=7.6 Hz, 2H×2/5), 2.96 (q, J=7.6 Hz, 2H×3/5), 2.74-2.63 (m, 1H+1H×3/5), 2.50-2.48 (m, 1H×3/5), 2.06 (s, 3H×2/5), 2.02 (s, 3H×3/5), 1.73-1.62 (m, 2H+1H×2/ 5), 1.52 (d, J=7.1 Hz, 3H×2/5), 1.49 (d, J=7.1 Hz, 3H×3/5), 1.32 (t, J=7.6 Hz, 3H×2/5), 1.28 (t, J=7.6 Hz, 3H×3/5), 1.22-1.04 (m, 4H), 0.97-0.94 (m, 1H×3/5)

mass: 496 (M+1)$^+$.

Compound [24]
$^1$H-NMR (DMSO-d$_6$) δ: 9.98 (d, J=6.1 Hz, 1H×1/2), 8.97 (d, J=7.1 Hz, 1H×1/2), 8.90-8.89 (m, 1H), 8.73 (s, 1H×1/2), 8.73 (s, 1H×1/2), 8.70 (s, 1H×1/2), 8.60 (s, 1H×1/2), 7.43 (d, J=6.1 Hz, 1H×1/2), 7.35-7.33 (m, 2H+1H×1/2), 7.25 (d, J=8.3 Hz, 1H×1/2), 7.22 (d, J=8.0 Hz, 1H×1/2), 7.15 (t, J=7.1 Hz, 1H×1/2), 6.92 (t, J=7.1 Hz, 1H×1/2), 5.24 (quint, J=7.1 Hz, 1H×1/2), 5.08-5.05 (m, 1H+1H×1/2), 4.20-4.16 (m, 1H), 3.01 (q, J=7.6 Hz, 2H×1/2), 2.96 (q, J=7.6 Hz, 2H×1/2), 2.74-2.64 (m, 1H+1H×1/2), 2.55-2.51 (m, 1H×1/2), 2.06 (s, 3H×1/2), 2.02 (s, 3H×1/2), 1.72-1.55 (m, 2H+1H×1/2), 1.52 (d, J=7.1 Hz, 3H×1/2), 1.49 (d, J=7.1 Hz, 3H×1/2), 1.32 (t, J=7.6 Hz, 3H×1/2), 1.28 (t, J=7.6 Hz, 3H×1/2), 1.22-1.11 (m, 4H), 1.03-1.00 (m, 1H×1/2)

mass: 496 (M+1)$^+$.

Example 25

Synthesis of 4-(8-ethylimidazo[1,2-a]pyridin-3-yl)-2-{[(1S)-1-(4-{hydroxy[1-(2-methoxyethyl) piperidin-4-yl]methyl}phenyl)ethyl]amino}pyrimidine-5-carbonitrile [25] (hereinafter, referred to as the compound [25])

(1) 267 mg of the compound [22-1] was dissolved in a mixed solvent of 10 mL of tetrahydrofuran and 1 mL of methanol, then 22 mg of sodium boronhydride was added thereto, and the mixture was stirred overnight at room temperature. Water was added to the reaction solution, which was extracted with ethyl acetate. The obtained organic layer was washed with water and saturated brine in that order, and dried over anhydrous magnesium sulfate. The insolubles were filtered, the filtrate was concentrated under reduced pressure, and the resulting residue was purified by silica gel column chromatography (eluent: hexane/ethyl acetate=100/0-30/70), to obtain 256 mg of benzyl-4-[(4-{(1S)-1-[(tert-butoxycarbonyl)amino]ethyl}phenyl)(hydroxy)methyl]piperidine-1-carboxylate [25-1] (hereinafter, referred to as the compound [25-1]).

(2) 118 mg of benzyl-4-[[4-((1S)-1-{[5-cyano-4-(8-ethylimidazo[1,2-a]pyridin-3-yl)pyrimidin-2-yl]amino}ethyl)phenyl](hydroxy)methyl]piperidine-1-carboxylate [25-2] (hereinafter, referred to as the compound [25-2]) was obtained from 256 mg of the compound [25-1] and 146 mg of the compound [5-6] according to the method of Example 1-(7).

(3) 118 mg of the compound [25-2] was dissolved in 4 mL of ethanol, then 50 mg of a carbon catalyst of 20% palladium hydroxide was added thereto, and the mixture was stirred overnight at room temperature under hydrogen atmosphere. The catalyst was filtered through celite, the filtrate was concentrated under reduced pressure, and then the resulting residue was purified by preparative thin-layer chromatography, to obtain 66 mg of 4-(8-ethylimidazo[1,2-a]pyridin-3-yl)-2-[((1S)-1-{4-[hydroxy(piperidin-4-yl)methyl]phenyl}ethyl) amino]pyrimidine-5-carbonitrile [25-3] (hereinafter, referred to as the compound [25-3]).

(4) 33 mg of the compound [25-3] was dissolved in 1 mL of N,N-dimethylformamide, then 29 mg of potassium carbonate and 10 μL of 2-bromoethylmethylether were added, and the mixture was stirred for 2.5 hours at 50° C. After standing to cool, the reaction solution was diluted with chloroform, and washed with water. The organic layer was dried over anhydrous magnesium sulfate, and then the insolubles were filtered and the filtrate was concentrated under reduced pressure. The resulting residue was purified by preparative thin-layer chromatography, and the obtained crude and purified product was dissolved in a small amount of chloroform to be solidified with hexane, thereby obtaining 21 mg of the title compound [25] as a white solid.

The spectral data of the compound [25] are presented below.

$^1$H-NMR (CDCl$_3$) δ: 9.65-9.63 (m, 1H×1/5), 8.94 (s, 1H×1/5), 8.89 (s, 1H×4/5), 8.83 (d, J=6.8 Hz, 1H×4/5), 8.57 (s, 1H×1/5), 8.51 (s, 1H×4/5), 7.38-7.30 (m, 4H), 7.16 (d, J=6.8 Hz, 1H), 7.00-6.96 (m, 1H×1/5), 6.68-6.62 (m, 1H×4/5), 6.03 (d, J=5.8 Hz, 1H×4/5), 5.83-5.81 (m, 1H×1/5), 5.34 (brs, 1H×1/5), 5.17-5.09 (m, 1H×4/5), 4.39 (d, J=6.3 Hz, 1H), 3.48-3.44 (m, 2H), 3.32 (s, 3H×4/5), 3.31 (s, 3H×1/5), 3.12-2.79 (m, 4H), 2.52-2.48 (m, 2H), 1.93-1.88 (m, 2H), 1.63 (d, J=7.1 Hz, 3H), 1.46-1.17 (m, 7H)

mass: 540 (M+1)$^+$.

Examples 26 and 27

Synthesis of 4-(8-ethylimidazo[1,2-a]pyridin-3-yl)-2-[((1S)-1-{4-[hydroxy(1-isopropylpiperidin-4-yl)methyl]phenyl}ethyl)amino]pyrimidine-5-carbonitriles [26] (hereinafter, referred to as the compound [26]) and [27] (hereinafter, referred to as the compound [27]) (here, the compound [26] and the compound [27] are diastereomers. Please see Table 7)

(1) 786 mg of the compound [25-3] was dissolved in 15 mL of chloroform, then 2.4 mL of acetone and 728 mg of sodium triacetoxyborohydride were added thereto, and the mixture was stirred overnight at 50° C. After standing to cool, to the reaction solution was added a saturated aqueous solution of sodium hydrogen carbonate, and the solution was extracted with chloroform. The obtained organic layer was washed with water and dried over anhydrous magnesium sulfate. The insolubles were filtered, the filtrate was concentrated under reduced pressure, and the resulting residue was purified by silica gel column chromatography (eluent: chloroform/methanol=100/0-93/7), to obtain 738 mg of a mixture of the title compounds [26] and [27]. The mixture was resolved using Chiralcel OD-H.

The optical resolution conditions are as follows.
column: Chiralcel OD-H (Daicel Chemical Industries Ltd.), diameter of 20 mm, length of 250 mm;
eluent: hexane/ethanol/diethylamine=85/15/0.1;
flow rate: 15 mL/min.

The obtained solution was concentrated under reduced pressure, and the residue was dissolved in a small amount of chloroform to be solidified with diethylether, thereby obtaining 175 mg of the title compound [26] (RT=17 minutes) as a pale yellow amorphous and 390 mg of the title compound [27] (RT=21 minutes) as a gray solid.

The spectral data of the compound [26] and the compound [27] are presented below.
Compound [26]

$^1$H-NMR (DMSO-d$_6$) δ: 9.98 (d, J=6.6 Hz, 1H×1/2), 8.95 (d, J=7.1 Hz, 1H×1/2), 8.90-8.88 (m, 1H), 8.73 (s, 1H×1/2), 8.72 (s, 1H×1/2), 8.70 (s, 1H×1/2), 8.61 (s, 1H×1/2), 7.42 (d, J=6.8 Hz, 1H×1/2), 7.35-7.32 (m, 2H+1H×1/2), 7.26-7.20 (m, 2H), 7.14 (t, J=7.1 Hz, 1H×1/2), 6.89 (t, J=7.1 Hz, 1H×1/2), 5.24 (quint, J=7.3 Hz, 1H×1/2), 5.06 (quint, J=7.1 Hz, 1H×1/2), 5.03-5.01 (m, 1H), 4.20-4.18 (m, 1H×1/2), 4.15-4.12 (m, H×1/2), 3.02 (q, J=7.6 Hz, 2H×1/2), 2.96 (q, J=7.6 Hz, 2H×1/2), 2.75-2.60 (m, 1H+H×1/2), 2.58-2.48 (m, 1H×1/2), 1.95-1.88 (m, 1H+1H×1/2), 1.76-1.73 (m, 1H+1H×1/2), 1.52 (d, J=7.3 Hz, 3H×1/2), 1.50 (d, J=7.1 Hz, 3H×1/2), 1.38-1.25 (m, 1H), 1.32 (t, J=7.6 Hz, 3H×1/2), 1.27 (t, J=7.6 Hz, 3H×1/2), 1.18-1.09 (m, 2H), 1.00-0.96 (m, 1H), 0.89-0.83 (m, 6H)

mass: 524 (M+1)$^+$.
Compound [27]

$^1$H-NMR (DMSO-d$_6$) δ: 9.98 (d, J=6.8 Hz, 1H×1/2), 8.96 (d, J=7.1 Hz, 1H×1/2), 8.91-8.88 (m, 1H), 8.73 (s, 1H), 8.71 (s, 1H×1/2), 8.60 (s, 1H×1/2), 7.43 (d, J=7.8 Hz, 1H×1/2), 7.35-7.33 (m, 2H+1H×1/2), 7.25-7.20 (m, 2H), 7.15 (t, J=6.8 Hz, 1H×1/2), 6.92 (t, J=6.8 Hz, 1H×1/2), 5.26-5.22 (m, 1H×1/2), 5.09-5.06 (m, 1H×1/2), 5.04-5.00 (m, 1H), 4.21-4.16 (m, 1H), 3.02 (q, J=7.3 Hz, 2H×1/2), 2.96 (q, J=7.3 Hz, 2H×1/2), 2.74-2.71 (m, 1H×1/2), 2.67-2.63 (m, 1H), 2.55-2.48 (m, 1H×1/2), 1.98-1.65 (m, 3H), 1.52 (d, J=7.1 Hz, 3H×1/2), 1.50 (d, J=7.3 Hz, 3H×1/2), 1.35-1.26 (m, 1H), 1.32 (t, J=7.6 Hz, 3H×1/2), 1.28 (t, J=7.6 Hz, 3H×1/2), 1.14-1.03 (m, 3H), 0.88 (d, J=6.3 Hz, 6H×1/2), 0.85 (d, J=6.6 Hz, 6H×1/2)

mass: 524 (M+1)$^+$.

Example 28

Synthesis of 2-[((1S)-1-{4-[(1-cyclopentylpiperidin-4-yl)(hydroxy)methyl]phenyl}ethyl)amino]-4-(8-ethylimidazo[1,2-a]pyridin-3-yl)pyrimidine-5-carbonitrile [28] (hereinafter, referred to as the compound [28])

5.5 mg of the title compound [28] was obtained as a yellow solid from 5 mg of the compound [25-3] and 5 μL of cyclopentanone according to the method of Example 1 7-(3).

The spectral data of the compound [28] are presented below.

$^1$H-NMR (CDCl$_3$) δ: 9.63 (d, J=8.0 Hz, 1H×1/6), 8.93 (s, 1H×1/6), 8.85 (d, J=8.0 Hz, 1H×5/6), 8.82-8.74 (m, 1H×5/6), 8.56 (s, 1H×1/6), 8.45 (s, 1H×5/6), 7.38-7.12 (m, 5H), 6.96 (t, J=8.0 Hz, 1H×1/6), 6.67-6.58 (m, 1H×5/6), 6.17 (d, J=8.0 Hz, 1H×5/6), 5.92-5.82 (m, 1H×1/6), 5.33 (brs, 1H×1/6), 5.12 (q, J=7.5 Hz, 1H×5/6), 4.40-4.37 (m, 1H), 3.07-2.84 (m, 4H), 2.40-2.36 (m, 1H), 1.97-1.95 (m, 1H), 1.83-1.20 (m, 21H)

mass: 550 (M+1)$^+$.

Example 29

Synthesis of 2-[((1S)-1-{4-[[1-(2,2-dimethylpropyl)piperidin-4-yl](hydroxy)methyl]phenyl}ethyl)amino]-4-(8-ethylimidazo[1,2-a]pyridin-3-yl)pyrimidine-5-carbonitrile [29] (hereinafter, referred to as the compound [29])

4 mg of the title compound [29] was obtained as a yellow solid from 5 mg of the compound [25-3] and 5 μL of trimethylacetaldehyde according to the method of Example 1 7-(3).

The spectral data of the compound [29] are presented below.

$^1$H-NMR (CDCl$_3$) δ: 9.63 (d, J=8.0 Hz, 1H×1/6), 8.93 (s, 1H×1/6), 8.86 (d, J=8.0 Hz, 1H×5/6), 8.81-8.72 (m, 1H×5/6), 8.56 (s, 1H×1/6), 8.45 (s, 1H×5/6), 7.40-7.13 (m, 5H), 6.96 (t, J=8.0 Hz, 1H×1/6), 6.67-6.58 (m, 1H×5/6), 6.15 (d, J=8.0 Hz, 1H×5/6), 5.92-5.82 (m, 1H×1/6), 5.34 (brs, 1H×1/6), 5.12 (q, J=7.5 Hz, 1H×5/6), 4.41-4.37 (m, 1H), 3.12-3.00 (m, 3H), 2.82-1.85 (m, 6H), 1.75-0.80 (m, 20H)

mass: 552 (M+1)$^+$.

Examples 30 and 31

Synthesis of 4-(8-ethylimidazo[1,2-a]pyridin-3-yl)-2-[((1S)-1-{4-[(1-ethylpiperidin-4-yl) (hydroxy)methyl]phenyl}ethyl)amino]pyrimidine-5-carbonitriles [30] (hereinafter, referred to as the compound [30]) and [31] ((hereinafter, referred to as the compound [31]) (here, the compound [30] and the compound [31] are diastereomers. Please see Table 7)

48 mg of a mixture of the title compounds [30] and [31] was obtained from 50 mg of the compound [25-3] and 30 μL of acetaldehyde according to the method of Example 1 7-(3). The mixture was resolved using Chiralcel OD-H.

The optical resolution conditions are as follows.

column: Chiralcel OD-H (Daicel Chemical Industries Ltd.), diameter of 20 mm, length of 250 mm;
eluent: hexane/ethanol/diethylamine=85/15/0.1;
flow rate: 15 mL/min.

The obtained solution was concentrated under reduced pressure, and the residue was dissolved in a small amount of chloroform to be solidified with diethylether, thereby obtaining 6 mg of the title compound [30] (RT=17.8 minutes) as a yellow solid and 14 mg of the title compound [31] (RT=23.1 minutes) as a yellow solid.

The spectral data of the compound [30] and the compound [31] are presented below. Compound [30]

$^1$H-NMR (CDCl$_3$) δ: 9.63 (d, J=8.0 Hz, 1H×1/6), 8.93 (s, 1H×1/6), 8.82 (s, 1H×5/6), 8.70 (d, J=8.0 Hz, 1H×5/6), 8.55 (s, 1H×5/6), 8.45 (s, 1H×5/6), 7.37-7.24 (m, 4H), 7.11 (d, J=8.0 Hz, 1H), 6.98 (t, J=8.0 Hz, 1H×1/6), 6.57 (t, J=8.0 Hz, 1H×5/6), 6.21 (d, J=8.0 Hz, 1H×5/6), 5.91 (d, J=8.0 Hz, 1H×1/6), 5.33 (brs, 1H×1/6), 5.10 (quint, J=7.5 Hz, 1H×5/6), 4.42 (d, J=7.5 Hz, 1H), 3.13-2.82 (m, 5H), 2.38 (q, J=7.5 Hz, 2H), 2.03-1.70 (m, 4H), 1.62 (d, J=7.5 Hz, 3H), 1.49-1.24 (m, 3H), 1.35 (t, J=7.5 Hz, 3H), 1.05 (t, J=7.5 Hz, 3H)
mass: 510 (M+1)$^+$.

Compound [31]

$^1$H-NMR (CDCl$_3$) δ: 9.62 (d, J=8.0 Hz, 1H×1/6), 8.87 (s, 1H×1/6), 8.81 (d, J=8.0 Hz, 1H×5/6), 8.80 (s, 1H×5/6), 8.54 (s, 1H×5/6), 8.36 (s, 1H×5/6), 7.39-7.22 (m, 4H), 7.12 (d, J=8.0 Hz, 1H), 6.93 (t, J=8.0 Hz, 1H×1/6), 6.66 (t, J=8.0 Hz, 1H×5/6), 6.47 (d, J=8.0 Hz, 1H×5/6), 6.04 (d, J=8.0 Hz, 1H×1/6), 5.34 (brs, 1H×1/6), 5.12 (quint, J=7.5 Hz, 1H×5/6), 4.36 (d, J=7.5 Hz, 1H), 3.11-2.78 (m, 5H), 2.34 (q, J=7.5 Hz, 2H), 2.02-1.60 (m, 4H), 1.63 (d, J=7.5 Hz, 3H), 1.43-1.15 (m, 3H), 1.36 (t, J=7.5 Hz, 3H), 1.04 (t, J=7.5 Hz, 3H)
mass: 510 (M+1)$^+$.

Example 32

Synthesis of 4-(8-ethylimidazo[1,2-a]pyridin-3-yl)-2-[((1S)-1-{4-[hydroxy(1-propylpiperidin-4-yl)methyl]phenyl}ethyl)amino]pyrimidine-5-carbonitrile [32] (hereinafter, referred to as the compound [32])

10 mg of the compound [25-3] was dissolved in 1 mL of N,N-dimethylformamide, then 5 mg of the potassium carbonate and 3 μL of 1-iodopropane were added, and the mixture was stirred for 2 hours at 50° C. After standing to cool, the insolubles were filtered, and the filtrate was concentrated under reduced pressure. The resulting residue was purified by preparative thin-layer chromatography to obtain 8 mg of the title compound [32] as a colorless solid.

The spectral data of the compound [32] are presented below.

$^1$H-NMR (CDCl$_3$) δ: 9.64 (d, J=8.0 Hz, 1H×1/6), 8.92 (s, 1H×1/6), 8.83 (d, J=8.0 Hz, 1H×5/6), 8.80-8.72 (m, 1H×5/6), 8.55 (s, 1H×1/6), 8.43 (s, J=8.0 Hz, 1H×5/6), 7.39-7.24 (m, 4H), 7.12 (d, J=8.0 Hz, 1H), 6.96 (t, J=8.0 Hz, 1H×1/6), 6.67-6.57 (m, 1H×5/6), 6.24 (d, J=8.0 Hz, 1H×5/6), 5.95-5.85 (m, 1H×1/6), 5.33 (brs, 1H×1/6), 5.11 (q, J=7.5 Hz, 1H×5/6), 4.44-4.37 (m, 1H), 3.12-2.74 (m, 5H), 2.22-2.18 (m, 2H), 1.98-1.62 (m, 7H), 1.46-1.20 (m, 8H), 0.85 (t, J=7.5 Hz, 3H)
mass: 524 (M+1)$^+$.

Example 33

Synthesis of 4-(6-bromo-8-ethylimidazo[1,2-a]pyridin-3-yl)-2-[((1S)-1-{4-[hydroxy (1-isopropylpiperidin-4-yl)methyl]phenyl}ethyl)amino]pyrimidine-5-carbonitrile [33] (hereinafter, referred to as the compound [33])

(1) To a solution prepared by dissolving 360 mg of 3-ethylpyridine-2-amine (synthesized according to the method disclosed in International Publication WO2006/025567, page 142) in a mixed solvent of 12 mL of 1,4-dioxane and 4 mL of water, 553 mg of N-bromosuccinimide was added at 0° C., and the mixture was stirred for 1.5 hours at the same temperature. Water was added to the reaction solution, which was extracted with ethyl acetate. The organic layer thus obtained was washed with water and saturated brine in that order, and dried over anhydrous sodium sulfate. Thereafter, the insolubles were filtered and the filtrate was concentrated under reduced pressure. The obtained residue was purified by silica gel column chromatography (eluent: hexane/ethyl acetate=75/25), to obtain 394 mg of 5-bromo-3-ethylpyridine-2-amine [33-1] (hereinafter, referred to as the compound [33-1]).

(2) 530 mg of 4-(6-bromo-8-ethylimidazo[1,2-a]pyridin-3-yl)-2-(methylthio)pyrimidine-5-carbonitrile [33-2] (hereinafter, referred to as the compound [33-2]) was obtained from 388 mg of the compound [33-1] according to the method of Example 1-(6).

(3) To a solution prepared by dissolving 2.98 g of the compound [25-1] in a mixed solvent of 30 mL of tetrahydrofuran and 10 mL of 2-propanol, 750 mg of a carbon catalyst of 20% palladium hydroxide was added, and the mixture was stirred overnight at room temperature under hydrogen atmosphere. The catalyst was filtered through celite, and the filtrate was concentrated under reduced pressure, to obtain 2.3 g of tert-butyl((1S)-1-{4-[hydroxy(piperidin-4-yl)methyl]phenyl}ethyl)carbamate [33-3] (hereinafter, referred to as the compound [33-3]). The compound [33-3] was used in the subsequent reaction without further purification.

(4) 2.14 g of tert-butyl((1S)-1-{4-[hydroxy(1-isopropylpiperidin-4-yl) methyl]phenyl}ethyl)carbamate [334] (hereinafter, referred to as the compound [334]) was obtained from 2.3 g of the compound [33-3] and 15 mL of acetone according to the method of Example 1 7-(3).

(5) 41 mg of the title compound [33] was obtained as a yellow amorphous from 70 mg of the compound [334] and 63 mg of the compound [33-2] according to the method of Example 1-(7).

The spectral data of the compound [33] are presented below.

$^1$H-NMR (CDCl$_3$) δ: 9.89 (s, 1H×5/6), 9.74 (s, 1H×1/6), 8.93 (s, 1H×5/6), 8.86 (s, 1H×1/6), 8.55 (s, 1H×1/6), 8.16 (s, 1H×5/6), 7.41-7.27 (m, 5H), 6.76 (d, J=8.0 Hz, 1H×5/6), 6.29 (d, J=8.0 Hz, 1H×1/6), 5.35 (brs, 1H×1/6), 5.27 (quint, J=7.5 Hz, 1H×5/6), 4.38 (d, J=7.5 Hz, 1H), 3.10 (q, J=7.5 Hz, 2H), 2.98-2.72 (m, 5H), 2.14-1.92 (m, 3H), 1.69 (d, J=7.5 Hz, 3H), 1.59-1.50 (m, 1H), 1.43-1.25 (m, 2H), 1.41 (t, J=7.5 Hz, 3H), 1.02 (d, J=7.5 Hz, 6H)

mass: 602, 604 (M+1)$^+$.

Example 34

Synthesis of 2-[((1S)-1-{4-[hydroxy(1-methyl-1,2,3, 6-tetrahydropyridin-4-yl) methyl]phenyl}ethyl) amino]-4-(8-methylimidazo[1,2-a]pyridin-3-yl)pyrimidine-5-carbonitrile [34] (hereinafter, referred to as the compound [34])

(1) To a solution prepared by dissolving 1.7 g of ethyl 1-methyl-1,2,3,6-tetrahydro-4-pyridinecarboxylate in 20 mL of tetrahydrofuran, 773 mg of lithium aluminum hydride was added, and the mixture was stirred for 1 hour at room temperature. The reaction solution was cooled to 0° C., and then sodium sulfate decahydrate was slowly added until there are no bubbles, and stirred overnight at room temperature. The insolubles were filtered and the filtrate was concentrated under reduced pressure. The obtained residue was dissolved in 40 mL of chloroform, then 2 g of manganese dioxide was added thereto, and the mixture was stirred overnight at room temperature. The insolubles were filtered through celite, the filtrate was concentrated under reduced pressure, and the resulting residue was purified by silica gel column chromatography (eluent: chloroform/methanol=100/0-90/10), to obtain 212 mg of 1-methyl-1,2,3,6-tetrahydropyridine-4-carboaldehyde [34-1] (hereinafter, referred to as the compound [34-1]).

(2) 177 mg of tert-butyl((1S)-1-{4-[hydroxy (1-methyl-1, 2,3,6-tetrahydropyridin-4-yl) methyl]phenyl}ethyl)carbamate [34-2] (hereinafter, referred to as the compound [34-2]) was obtained from 212 mg of the compound [34-1] and 300 mg of the compound [1-1] according to the method of Example 1 2-(1).

(3) 88 mg of the title compound [34] was obtained as a pale yellow solid from 177 mg of the compound [34-2] and 143 mg of the compound [1-6] according to the method of Example 1-(7).

The spectral data of the compound [34] are presented below.

$^1$H-NMR (CDCl$_3$) δ: 9.62 (d, J=7.2 Hz, 1H×1/5), 8.92-8.69 (m, 1H+1H×4/5), 8.55 (s, 1H×1/5), 8.47 (s, 1H×4/5), 7.74-6.58 (m, 6H), 6.30-6.20 (m, 1H×4/5), 5.98-5.80 (m, 1H+1H×1/5), 5.38-5.00 (m, 2H), 3.48-2.99 (m, 2H), 2.70-1.90 (m, 4H), 2.60 (s, 3H), 1.60 (d, J=6.8 Hz, 3H)

mass: 480 (M+1)$^+$.

Example 35

Synthesis of 4-(8-chloroimidazo[1,2-a]pyridin-3-yl)-2-[((1S)-1-{4-[hydroxy(1-methylpiperidin-4-yl)methyl]phenyl}ethyl)amino]pyrimidine-5-carbonitrile [35] (hereinafter, referred to as the compound [35])

44 mg of the title compound [35] was obtained as a white solid from 79 mg of the compound [9-1] and 100 mg of the compound [23-1] according to the method of Example 1-(7).

The spectral data of the compound [35] are presented below.

$^1$H-NMR (DMSO-d$_6$) δ: 10.06 (d, J=7.1 Hz, 1H×1/2), 9.04 (d, J=7.1 Hz, 1H×1/2), 8.96-8.94 (m, 1H), 8.78-8.74 (m, 1H+1H×1/2), 8.62 (s, 1H×1/4), 8.61 (s, 1H×1/4), 7.79 (d, J=7.1 Hz, 1H×1/2), 7.74-7.71 (m, 1H×1/2), 7.34-7.32 (m, 2H), 7.26-7.17 (m, 2H+1H×1/2), 6.95 (q, J=7.1 Hz, 1H×1/2), 5.24 (quint, J=7.6 Hz, 1H×1/2), 5.10-5.05 (m, 1H+1H×1/2), 4.20-4.13 (m, 1H), 2.74-2.66 (m, 1H+1H×1/2), 2.55-2.49 (m, 1H×1/2), 2.06 (s, 3H×1/2), 2.03 (s, 3H×1/2), 1.72-1.59 (m, 3H), 1.52 (d, J=7.1 Hz, 3H×1/2), 1.49 (d, J=7.1 Hz, 3H×1/2), 1.32-0.94 (m, 4H)

mass: 502, 504 (M+1)$^+$.

Example 36

Synthesis of 4-(8-cyclopropylimidazo[1,2-a]pyridin-3-yl)-2-[((1S)-1-{4-[hydroxy(1-methylpiperidin-4-yl)methyl]phenyl}ethyl)amino]pyrimidine-5-carbonitrile [36] (hereinafter, referred to as the compound [36])

(1) 750 mg of 4-(8-cyclopropylimidazo[1,2-a]pyridin-3-yl)-2-(methylthio)pyrimidine-5-carbonitrile [36-1] (hereinafter, referred to as the compound [36-1]) was obtained as an orange solid from 390 mg of 3-cyclopropylpyridine-2-amine (synthesized according to the method disclosed in International Publication WO2006/025567, page 142) according to the method of Example 1-(6).

(2) 66 mg of the title compound [36] was obtained as a yellow solid from 100 mg of the compound [36-1] and 110 mg of the compound [23-1] according to the method of Example 1-(7).

The spectral data of the compound [36] are presented below.

$^1$H-NMR (CD$_3$OD) δ: 9.85 (d, J=8.0 Hz, 1H×1/3), 8.78-8.73 (m, 1H×2/3), 8.68 (s, 1H×1/3), 8.61 (s, 1H×2/3), 8.43 (s, 1H×2/3), 8.36 (s, 1H×1/3), 7.40-7.25 (m, 4H), 6.93 (t, J=8.0 Hz, 1H×2/3), 6.87 (d, J=8.0 Hz, 1H×2/3), 6.71 (d, J=8.0 Hz, 1H×1/3), 6.67 (t, J=8.0 Hz, 1H×1/3), 5.23 (q, J=7.5 Hz, 1H×1/3), 5.01 (quint, J=7.5 Hz, 1H×2/3), 4.28-4.22 (m, 1H), 2.87-2.71 (m, 2H×2/3), 2.59-2.51 (m, 2H×1/3), 2.39-2.36 (m, 1H), 2.16 (s, 3H×1/3), 2.12 (s, 3H×2/3), 1.99-1.79 (m, 2H), 1.71-1.04 (m, 7H), 1.56 (d, J=7.5 Hz, 3H×2/3), 1.06 (d, J=7.5 Hz, 3H×1/3), 0.82-0.73 (m, 2H)

mass: 508 (M+1)$^+$.

Example 37

Synthesis of 4-(8-chloroimidazo[1,2-a]pyridin-3-yl)-2-[((1S)-1-{4-[(1-cyclopropylpiperidin-4-yl)(hydroxy)methyl]phenyl}ethyl)amino]pyrimidine-5-carbonitrile [37] (hereinafter, referred to as the compound [37])

(1) 1 g of the compound [25-1] was dissolved in 10 mL of methanol, then 200 mg of a carbon catalyst of 20% palladium hydroxide was added thereto, and the mixture was stirred for 1 hour at room temperature under hydrogen atmosphere. The catalyst was filtered through celite, and the filtrate was concentrated under reduced pressure, to obtain 710 mg of tert-butyl ((1S)-1-{4-[hydroxy(piperidin-4-yl) methyl] phenyl}ethyl)carbamate [37-1]. The compound [37-1] (hereinafter, referred to as the compound [37-1]) was used in the subsequent reaction without further purification.

(2) 710 mg of the compound [37-1] was dissolved in 10 mL of chloroform, then 1.2 mL of triethylamine and 744 μL of trifluoroacetic anhydride were added thereto, and the mixture was stirred overnight at room temperature. Water was added to the reaction solution, which was extracted with chloroform. The obtained organic layer was washed with saturated brine and dried over anhydrous sodium sulfate. Thereafter, the insolubles were filtered, and the filtrate was concentrated under reduced pressure. The resulting residue was purified by silica gel column chromatography (eluent: chloroform/methanol=100/0-97/3), to obtain 328 mg of tert-butyl[(1S)-1-(4-{hydroxy[1-(trifluoroacetyl) piperidin-4-yl]methyl}phenyl)ethyl]carbamate [37-2] (hereinafter, referred to as the compound [37-2]).

(3) 237 mg of 4-(8-chloroimidazo[1,2-a]pyridin-3-yl)-2-{[(1S)-1-(4-{hydroxy[1-(trifluoroacetyl) piperidin-4-yl]methyl}phenyl)ethyl]amino}pyrimidine-5-carbonitrile [37-3] (hereinafter, referred to as the compound [37-3]) was obtained from 328 mg of the compound [37-2] and 210 mg of the compound [9-1] according to the method of Example 1-(7).

(4) 237 mg of the compound [37-3] was dissolved in a mixed solvent of 3 mL of tetrahydrofuran and 1 mL of methanol, then 163 μL of 5N aqueous solution of sodium hydroxide was added thereto, and the mixture was stirred for 5 hours at 50° C. After standing to cool, the reaction solution was concentrated under reduced pressure, and the resulting residue was purified by silica gel column chromatography (eluent: chloroform/methanol=95/5-93/7), to obtain 156 mg of 4-(8-chloroimidazo[1,2-a]pyridin-3-yl)-2-[((1S)-1-{4-[hydroxy(piperidin-4-yl)methyl]phenyl}ethyl)amino]pyrimidine-5-carbonitrile [374] (hereinafter, referred to as the compound [374]).

(5) 28 mg of the compound [374] was dissolved in 2 mL of ethanol, then 58 mg of (1-ethoxycyclopropoxy) trimethylsilane, 33 μL of acetic acid, and 10 mg of molecular sieve 4A were added thereto, and the mixture was stirred for 10 minutes at room temperature. Thereafter, 11 mg of sodium cyanoborohydride was added and the mixture was heated for 6 hours under reflux. After standing to cool, the insolubles were filtered, to the filtrate was added an aqueous solution of sodium hydroxide, and the filtrate was extracted with chloroform. The obtained organic layer was dried over anhydrous sodium sulfate, the insolubles were filtered, and the filtrate was concentrated under reduced pressure. The resulting residue was purified by preparative thin-layer chromatography to obtain 20 mg of the title compound [37] as a pale yellow solid.

The spectral data of the compound [37] are presented below.

$^1$H-NMR (CDCl$_3$) δ: 9.68 (d, J=8.0 Hz, 1H×1/6), 8.90 (s, 1H×1/6), 8.63 (d, J=8.0 Hz, 1H×5/6), 8.57 (s, 1H×1/6), 8.44-8.34 (m, 1H×5/6), 8.42 (s, 1H×5/6), 7.47-7.26 (m, 5H), 6.92 (t, J=8.0 Hz, 1H×1/6), 6.57-6.43 (m, 2H×5/6), 6.05 (d, J=8.0 Hz, 1H×1/6), 5.34 (brs, 1H×1/6), 5.03-4.98 (m, 1H×5/6), 4.47-4.39 (m, 1H), 3.91-3.65 (brs, 1H), 3.09-2.91 (m, 2H), 2.16-1.48 (m, 8H), 1.37-1.12 (m, 3H), 0.49-0.36 (m, 4H)

mass: 528, 530 (M+1)$^+$.

Example 38

Synthesis of 4-(8-chloroimidazo[1,2-a]pyridin-3-yl)-2-({(1S)-1-[4-(hydroxy{1-[2-(methylsulfonyl)ethyl]piperidin-4-yl} methyl)phenyl]ethyl}amino)pyrimidine-5-carbonitrile [38] (hereinafter, referred to as the compound [38])

(1) 200 mg of 2-(methylsulfonyl)ethanol and 450 μL of triethylamine were dissolved in 5 mL of chloroform and cooled to 0° C., then 190 μL of methanesulfonyl chloride was added thereto, and the mixture was stirred for 3 hours at the same temperature. To the reaction solution was added a saturated aqueous solution of sodium hydrogen carbonate, and the solution was extracted with chloroform. The obtained organic layer was dried over anhydrous sodium sulfate, then the insolubles were filtered, and the filtrate was concentrated under reduced pressure, to obtain 2-(methylsulfonyl) ethylmethanesulfonate [38-1] (hereinafter, referred to as the compound [38-1]). The compound [38-1] was used in the subsequent reaction without further purification.

(2) 5 mg of the compound [374] was dissolved in a mixed solvent of 0.5 mL of chloroform and 0.5 μL of methanol, and 4.5 μL of triethylamine and 6 mg of the compound [38-1] were added thereto. After a 30 minutes stirring at room temperature, the resultant was purified by preparative thin-layer chromatography to obtain 6 mg of the title compound [38] as a colorless solid.

The spectral data of the compound [38] are presented below.

$^1$H-NMR (CDCl$_3$) δ: 9.70 (d, J=8.0 Hz, 1H×1/6), 8.95 (s, 1H×1/6), 8.69 (d, J=8.0 Hz, 1H×5/6), 8.59 (s, 1H×1/6), 8.50 (s, 1H×5/6), 8.50-8.42 (m, 1H×5/6), 7.53-7.26 (m, 5H), 6.96 (t, J=8.0 Hz, 1H×1/6), 6.58-6.46 (m, 1H×5/6), 6.25-6.23 (m, 1H×5/6), 5.95 (d, J=8.0 Hz, 1H×1/6), 5.34 (brs, 1H×1/6), 5.05-5.00 (m, 1H×5/6), 4.47-4.39 (m, 1H), 3.55-3.26 (brs, 1H), 3.12-3.09 (m, 2H), 3.01 (s, 3H), 2.97-2.94 (m, 1H), 2.83-2.79 (m, 3H), 2.09-1.84 (m, 4H), 1.64-1.61 (m, 1H), 1.46-1.21 (m, 5H)

mass: 594, 596 (M+1)$^+$.

Example 39

Synthesis of 4-[8-(difluoromethyl)imidazo[1,2-a]pyridin-3-yl]-2-[((1S)-1-{4-[hydroxy(1-isopropylpiperidin-4-yl)methyl]phenyl}ethyl)amino]pyrimidine-5-carbonitrile [39] (hereinafter, referred to as the compound [39])

22 mg of the title compound [39] was obtained as a yellow solid from 40 mg of the compound [10-2] and 47 mg of the compound [334] according to the method of Example 1-(7).

The spectral data of the compound [39] are presented below.

$^1$H-NMR (CDCl$_3$) δ: 9.85 (d, J=8.0 Hz, 1H×1/6), 8.93 (s, 1H×1/6), 8.89-8.82 (m, 1H×5/6), 8.77-8.73 (m, 1H×5/6), 8.58 (s, 1H×1/6), 8.44 (d, J=8.0 Hz, 1H×5/6), 7.71 (d, J=8.0 Hz, 1H×1/6), 7.59-7.54 (m, 1H×5/6), 7.41-7.21 (m, 4H), 7.12-7.09 (m, 1H×1/6), 6.79-6.64 (m, 1H×5/6), 6.45 (d, J=8.0 Hz, 1H×5/6), 6.12-6.02 (m, 1H×1/6), 5.34 (brs, 1H×1/6), 5.10-5.03 (m, 1H×5/6), 4.44-4.39 (m, 1H), 2.93-1.88 (m, 8H), 1.64-1.58 (m, 4H), 1.40-1.13 (m, 3H), 1.00 (d, J=7.5 Hz, 6H)

mass: 546 (M+1)$^+$.

Example 40

Synthesis of 4-(8-chloroimidazo[1,2-a]pyridin-3-yl)-2-{[(1S)-1-(4-{hydroxy[1-(2-hydroxyethyl) piperidin-4-yl]methyl}phenyl)ethyl]amino}pyrimidine-5-carbonitrile [40] (hereinafter, referred to as the compound [40])

16 mg of the title compound [40] was obtained as a yellow solid from 20 mg of the compound [374] and 5 μL of 2-bromoethanol according to the method of Example 2 5-(4).

The spectral data of the compound [40] are presented below.

$^1$H-NMR (CD$_3$OD) δ: 10.08 (d, J=8.0 Hz, 1H×1/3), 8.90-8.87 (m, 1H×2/3), 8.76 (s, 1H×1/3), 8.65 (s, 1H×2/3), 8.55 (s, 1H×2/3), 8.49 (s, 1H×1/3), 7.63 (d, J=8.0 Hz, 1H×1/3), 7.55 (t, J=8.0 Hz, 1H×2/3), 7.40-7.26 (m, 4H), 7.08 (t, J=8.0 Hz, 1H×1/3), 6.85-6.80 (m, 1H×2/3), 5.27 (q, J=7.5 Hz, 1H×1/3), 5.07 (q, J=7.5 Hz, 1H×2/3), 4.30-4.25 (m, 1H), 3.64-3.58 (m,

2H), 2.97-2.85 (m, 2H×2/3), 2.75-2.67 (m, 2H×1/3), 2.47-2.40 (m, 2H), 1.99-1.74 (m, 3H), 1.58 (d, J=7.5 Hz, 3H), 1.58-1.03 (m, 4H)

mass: 532, 534 (M+1)$^+$.

Examples 41 and 42

Synthesis of 4-(8-ethylimidazo[1,2-a]pyridin-3-yl)-2-{[(1S)-1-(4-{hydroxy[(3R)-1-methylpiperidin-3-yl]methyl}phenyl)ethyl]amino}pyrimidine-5-carbonitrile [41] (hereinafter, referred to as the compound [41]) and 4-(8-ethylimidazo[1,2-a]pyridin-3-yl)-2-{[(1S)-1-(4-{hydroxy[(3S)-1-methylpiperidin-3-yl]methyl}phenyl)ethyl]amino}pyrimidine-5-carbonitrile [42] (hereinafter, referred to as the compound [42]) (here, the compound [41] and the compound [42] are diastereomers. Please see Table 9)

(1) 11.8 g of benzyl3-[(4-{(1S)-1-[(tert-butoxycarbonyl)amino]ethyl}phenyl)(hydroxy)methyl]piperidine-1-carboxylate [41-1] (hereinafter, referred to as the compound [41-1]) was obtained as a mixture of four isomers, from 15 g of benzyl(3R)-3-formylpiperidine-1-carboxylate (synthesized according to the method disclosed in International Publication WO02/46157) and 16.6 g of the compound [1-1] according to the method of Example 1 2-(1).

(2) 6.81 g of benzyl3-[[4-((1S)-1-{[5-cyano-4-(8-ethylimidazo[1,2-a]pyridin-3-yl) pyrimidin-2-yl]amino}ethyl)phenyl](hydroxy)methyl]piperidine-1-carboxylate [41-2] (hereinafter, referred to as the compound [41-2]) was obtained from 7.56 g of the compound [5-6] and 11.8 g of the compound [41-1] according to the method of Example 1-(7).

(3) 5 g of 4-(8-ethylimidazo[1,2-a]pyridin-3-yl)-2-[((1S)-1-{4-[hydroxy(piperidin-3-yl) methyl]phenyl}ethyl)amino]pyrimidine-5-carbonitrile [41-3] was obtained from 6.81 g of the compound [41-2] according to the method of Example 1 7-(2). The obtained compound [41-3] which is a mixture of four isomers was purified by silica gel column chromatography (eluent: chloroform/methanol=100/0-90/10), thereby obtaining 2.21 g of a low polarity compound (compound that eluted first under the above condition) [41-3a] (hereinafter, referred to as the compound [41-3a]) and 1.88 g of a high polarity compound (compound that eluted afterwards under the above condition) [41-3b] (hereinafter, referred to as the compound [41-3b]) each as a mixture of two isomers. Here, the compound [41-3a] is a mixture of precursors of the compounds [41] and [42], respectively, and the compound [41-3b] is a mixture of precursors of compounds [43] and [44] described later, respectively.

(4) 1.89 g of a mixture of the title compounds [41] and [42] was obtained from 2.21 g of the compound [41-3a] according to the method of Example 1 7-(3). The mixture was resolved using Chiralpack AD.

The optical resolution conditions are as follows.
column: Chiralpack AD (Daicel Chemical Industries Ltd.), diameter of 50 mm, length of 5,000 mm;
eluent: hexane/2-propanol/diethylamine=65/35/0.1;
flow rate: 100 mL/min.

The obtained solution was concentrated under reduced pressure, and the residue was dissolved in a small amount of chloroform to be solidified with diethylether, thereby obtaining 892 mg of the title compound [41] (RT=15.5 minutes) as a pale yellow solid and 298 mg of the title compound [42] (RT=35 minutes) as a pale yellow solid.

The spectral data of the compound [41] and the compound [42] are presented below.

Compound [41]
$^1$H-NMR (DMSO-d$_6$) δ: 9.98 (d, J=6.8 Hz, 1H×1/3), 8.96 (d, J=6.8 Hz, 1H×2/3), 8.89-8.86 (m, 1H), 8.73 (s, 1H), 8.70 (s, 1H×1/3), 8.61 (s, 1H×2/3), 7.41-7.16 (m, 5H+1H×1/3), 6.89 (t, J=7.1 Hz, 1H×2/3), 5.30-5.00 (m, 2H), 4.29-4.19 (m, 1H), 3.32 (s, 3H), 3.02-2.93 (m, 2H), 2.65-2.50 (m, 1H), 2.32-2.28 (m, 1H×1/3), 2.12-2.06 (m, 1H×2/3), 1.80-1.40 (m, 9H), 1.32-1.20 (m, 3H)

mass: 496 (M+1)$^+$.

Compound [42]
$^1$H-NMR (DMSO-d$_6$) δ: 9.90 (m, 1H×2/5), 8.98-8.60 (m, 3H+1H×3/5), 7.60-6.85 (m, 6H), 5.18-5.05 (m, 2H), 4.30-4.20 (m, 1H), 3.34 (s, 3H), 3.20-2.80 (m, 2H), 2.70-2.50 (m, 1H), 2.18-1.45 (m, 10H), 1.40-1.20 (m, 3H)

mass: 496 (M+1)$^+$.

Examples 43 and 44

Synthesis of 4-(8-ethylimidazo[1,2-a]pyridin-3-yl)-2-{[(1S)-1-(4-{hydroxy[(3R)-1-methylpiperidin-3-yl]methyl}phenyl)ethyl]amino}pyrimidine-5-carbonitrile [43] (hereinafter, referred to as the compound [43]) and 4-(8-ethylimidazo[1,2-a]pyridin-3-yl)-2-{[(1S)-1-(4-{hydroxy[(3S)-1-methylpiperidin-3-yl]methyl}phenyl)ethyl]amino}pyrimidine-5-carbonitrile [44] (hereinafter, referred to as the compound [44]) (here, the compound [43] and the compound [44] are diastereomers. Please see Table 9)

921 mg of a mixture of the title compounds [43] and [44] was obtained from 917 mg of the compound [41-3b] according to the method of Example 1 7-(3). The mixture was resolved using Chiralcel OD-H.

The optical resolution conditions are as follows.
column: Chiralcel OD-H (Daicel Chemical Industries Ltd.), diameter of 20 mm, length of 250 mm;
eluent: hexane/ethanol/diethylamine=85/15/0.1;
flow rate: 20 mL/min.

The obtained solution was concentrated under reduced pressure, and the residue was dissolved in a small amount of chloroform to be solidified with diethylether, thereby obtaining 510 mg of the title compound [43] (RT=16.8 minutes) as a pale yellow solid and 253 mg of the title compound [44] (RT=23.1 minutes) as a yellow solid.

The spectral data of the compound [43] and the compound [44] are presented below.

Compound [43]
$^1$H-NMR (DMSO-d$_6$) δ: 10.00 (d, J=6.8 Hz, 1H×2/5), 8.98 (d, J=6.8 Hz, 1H×3/5), 8.92-8.87 (m, 1H), 8.76 (s, 1H), 8.73 (s, 1H×2/5), 8.63 (s, 1H×3/5), 7.46-7.15 (m, 5H+1H×2/5), 6.90 (t, J=7.1 Hz, 1H×3/5), 5.25-5.05 (m, 2H), 4.22-4.20 (m, 1H), 3.34 (s, 3H), 3.10-2.80 (m, 2H), 2.70-2.50 (m, 1H), 2.15-1.60 (m, 10H), 1.39-1.22 (m, 3H)

mass: 496 (M+1)$^+$.

Compound [44]
$^1$H-NMR (DMSO-d$_6$) δ: 9.90 (m, 1H×2/5), 9.00-8.60 (m, 3H+1H×3/5), 7.40-6.80 (m, 6H), 5.20-5.00 (m, 2H), 4.20-4.00 (m, 1H), 3.30 (s, 3H), 3.40-3.20 (m, 2H), 2.70-1.40 (m, 8H), 1.40-1.20 (m, 5H)

mass: 496 (M+1)$^+$.

Example 45

Synthesis of 4-(8-ethylimidazo[1,2-a]pyridin-3-yl)-2-[((1S)-1-{4-[(1-ethylpiperidin-3-yl) (hydroxy)methyl]phenyl}ethyl)amino]pyrimidine-5-carbonitrile [45] (hereinafter, referred to as the compound [45])

23 mg of the title compound [45] was obtained as a white solid from 25 mg of the compound [41-3a] and acetaldehyde according to the method of Example 1 7-(3).

The spectral data of the compound [45] are presented below.
$^1$H-NMR (CDCl$_3$) δ: 9.62-9.60 (m, 1H×1/5), 8.95-8.75 (m, 1H+1H×4/5), 8.56 (s, 1H×1/5), 8.42 (s, 1H×4/5), 7.40-6.60 (m, 6H), 6.30-6.25 (m, 1H×4/5), 5.95-5.90 (m, 1H×1/5), 5.35-4.85 (m, 2H), 3.15-3.00 (m, 2H), 2.70-2.30 (m, 6H), 2.00-1.80 (m, 2H), 1.63 (d, J=7.0 Hz, 3H), 1.55-1.20 (m, 6H), 1.10-1.00 (m, 3H)
mass: 510 (M+1)$^+$.

Example 46

Synthesis of 4-(8-ethylimidazo[1,2-a]pyridin-3-yl)-2-[((1S)-1-{4-[(1-ethylpiperidin-3-yl) (hydroxy)methyl]phenyl}ethyl)amino]pyrimidine-5-carbonitrile [46] (hereinafter, referred to as the compound [46])

28 mg of the title compound [46] was obtained as a white solid from 36 mg of the compound [41-3b] and acetaldehyde according to the method of Example 1 7-(3).
The spectral data of the compound [46] are presented below.
$^1$H-NMR (CDCl$_3$) δ: 9.61-9.59 (m, 1H×1/5), 8.90-8.75 (m, 1H+1H×4/5), 8.52 (s, 1H×1/5), 8.43 (s, 1H×4/5), 7.40-6.60 (m, 6H), 6.38-6.32 (m, 1H×4/5), 5.95-5.90 (m, 1H×1/5), 5.35-5.10 (m, 1H), 4.68-4.52 (m, 11H), 3.12-3.00 (m, 2H), 2.80-1.70 (m, 8H), 1.62 (d, J=7.0 Hz, 3H), 1.60-1.20 (m, 6H), 1.10-1.00 (m, 3H)
mass: 510 (M+1)$^+$.

Example 47

Synthesis of 4-(8-ethylimidazo[1,2-a]pyridin-3-yl)-2-[((1S)-1-{4-[(1-isopropylpiperidin-3-yl)(hydroxy)methyl]phenyl}ethyl)amino]pyrimidine-5-carbonitrile [47] (hereinafter, referred to as the compound [47])

23 mg of the title compound [47] was obtained as a white solid from 25 mg of the compound [41-3a] and acetone according to the method of Example 1 7-(3).
The spectral data of the compound [47] are presented below.
$^1$H-NMR (CDCl$_3$) δ: 9.61 (m, 1H×1/5), 8.92-8.70 (m, 1H+1H×4/5), 8.56 (s, 1H×1/5), 8.48 (s, 1H×4/5), 7.40-6.60 (m, 6H), 6.22-6.20 (m, 1H×4/5), 5.95-5.85 (m, 1H×1/5), 5.38-5.00 (m, 2H), 3.15-3.00 (m, 2H), 2.95-2.30 (m, 5H), 2.00-1.80 (m, 2H), 1.63 (d, J=7.0 Hz, 3H), 1.55-1.10 (m, 6H), 1.03-1.00 (m, 6H)
mass: 524 (M+1)$^+$.

Example 48

Synthesis of 4-(8-ethylimidazo[1,2-a]pyridin-3-yl)-2-[((1S)-1-{4-[(1-isopropylpiperidin-3-yl)(hydroxy)methyl]phenyl}ethyl)amino]pyrimidine-5-carbonitrile [48] (hereinafter, referred to as the compound [48])

21 mg of the title compound [48] was obtained as a white solid from 36 mg of the compound [41-3b] and acetone according to the method of Example 1 7-(3).
The spectral data of the compound [48] are presented below.
$^1$H-NMR (CDCl$_3$) δ: 9.62-9.60 (m, 1H×1/5), 8.95-8.78 (m, 1H+1H×4/5), 8.56 (s, 1H×1/5), 8.45 (s, 1H×4/5), 7.40-6.60 (m, 6H), 6.22-6.20 (m, 1H×4/5), 5.95-5.85 (m, 1H×1/5), 5.35-5.10 (m, 1H), 5.05-4.68 (m, 1H), 3.18-3.00 (m, 2H), 2.80-2.38 (m, 5H), 2.05-1.80 (m, 2H), 1.63 (d, J=7.0 Hz, 3H), 1.60-1.20 (m, 6H), 1.05-0.98 (m, 6H)
mass: 524 (M+1)$^+$.

Example 49

Synthesis of 2-[((1S)-1-{4-[hydroxy(1-methyl-1,2,5,6-tetrahydropyridin-3-yl)methyl]phenyl}ethyl)amino]-4-(8-methylimidazo[1,2-a]pyridin-3-yl)pyrimidine-5-carbonitrile [49] (hereinafter, referred to as the compound [49])

(1) 780 mg of arecaidine monohydrochloride, 3.07 mL of triethylamine, 644 mg of N,O-Dimethylhydroxylamine hydrochloride, 1.26 g of 1-ethyl-3-(3-dimethylaminopropyl)carbodiimide hydrochloride, and 1.01 g of 1-hydroxybenzotriazole monohydrate, were dissolved in 10 mL of chloroform, and the mixture was stirred overnight at room temperature. Water was added to the reaction solution, and the solution was extracted with chloroform. The obtained organic layer was washed with water and saturated brine in that order, and dried over anhydrous sodium sulfate. The insolubles were filtered, the filtrate was concentrated under reduced pressure, and the resulting residue was purified by silica gel column chromatography (eluent: chloroform/methanol=100/0-90/10), to obtain 857 mg of N-methoxy-N,1-dimethyl-1,2,5,6-tetrahydropyridine-3-carboxyamide [49-1] (hereinafter, referred to as the compound [49-1]).
(2) 162 mg of tert-butyl((1S)-1-{4-[(1-methyl-1,4,5,6-tetrahydropyridin-3-yl)carbonyl]phenyl}ethyl)carbamate [49-2] (hereinafter, referred to as the compound [49-2]) was obtained from 299 mg of the compound [49-1] and 300 mg of the compound [1-1] according to the method of Example 2-(2).
(3) 40 mg of 4-(8-methylimidazo[1,2-a]pyridin-3-yl)-2-[((1S)-1-{4-[(1-methyl-1,2,5,6-tetrahydropyridin-3-yl)carbonyl]phenyl}ethyl)amino]pyrimidine-5-carbonitrile [49-3] (hereinafter, referred to as the compound [49-3]) was obtained from 162 mg of the compound [49-2] and 100 mg of the compound [1-6] according to the method of Example 1-(7).
(4) 40 mg of the compound [49-3] was dissolved in a mixed solvent of 5 mL of tetrahydrofuran and 1 mL of methanol and cooled to 0° C. Thereafter, 10 mg of sodium boronhydride was added, and the mixture was stirred for 1 hour with heating to room temperature. To the reaction solution was added a saturated aqueous solution of sodium hydrogen carbonate, and the solution was extracted with chloroform. The obtained organic layer was washed with saturated brine and dried over anhydrous sodium sulfate. The insolubles were filtered, the filtrate was concentrated under reduced pressure, and the resulting residue was purified by preparative thin-layer chromatography. The obtained crude and purified product was dissolved in a small amount of chloroform and solidified with hexane to obtain 7 mg of the title compound [49] as a white solid.
The spectral data of the compound [49] are presented below.
$^1$H-NMR (CDCl$_3$) δ: 9.62 (d, J=7.2 Hz, 1H×1/5), 8.95-8.72 (m, 1H+1H×4/5), 8.55 (s, 1H×1/5), 8.50 (s, 1H×4/5), 7.45-6.55 (m, 6H), 6.10-6.05 (m, 1H×4/5), 5.90-5.80 (m, 1H+1H×1/5), 5.35-5.08 (m, 2H), 3.05-2.90 (m, 2H), 2.80-2.60 (m, 2H), 2.62 (s, 3H), 2.40-2.20 (m, 2H), 1.62 (d, J=6.8 Hz, 3H)
mass: 480 (M+1)$^+$.

Examples 50 and 51

Synthesis of 2-{[(1S)-1-(4-{hydroxy[(2S)-1-methylpyrrolidin-2-yl]methyl}phenyl)ethyl]amino}-4-(8-methylimidazo[1,2-a]pyridin-3-yl)pyrimidine-5-carbonitriles [50] (hereinafter, referred to as the compound [50]) and [51] (hereinafter, referred to as the compound [51]) (here, the compound [50] and the compound [51] are diastereomers. Please see Table 10)

(1) 95 mg of benzyl(2S)-2-[(4-{(1S)-1-[(tert-butoxycarbonyl)amino]ethyl}phenyl)(hydroxy)methyl]pyrrolidine-1-carboxylate [50-1] (hereinafter, referred to as the compound [50-1]) was obtained from 467 mg of benzyl(2S)-2-formylpyrrolidine-1-carboxylate (synthesized according to the method disclosed in Bioorg. Med. Chem., 2003.11. 3153-3164) and 500 mg of the compound [1-1] according to the method of Example 1 2-(1).

(2) 68 mg of benzyl(2S)-2-[[4-((1S)-1-{[5-cyano-4-(8-methylimidazo[1,2-a]pyridin-3-yl)pyrimidin-2-yl]amino}ethyl)phenyl] (hydroxy)methyl]pyrrolidine-1-carboxylate [50-2] (hereinafter, referred to as the compound [50-2]) was obtained from 93 mg of the compound [50-1] and 48 mg of the compound [1-6] according to the method of Example 1-(7).

(3) 10 mg of 2-{[(1S)-1-(4-{hydroxy[(2S)-pyrrolidin-2-yl]methyl}phenyl)ethyl]amino}-4-(8-methylimidazo[1,2-a]pyridin-3-yl) pyrimidine-5-carbonitrile [50-3] (hereinafter, referred to as the compound [50-3]) was obtained from 30 mg of the compound [50-2] according to the method of Example 1 7-(2).

(4) 7 mg of the compound [50-3] was dissolved in 1 mL of chloroform, then 4 mg of 37% formaldehyde solution and 10 mg of sodium triacetoxyborohydride were added thereto, and the mixture was stirred for 2.5 hours at room temperature. To the reaction mixture was added a saturated aqueous solution of sodium hydrogen carbonate, and the mixture was extracted with chloroform. The obtained organic layer was washed with saturated brine and dried over anhydrous sodium sulfate. The insolubles were filtered, the filtrate was concentrated under reduced pressure, and the resulting residue was purified by preparative thin-layer chromatography (developing solvent: chloroform/methanol=20/1), to resolve the compound [50] and the compound [51] which are diastereomers. According to the above purification condition, 3 mg of the title compound [50], which is a low polarity compound, and 2 mg of the title compound [51], which is a high polarity compound, were obtained both as a white solid.

The spectral data of the compound [50] and compound [51] are presented below.

Compound [50]

$^1$H-NMR (CDCl$_3$) δ: 9.63 (d, J=6.3 Hz, 1H×1/5), 8.94 (s, 1H×1/5), 8.89 (s, 1H×4/5), 8.76 (d, J=6.3 Hz, 1H×4/5), 8.57 (s, 1/5), 8.53 (s, 1H×4/5), 7.42-7.15 (m, 5H), 6.64-6.60 (m, 1H), 6.07-6.05 (m, 1H×4/5), 5.88-5.80 (m, 1H×1/5), 5.36-5.25 (m, 1H+1H×1/5), 5.15-5.11 (m, 1H×4/5), 4.94 (s, 1H), 2.65-2.40 (m, 3H), 2.69 (s, 1H×3/5), 2.64 (s, 2H+1H×2/5), 2.15-1.70 (m, 6H), 2.53 (s, 3H), 1.82-1.64 (m, 4H), 1.63 (d, J=7.2 Hz, 3H)

mass: 468 (M+1)$^+$.

Compound [51]

$^1$H-NMR (CDCl$_3$) δ: 9.64-9.63 (m, 1H×1/5), 8.94-8.88 (m, 1H+1H×4/5), 8.53 (s, 1H×1/5), 8.52 (s, 1H×4/5), 7.43-7.16 (m, 5H), 6.66-6.62 (m, 1H), 6.04-6.02 (m, 1H×4/5), 5.83-5.82 (m, 1H×1/5), 5.18-5.13 (m, 1H×4/5), 4.55-4.54 (m, 1H), 3.40-3.20 (m, 1H), 2.69 (s, 1H×3/5), 2.65 (s, 2H+1H×2/5), 2.57-2.45 (m, 6H), 2.38 (s, 3H), 1.96-1.55 (m, 4H), 1.63 (d, J=7.2 Hz, 3H)

mass: 468 (M+1)$^+$.

Examples 52 and 53

Synthesis of 2-{[(1S)-1-(4-{hydroxy[(2R)-1-methylpyrrolidin-2-yl]methyl}phenyl)ethyl]amino}-4-(8-methylimidazo[1,2-a]pyridin-3-yl)pyrimidine-5-carbonitriles [52] (hereinafter, referred to as the compound [52]) and [53] (hereinafter, referred to as the compound [53]) (here, the compound [52] and the compound [53] are diastereomers. Please see Table 10)

(1) 337 mg of benzyl(2R)-2-[(4-{(1S)-1-[(tert-butoxycarbonyl)amino]ethyl}phenyl)(hydroxy)methyl]pyrrolidine-1-carboxylate [52-1] (hereinafter, referred to as the compound [52-1]) was obtained from 1.06 g of benzyl(2R)-2-formylpyrrolidine-1-carboxylate (synthesized according to the method disclosed in Bioorg. Med. Chem., 2003.11. 3153-3164) and 1.14 g of the compound [1-1] according to the method of Example 1 2-(1).

(2) 18 mg of the title compound [52] and 19 mg of the title compound [53] were obtained both as a white solid from 335 mg of the compound [52-1] and 173 mg of the compound [1-6] according to the methods of Example 50, 51-(2) to (4). According to the purification conditions mentioned in Examples 50, 51-(4), the compound [52] was a low polarity compound and the compound [53] was a high polarity compound.

The spectral data of the compound [52] and compound [53] are presented below.

Compound [52]

$^1$H-NMR (CDCl$_3$) δ: 9.65-9.50 (m, 1H×1/5), 8.96-8.87 (m, 1H+1H×4/5), 8.58 (s, 1H×1/5), 8.51 (s, 1H×4/5), 7.42-6.93 (m, 5H), 6.67-6.52 (m, 1H), 6.11-6.10 (m, 1H×4/5), 5.88-5.80 (m, 1H×1/5), 5.36-5.29 (m, 1H×1/5), 5.16-5.13 (m, 1H×4/5), 4.91-4.90 (m, 1H), 3.25-3.15 (m, 1H), 2.68 (s, 1H×3/5), 2.64 (s, 2H+1H×2/5), 2.50 (s, 1H×3/5), 2.48 (s, 2H+1H×2/5), 1.79-1.52 (m, 4H), 1.61 (d, J=7.2 Hz, 3H)

mass: 468 (M+1)$^+$.

Compound [53]

$^1$H-NMR (CDCl$_3$) δ: 9.65 (d, J=6.8 Hz, 1H×1/5), 8.95 (s, 1H×1/5), 8.91 (s, 1H×4/5), 8.79 (d, J=6.8 Hz, 1H×4/5), 8.56 (s, 1H×1/5), 8.53 (s, 1H×4/5), 7.43-7.15 (m, 5H), 6.66-6.64 (m, 1H), 6.04-6.03 (m, 1H×4/5), 5.85-5.82 (m, 1H×1/5), 5.33-5.30 (m, 1H×1/5), 5.18-5.10 (m, 1H×4/5), 4.45-4.44 (m, 1H), 3.22-3.16 (m, 1H), 2.89-2.77 (m, 1H), 2.69 (s, 1H×3/5), 2.64 (s, 2H+1H×2/5), 2.58-2.34 (m, 2H), 2.29 (s, 3H), 1.92-1.52 (m, 4H), 1.62 (d, J=7.2 Hz, 3H)

mass: 468 (M+1)$^+$.

Examples 54 and 55

Synthesis of 4-(8-ethylimidazo[1,2-a]pyridin-3-yl)-2-{[(1S)-1-(4-{hydroxy[(2R)-1-methylpyrrolidin-2-yl]methyl}phenyl)ethyl]amino}pyrimidine-5-carbonitriles [54] (hereinafter, referred to as the compound [54]) and [55] (hereinafter, referred to as the compound [55]) (here, the compound [54] and the compound [55] are diastereomers. Please see Table 10)

(1) 300 mg of the compound [52-1] was dissolved in a mixed solvent of 6 mL of tetrahydrofuran and 6 mL of methanol, then 100 mg of a carbon catalyst of 20% palladium hydroxide was added thereto, and the mixture was stirred for 2.5 hours at room temperature under hydrogen atmosphere. The catalyst was filtered through celite and the filtrate was concentrated under reduced pressure. The resulting residue was dissolved in 6 mL of tetrahydrofuran, then 147 μL of 37% formaldehyde solution and 420 mg of sodium triacetoxyborohydride were added thereto, and the mixture was stirred for 1.5 hours at room temperature. To the reaction solution was added a saturated aqueous solution of sodium hydrogen carbonate, the solution was extracted with a mixed solvent of chloroform and methanol (mixing ratio: 9/1), and the resulting organic layer was washed with saturated brine and dried over anhydrous sodium sulfate. Thereafter, the insolubles were filtered, and the filtrate was concentrated under reduced pressure, to obtain 220 mg of tert-butyl[(1S)-1-(4-{hydroxy[(2R)-1-methylpyrrolidin-2-yl]methyl}phenyl)ethyl]carbamate [54-1] (hereinafter, referred to as the compound [54-1]).

(2) 15 mg of the title compound [54] and 13 mg of the title compound [55] were obtained both as a colorless solid from 73 mg of the compound [54-1] and 65 mg of the compound [5-6] according to the method of Example 1-(7). According to the purification conditions mentioned in Example 1-(7), the compound [54] was a low polarity compound and the compound [55] was a high polarity compound.

The spectral data of the compound [54] and compound [55] are presented below.

Compound [54]

$^1$H-NMR (CDCl$_3$) δ: 9.67-9.60 (m, 1H×1/5), 8.95-8.89 (m, 1H+1H×4/5), 8.57 (s, 1H×1/5), 8.52 (s, 1H×4/5), 7.45-7.17 (m, 5H), 6.70-6.67 (m, 1H), 6.03-6.02 (m, 1H×4/5), 5.85-5.76 (m, 1H×1/5), 5.35-5.34 (m, 1H×1/5), 5.16-5.13 (m, 1H×4/5), 4.88-4.87 (m, 1H), 3.14-3.05 (m, 3H), 2.46 (s, 3H), 2.53-2.24 (m, 3H), 1.75-1.51 (m, 4H), 1.63 (d, J=6.8 Hz, 3H), 1.37 (t, J=7.8 Hz, 3H)

mass: 482 (M+1)$^+$.

Compound [55]

$^1$H-NMR (CDCl$_3$) δ: 9.64 (d, J=6.8 Hz, 1H×1/5), 8.94 (s, 1H×1/5), 8.89 (s, 1H×4/5), 8.80 (d, J=6.8 Hz, 1H×4/5), 8.56 (s, 1H×1/5), 8.52 (s, 1H×4/5), 7.43-7.16 (m, 5H), 6.70-6.66 (m, 1H), 6.04-6.03 (m, 1H×4/5), 5.85-5.78 (m, 1H×1/5), 5.36-5.26 (m, 1H×1/5), 5.16-5.11 (m, 1H×4/5), 4.34-4.33 (m, 1H), 3.10-3.04 (m, 3H), 2.74-2.71 (m, 1H), 2.44-2.17 (m, 2H), 2.26 (s, 1H×3/5), 2.17 (s, 2H+1H×2/5), 1.90-1.68 (m, 4H), 1.64 (d, J=6.8 Hz, 3H), 1.37 (t, J=7.8 Hz, 3H)

mass: 482 (M+1)$^+$

Examples 56 and 57

Synthesis of 4-(8-chloroimidazo[1,2-a]pyridin-3-yl)-2-{[(1S)-1-(4-{hydroxy[(2R)-1-methylpyrrolidin-2-yl]methyl}phenyl)ethyl]amino}pyrimidine-5-carbonitriles [56] (hereinafter, referred to as the compound [56]) and [57] (hereinafter, referred to as the compound [57]) (here, the compound [56] and the compound [57] are diastereomers. Please see Tables 10 and 11)

12 mg of the title compound [56] and 12 mg of the title compound [57] were obtained both as a colorless solid from 73 mg of the compound [54-1] and 66 mg of the compound [9-1] according to the method of Example 1-(7). According to the purification conditions mentioned in Example 1-(7), the compound [56] was a low polarity compound and the compound [57] was a high polarity compound.

The spectral data of the compound [56] and compound [57] are presented below.

Compound [56]

$^1$H-NMR (CDCl$_3$) δ: 9.71 (d, J=6.8 Hz, 1H×1/5), 8.97 (s, 1H×1/5), 8.92 (s, 1H×4/5), 8.87 (d, J=6.8 Hz, 1H×4/5), 8.61 (s, 1H×1/5), 8.56 (s, 1H×4/5), 7.56-6.96 (m, 5H), 6.66-6.62 (m, 1H), 6.13-6.12 (m, 1H×4/5), 5.91-5.82 (m, 1H×1/5), 5.34-5.32 (m, 1H×1/5), 5.15-5.08 (m, 1H×4/5), 4.86-4.85 (m, 1H), 3.68-3.50 (m, 1H), 3.18-3.05 (m, 1H), 2.45 (s, 3H), 2.53-2.27 (m, 2H), 1.64-1.53 (m, 4H), 1.64 (d, J=7.2 Hz, 3H)

mass: 488, 490 (M+1)$^+$.

Compound [57]

$^1$H-NMR (CDCl$_3$) δ: 9.71 (d, J=6.8 Hz, 1H×1/5), 8.97 (s, 1H×1/5), 8.89 (s, 1H×4/5), 8.71 (d, J=6.8 Hz, 1H×4/5), 8.60 (s, 1H×1/5), 8.56 (s, 1H×4/5), 7.52-6.97 (m, 5H), 6.66-6.63 (m, 1H), 6.11-6.09 (m, 1H×4/5), 5.92-5.80 (m, 1H×1/5), 5.38-5.25 (m, 1H×1/5), 5.12-5.06 (m, 1H×4/5), 4.32-4.31 (m, 1H), 4.22 (brs, 1H), 3.10-3.07 (m, 1H), 2.73-2.69 (m, 1H), 2.41-2.35 (m, 1H), 2.25 (s, 1H×3/5), 2.18 (s, 2H+1H×2/5), 1.93-1.60 (m, 4H), 1.61 (d, J=7.2 Hz, 3H)

mass: 488, 490 (M+1)$^+$.

Examples 58 and 59

Synthesis of 4-[8-(difluoromethyl)imidazo[1,2-a]pyridin-3-yl]-2-{[(1S)-1-(4-{hydroxy[(2R)-1-methylpyrrolidin-2-yl]methyl}phenyl)ethyl]amino}pyrimidine-5-carbonitriles [58] (hereinafter, referred to as the compound [58]) and [59] (hereinafter, referred to as the compound [59]) (here, the compound [58] and the compound [59] are diastereomers. Please see Table 11)

11 mg of the title compound [58] and 12 mg of the title compound [59] were obtained both as a colorless solid from 73 mg of the compound [54-1] and 66 mg of the compound [10-2] according to the method of Example 1-(7). According to the purification conditions mentioned in Example 1-(7), the compound [58] was a low polarity compound and the compound [59] was a high polarity compound.

The spectral data of the compound [58] and compound [59] are presented below.

Compound [58]

$^1$H-NMR (CDCl$_3$) δ: 9.86 (d, J=6.8 Hz, 1H×1/5), 9.01 (d, J=6.8 Hz, 1H×4/5), 9.00 (s, 1H×1/5), 8.93 (s, 1H×4/5), 8.61 (s, 1H×1/5), 8.56 (s, 1H×4/5), 7.75-7.12 (m, 6H), 6.80-6.77 (m, 1H), 6.11-6.10 (m, 1H×4/5), 5.90-5.82 (m, 1H×1/5), 5.34-5.33 (m, 1H×1/5), 5.15-5.08 (m, 1H×4/5), 4.87-4.86 (m, 1H), 3.14-3.10 (m, 1H), 2.45 (s, 3H), 2.48-2.27 (m, 3H), 1.65-1.53 (m, 4H), 1.64 (d, J=7.2 Hz, 3H)

mass: 504 (M+1)$^+$.

Compound [59]

$^1$H-NMR (CDCl$_3$) δ: 9.87 (d, J=6.8 Hz, 1H×1/5), 8.99 (s, 1H×1/5), 8.90 (s, 1H×4/5), 8.85 (d, J=6.8 Hz, 1H×4/5), 8.60 (s, 1H×1/5), 8.57 (s, 1H×4/5), 7.74-7.10 (m, 6H), 6.82-6.78 (m, 1H), 6.13-6.05 (m, 1H×4/5), 5.90-5.82 (m, 1H×1/5), 5.38-5.30 (m, 1H×1/5), 5.11-5.06 (m, 1H×4/5), 4.33-4.31 (m, 1H), 3.11-3.07 (m, 1H), 2.74-2.69 (m, 1H), 2.45-2.17 (m, 2H), 2.25 (s, 1H×3/5), 2.19 (s, 2H+1H×2/5), 1.90-1.60 (m, 4H), 1.62 (d, J=7.2 Hz, 3H)

mass: 504 (M+1)$^+$.

Example 60

Synthesis of 2-[((1S)-1-{4-[(1S)-2-(tert-butylamino)-1-hydroxyethyl]phenyl}ethyl)amino]-4-[8-(difluoromethyl)imidazo[1,2-a]pyridin-3-yl]pyrimidine-5-carbonitrile [60] (hereinafter, referred to as the compound [60])

29 mg of hydrochloride salt of the title compound [60] was obtained as a white solid from 101 mg of the compound [5-5] and 95 mg of the compound [10-2] according to the method of Example 5-(7).

The spectral data of the compound [60] are presented below.

$^1$H-NMR (DMSO-$d_6$) δ: 10.20 (d, J=6.8 Hz, 1H×1/2), 9.11 (d, J=6.4 Hz, 1H×1/2), 9.06 (d, J=7.2 Hz, 1H×1/2), 8.96 (d, J=8.0 Hz, 1H×1/2), 8.78 (s, 1H×1/2), 8.77 (s, 1H×1/2), 8.74 (s, 1H×1/2), 8.64 (s, 1H×1/2), 7.86 (d, J=8.0 Hz, 1H×1/2), 7.79 (d, J=7.2 Hz, 1H×1/2), 7.51 (t, J=54.4 Hz, 1H×1/2), 7.45 (t, J=54.4 Hz, 1H×1/2), 7.37-7.29 (m, 5H+1H×1/2), 7.13 (t, J=7.2 Hz, 1H×1/2), 5.30-5.04 (m, 2H), 4.51-4.45 (m, 1H), 2.60-2.50 (m, 2H), 1.54-1.48 (m, 3H), 1.00 (s, 9H×1/2), 0.93 (s, 9H×1/2).

mass: 506 (M+1)$^+$.

Example 61

Synthesis of 2-[((1S)-1-{4-[(1S)-2-(tert-butylamino)-1-hydroxyethyl]phenyl}ethyl)amino]-4-(8-chloroimidazo[1,2-a]pyridin-3-yl)pyrimidine-5-carbonitrile [61] (hereinafter, referred to as the compound [61])

1.2 g of hydrochloride salt of the title compound [61] was obtained as a white solid from 2.23 g of the compound [5-5] and 2 g of the compound [9-1] according to the method of Example 5-(7).

The spectral data of the compound [61] are presented below.

$^1$H-NMR (DMSO-$d_6$) δ: 10.06 (dd, J=6.8 Hz, 0.8 Hz, 1H×1/2), 9.06 (d, J=6.8 Hz, 1H×1/2), 8.99 (dd, J=7.2 Hz, 1.2 Hz, 1H×1/2), 8.97 (d, J=8.4 Hz, 1H×1/2), 8.78 (s, 1H×1/2), 8.75 (d, J=5.2 Hz, 1H×1/2), 8.62 (s, 1H×1/2), 7.79 (dd, J=7.6 Hz, 1.2 Hz, 1H×1/2), 7.72 (dd, J=7.6 Hz, 0.8 Hz, 1H×1/2), 7.37-7.28 (m, 5H+1H×1/2), 7.19 (t, J=7.2 Hz, 1H×1/2), 7.00 (t, J=7.2 Hz, 1H×1/2), 5.28-5.05 (m, 2H), 4.49-4.44 (m, 1H), 2.57-2.51 (m, 2H), 1.54-1.48 (m, 3H), 1.00 (s, 9H×1/2), 0.93 (s, 9H×1/2).

mass: 490, 492 (M+1)$^+$.

Example 62

Synthesis of 2-[((1S)-1-{4-[(1S)-2-(tert-butylamino)-1-hydroxyethyl]phenyl}ethyl)amino]-4-(8-cyclopropylimidazo[1,2-a]pyridin-3-yl)pyrimidine-5-carbonitrile [62] (hereinafter, referred to as the compound [62])

48 mg of hydrochloride salt of the title compound [62] was obtained as a yellow solid from 102 mg of the compound [5-5] and 93 mg of the compound [36-1] according to the method of Example 5-(7).

The spectral data of the compound [61] are presented below.

$^1$H-NMR (DMSO-$d_6$) δ: 9.93 (dd, J=6.8 Hz, 1.2 Hz, 1H×1/2), 9.06 (dd, J=7.2 Hz, 1.2 Hz, 1H×1/2), 9.03 (d, J=7.2 Hz, 1H×1/2), 8.97 (d, J=8.0 Hz, 1H×1/2), 8.97-8.88 (m, 1H), 8.75 (s, 1H×1/2), 8.74 (s, 1H×1/2), 8.69 (s, 1H×1/2), 8.64 (s, 1H×1/2), 8.50-8.35 (m, 1H), 7.45-7.36 (m, 4H), 7.17-7.08 (m, 3H×1/2), 7.01 (t, J=7.2 Hz, 1H×1/2), 6.20-6.00 (m, 1H), 5.26-5.10 (m, 1H), 4.90-4.80 (m, 1H), 3.05-2.79 (m, 2H), 2.62-2.51 (m, 1H), 1.52 (d, J=7.2 Hz, 3H×1/2), 1.50 (d, J=7.2 Hz, 3H×1/2), 1.28 (s, 9H×1/2), 1.25 (s, 9H×1/2), 1.11-0.95 (m, 4H).

mass: 496 (M+1)$^+$.

Examples 63 and 64

Synthesis of 4-(8-cyclopropylimidazo[1,2-a]pyridin-3-yl)-2-[((1S)-1-{4-[[(2S)-1,2-dimethylpyrrolidin-2-yl](hydroxy)methyl]phenyl}ethyl)amino]pyrimidine-5-carbonitrile [63] (hereinafter, referred to as the compound [63]) and [64] (hereinafter, referred to as the compound [64]) (here, the compound [63] and the compound [64] are diastereomers. Please see Table 12)

(1) To the solution prepared by dissolving 500 mg of H-α-Me-Pro-OH (commercially available from Chem-Impex International Inc.) and 693 mg of benzyl chloroformate in 10 mL of 1,4-dioxane and 5 mL of water, a 1 M aqueous sodium hydroxide solution was added at room temperature so as to keep pH 10, and the solution was stirred at room temperature for 30 minutes. To the reaction solution, 5 M HCl was added so as to adjust the pH to 2, and the mixture was extracted with ethyl acetate. The obtained organic layer was washed with saturated brine, and dried over anhydrous magnesium sulfate. The insolubles were filtered, and the filtrate was concentrated under reduced pressure to obtain 842 mg of 1-[(benzyloxy)carbonyl]-2-methyl-L-proline [63-1] (hereinafter, referred to as the compound [63-1]).

(2) To a solution obtained by dissolving 840 mg of the compound [63-1] in 16 mL of tetrahydrofuran, 4.31 mL of a borane-methyl sulfide complex (a 2 M tetrahydrofuran solution) was added at room temperature, and the mixture was heated under reflux for 4 hours. To the reaction solution, a saturated aqueous sodium hydrogen carbonate solution was added, and the mixture was extracted with ethyl acetate. The obtained organic layer was washed with saturated brine, and dried over anhydrous magnesium sulfate. The insolubles were filtered, and the filtrate was concentrated under reduced pressure. The obtained residue was purified by silica gel column chromatography (eluent: hexane/ethyl acetate=100/0 to 60/40) to obtain 498 mg of benzyl (2S)-2-(hydroxymethyl)-2-methylpyrrolidine-1-carboxylate [63-2] (hereinafter, referred to as the compound [63-2]).

(3) To a solution obtained by dissolving 377 mg of the compound [63-2] and 147 mg of pyridine in 7.5 mL of chloroform, 673 mg of Dess-Martin periodinane was added at room temperature, and the mixture was heated under reflux for 1 hour. To the reaction solution, a saturated aqueous sodium thiosulfate solution was added, and the mixture was extracted with chloroform. The obtained organic layer was washed with a saturated aqueous sodium hydrogen carbonate solution and saturated brine, sequentially, and dried over anhydrous sodium sulfate. The insolubles were filtered, and the filtrate was concentrated under reduced pressure. The obtained residue was purified by silica gel column chromatography (eluent: hexane/ethyl acetate 100/0 to 60/40) to obtain 346 mg of benzyl (2S)-2-formyl-2-methylpyrrolidine-1-carboxylate [63-3] (hereinafter, referred to as the compound [63-3].

(4) 423 mg of the compound [1-1] and 508 mg of N,N,N',N'-tetramethylethylene diamine were dissolved in 22 mL of tetrahydrofuran, the temperature of the solution was kept at −78° C., and then 1.09 mL of n-butyl lithium (2.66 M hexane solution) was added thereto. After stirring at the same temperature for 1 hour to obtain the resultant white suspension, 2.2 mL of a tetrahydrofuran solution prepared by dissolving 384 mg of the compound [63-3] was added thereto, and the mixture was stirred at the same temperature for 1.5 hours. To the reaction mixture, a saturated aqueous ammonium chloride solution was added, and the mixture was extracted with ethyl acetate. The obtained organic layer was washed with saturated brine, and dried over anhydrous sodium sulfate. Thereafter, the insolubles were filtered, and the filtrate was concentrated under reduced pressure to obtain benzyl (2S)-2-[(4-{(1S)-1-[(tert-butoxycarbonyl)amino]ethyl}phenyl)(hydroxy)methyl]-2-methylpyrrolidine-1-carboxylate [634]. The compound [634] obtained was a mixture of two isomers, which was then purified by silica gel column chromatography (eluent: hexane/ethyl acetate=100/0 to 40/60) to obtain 199 mg of a low polarity compound (compound that eluted first under the above condition) [634a] (hereinafter, referred to as the compound [634a]) and 117 mg of a high polarity compound (compound that eluted afterwards under the above condition) [634b] (hereinafter, referred to as the compound [63-4b]). Here, the compound [634a] is a precursor of a compound [63], and the compound [634b] is a precursor of a compound [64] described later.

(5) 23.3 mg of the compound [63] was obtained as a white solid from 38 mg of the compound [36-1] and 57.5 mg of the compound [63-4a] according to the methods of EXAMPLES 50, and 51-(2) to (4).

The spectral data of the compound [63] are shown below.

$^1$H-NMR (CDCl$_3$) δ: 9.70-9.62 (m, 1H1/5), 8.98 (d, J=6.8 Hz, 1H 4/5), 8.92 (s, 1H 1/5), 8.88 (s, 1H 4/5), 8.57 (s, 1H1/5), 8.52 (s, 1H 4/5), 7.36-7.28 (m, 4H), 6.96-6.88 (m, 1H+1H1/5), 6.71-6.68 (m, 1H 4/5), 5.38-5.27 (m, 1H1/5), 5.15-5.13 (m, 1H 4/5), 4.39 (s, 1H), 3.10-3.07 (m, 1H), 2.59-2.45 (m, 2H), 2.19-2.03 (m, 2H), 2.10 (s, 3H), 1.73-1.51 (m, 2H), 1.62 (d, J=6.8 Hz, 3H), 1.31-1.26 (m, 1H), 1.17-1.15 (m, 2H), 0.92-0.86 (m, 5H)

mass: 508 (M+1)$^+$.

(6) 10.6 mg of the title compound [64] was obtained as a white solid from 38 mg of the compound [36-1] and 57.5 mg of the compound [63-4b] according to the methods of EXAMPLES 50, and 51-(2) to (4).

The spectral data of the compound [64] are shown below.

$^1$H-NMR (CDCl$_3$) δ: 9.63-9.56 (m, 1H1/5), 8.97 (s, 1H1/5), 8.90 (s, 1H 4/5), 8.74 (d, J=6.8 Hz, 1H 4/5), 8.58 (s, 1H1/5), 8.53 (s, 1H 4/5), 7.44-7.28 (m, 4H), 6.93-6.85 (m, 1H+1H 1/5), 6.68-6.64 (m, 1H 4/5), 6.04-6.02 (m, 1H 4/5), 5.85-5.80 (m, 1H1/5), 5.40-5.28 (m, 1H1/5), 5.14-5.11 (m, 1H 4/5), 4.43 (s, 1H), 3.15-3.10 (m, 1H), 2.62-2.49 (m, 2H), 2.28 (s, 3H), 2.13-2.05 (m, 1H), 1.78-1.50 (m, 2H), 1.62 (d, J=6.8 Hz, 3H), 1.38-1.25 (m, 1H), 1.15-1.12 (m, 2H), 0.94-0.85 (m, 5H)

mass: 508 (M+1)$^+$.

Examples 65 and 66

Synthesis of 4-(8-cyclopropylimidazo[1,2-a]pyridin-3-yl)-2-[((1S)-1-{4-[(R)-[(2R)-1,2-dimethylpyrrolidin-2-yl](hydroxy)methyl]phenyl}ethyl)amino]pyrimidine-5-carbonitrile [65] (hereinafter, referred to as the compound [65]) and 4-(8-cyclopropylimidazo[1,2-a]pyridin-3-yl)-2-[((1S)-1-{4-[(S)-[(2R)-1,2-dimethylpyrrolidin-2-yl](hydroxy)methyl]phenyl}ethyl)amino]pyrimidine-5-carbonitrile [66] (hereinafter, referred to as the compound [66]) (here, the compound [65] and the compound [66] are diastereomers. Please see Table 12)

(1) Benzyl (2R)-2-[(4-{(1S)-1-[(tert-butoxycarbonyl)amino]ethyl}phenyl)(hydroxy)methyl]-2-methylpyrrolidine-1-carboxylate [65-1] was obtained from 1 g of H-α-Me-D-Pro-OH (commercially available from Chem-Impex International Inc.) according to the methods of EXAMPLES 63 and 64-(1) to (4). The compound [65-1] obtained was a mixture of two isomers, and 195 mg of [65-1a] (hereinafter, referred to as the compound [65-1a]) and 134 mg of [65-1b] (hereinafter, referred to as the compound [65-1b]) were obtained under the purification condition described in EXAMPLES 63 and 64-(4). In EXAMPLES, the low polarity compound (compound that eluted first under the above condition) is a compound [65-1a], and the high-polarity compound (compound that eluted afterwards under the above condition) is a compound [65-1b].

(2) 140 mg of tert-butyl ((1S)-1-{4-[(R)-[(2R)-1,2-dimethylpyrrolidin-2-yl](hydroxy)methyl]phenyl}ethyl)carbamate [65-2] (hereinafter, referred to as the compound [65-2]) was obtained from 193 mg of the compound [65-1a] according to the methods of EXAMPLES 54 and 55-(1).

(3) 21.4 mg of the title compound [65] (hereinafter, referred to as the compound [65]) was obtained as a pale yellow solid from 45.6 mg of the compound [36-1] and 49 mg of the compound [65-2] according to the method of EXAMPLE 1-(7).

The spectral data of the compound [65] are shown below.

$^1$H-NMR (CDCl$_3$) δ: 9.63-9.55 (m, 1H1/5), 8.97 (s, 1H1/5), 8.89 (s, 1H 4/5), 8.73 (d, J=6.8 Hz, 1H 4/5), 8.58 (s, 1H1/5), 8.53 (s, 1H 4/5), 7.37-7.29 (m, 4H), 6.93-6.84 (m, 1H+1H1/5), 6.68-6.65 (m, 1H 4/5), 6.02-6.00 (m, 1H 4/5), 5.84-5.77 (m, 1H1/5), 5.38-5.26 (m, 1H1/5), 5.13-5.09 (m, 1H 4/5), 4.67-4.50 (m, 1H), 4.34 (s, 1H), 3.11-3.07 (m, 1H), 2.62-2.45 (m, 2H), 2.17-2.11 (m, 2H), 2.04 (s, 3H), 1.74-1.61 (m, 2H), 1.62 (d, J=6.8 Hz, 3H), 1.32-1.20 (m, 2H), 1.15-1.12 (m, 1H), 0.90-0.85 (m, 5H)

mass: 508 (M+1)$^+$.

(4) The absolute configuration of the title compound [65] was determined by the following method. To 9.2 mg of the compound [65-1a], 1 mL of a 2 M aqueous potassium hydroxide solution was added at room temperature, and the mixture was stirred at the same temperature for 2 hours. The reaction solution was concentrated under reduced pressure. To the obtained residue, water was added, and the mixture was extracted with chloroform. The obtained organic layer was washed with saturated brine, and dried over anhydrous sodium sulfate. The insolubles were filtered, and the filtrate was concentrated under reduced pressure. The obtained residue was purified by preparative thin-layer chromatography to obtain 6.1 mg of tert-butyl ((1S)-1-{4-[(1R,7aR)-7a-methyl-3-oxotetrahydro-1H-pyrrolo[1,2-c][1,3]oxazol-1-yl]phenyl}ethyl)carbamate [65-4] (hereinafter, referred to as the compound [65-4]). By NOE (Nucleus Overhauser Effect)

measurement of the compound [65-4], the absolute configurations of the compound [65-4] and the title compound [65] were determined.

(5) 15.7 mg of the title compound [66] (hereinafter, referred to as the compound [66]) was obtained as a pale yellow solid from 45.6 mg of the compound [36-1] and 132 mg of the compound [65-1b] according to the methods of EXAMPLES 65 and 66-(2) and (3).

The spectral data of the compound [66] are shown below.
$^1$H-NMR (CDCl$_3$) δ: 9.63-9.55 (m, 1H1/5), 8.97-8.90 (m, 1H+1H 4/5), 8.58 (s, 1H1/5), 8.53 (s, 1H 4/5), 7.43-7.32 (m, 4H), 6.93-6.85 (m, 1H+1H 1/5), 6.66-6.62 (m, 1H 4/5), 6.04-6.03 (m, 1H 4/5), 5.85-5.78 (m, 1H1/5), 5.38-5.28 (m, 1H1/5), 5.16-5.13 (m, 1H 4/5), 4.80-4.67 (m, 1H), 4.43 (s, 1H), 3.15-3.07 (m, 1H), 2.63-2.49 (m, 2H), 2.27 (s, 3H), 2.09-2.05 (m, 1H), 1.85-1.50 (m, 2H), 1.62 (d, J=6.8 Hz, 3H), 1.36-1.26 (m, 2H), 1.16-1.14 (m, 1H), 0.90-0.80 (m, 5H)

mass: 508 (M+1)$^+$.

(6) The absolute configuration of the title compound [66] was determined by the following method. 11.6 mg of tert-butyl ((1S)-1-{4-[(1S,7aR)-7a-methyl-3-oxotetrahydro-1H-pyrrolo[1,2-c][1,3]oxazol-1-yl]phenyl}ethyl)carbamate [65-6] (hereinafter, referred to as the compound [65-6]) was obtained from 30 mg of the compound [65-1b] according to the methods of EXAMPLES 65 and 66-(4). By NOE (Nucleus Overhauser Effect) measurement of the compound [65-6], the absolute configurations of the compound [65-6] and the title compound [66] were determined.

Example 67

Synthesis of (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol [67]
(hereinafter, referred to as the compound [67])

(1) A mixture of 18.9 g of 2,4-dichloro-5-fluoropyrimidine (commercially available from Fluorochem Co. Ltd), 42.9 g of cis-1-ethoxy-2-tri-n-butylstanylethylene (synthesized by the method as described in J. Am. Chem. Soc., 1977, 99, 7365), 3.97 g of dichlorobis(triphenylphosphine) palladium (II), and 380 mL of acetonitrile was stirred at 80° C. for 3 hours. After cooling the reaction mixture, 113 mL of water and 53 g of potassium fluoride were added thereto, and the mixture was stirred overnight at room temperature. The insolubles were filtered through Celite, and the filtrate was extracted with ethyl acetate. The obtained organic layer was washed with water and saturated brine, sequentially, and dried over anhydrous sodium sulfate. The insolubles were filtered, and the filtrate was concentrated under reduced pressure. Then, the obtained residue was purified by silica gel column chromatography (eluent: hexane/ethyl acetate=100/0 to 40/60) to obtain 14.0 g of 2-chloro-4-[(Z)-2-ethoxyvinyl]-5-fluoropyrimidine [67-1] (hereinafter, referred to as the compound [67-1]) as a yellow solid.

(2) 25.2 g of the compound [67-1] was dissolved in a mixed solvent of 320 mL of 1,4-dioxane and 32 mL of water. Then, 22.2 g of N-bromosuccinic acid imide was added under an ice-cold condition, and the mixture was stirred at room temperature for 2 hours. To the reaction solution, 16.0 g of 2-amino-3-chloropyridine was added, and the mixture was stirred overnight at room temperature. A saturated aqueous sodium hydrogen carbonate solution was added thereto, and the mixture was extracted with a mixed solvent of chloroform and methanol (mixing ratio: 9/1). The obtained organic layer was dried over anhydrous sodium sulfate. The insolubles were filtered, and the filtrate was concentrated under reduced pressure. To the obtained residue, hexane was added, and the mixture was stirred for 30 minutes. The solid was taken by filtration, and dried under reduced pressure to obtain 20.0 g of 8-chloro-3-(2-chloro-5-fluoropyrimidin-4-yl)imidazo[1,2-a]pyridine [67-2] (hereinafter, referred to as the compound [67-2]) as a yellow solid.

(3) 15.8 g of the compound [5-5] was dissolved in 50 mL of chloroform, 45 mL of trifluoroacetic acid was added thereto under an ice-cold condition, and the mixture was stirred at room temperature for 1 hour. The reaction solution was concentrated under reduced pressure, and the obtained residue was purified by silica gel column chromatography (eluent: chloroform/methanol=100/0 to 90/10) to obtain 10.7 g of (1S)-1-{4-[(1S)-1-aminoethyl]phenyl}-2-(tert-butylamino) ethanol [67-3] (hereinafter, referred to as the compound [67-3]) as a white solid.

(4) A mixture of 3.00 g of the compound [67-2], 3.01 g of the compound [67-3], 1.12 g of sodium carbonate, and 10 mL of N-methyl-2-pyrrolidinone was stirred at 170° C. for 2 hours. To the reaction solution, water was added, and the mixture was extracted with a mixed solvent of chloroform and ethyl acetate (mixing ratio: 1/10). The obtained organic layer was washed with water, and then dried over anhydrous sodium sulfate. The insolubles were filtered, and the filtrate was concentrated under reduced pressure. The obtained residue was purified by silica gel column chromatography (eluent: chloroform/methanol=100/0 to 98/2). The obtained solution was concentrated under reduced pressure, and the residue was dissolved in ethyl acetate and solidified to obtain 3.79 g of the title compound [67] as a pale yellow solid.

The spectral data of the compound [67] are shown below.
$^1$H-NMR (CDCl$_3$) δ: 9.22 (brs, 1H), 8.41 (d, J=3.9 Hz, 1H), 8.24 (d, J=3.9 Hz, 1H), 7.42-7.37 (m, 5H), 6.68 (brs, 1H), 5.50 (d, J=5.9 Hz, 1H), 5.03 (quint, J=6.8 Hz, 1H), 4.57 (dd, J=9.0 Hz, 3.7 Hz, 1H), 2.87 (dd, 12.0 Hz, 3.7 Hz, 1H), 2.53 (dd, J=12.0 Hz, 9.0 Hz, 1H), 1.60 (d, J=6.8 Hz, 3H), 1.07 (s, 9H)

mass: 483 (M+1)$^+$.

Example 68

Synthesis of (1S)-1-[4-((1S)-1-{[4-(8-chloroimidazo[1,2-a]pyridin-3-yl)-5-fluoropyrimidin-2-yl]amino}ethyl)phenyl]-2-[(1,1-dimethylpropyl)amino]ethanol [68] (hereinafter, referred to as the compound [68])

(1) 509 mg of tert-butyl [(1S)-1-(4-{(1S)-2-[(1,1-dimethylpropyl)amino]-1-hydroxyethyl}phenyl)ethyl]carbamate [68-1] (hereinafter, referred to as the compound [68-1]) was obtained from 500 mg of the compound [5-4] and 1.66 g of tert-amylamine according to the method of EXAMPLE 7-(3).

(2) 34 mg of the title compound [68] (hereinafter, referred to as the compound [68]) was obtained as a pale brown solid from 43.5 mg of the compound [67-2] and 70 mg of the compound [68-1] according to the methods of EXAMPLE 67-(3) and (4).

The spectral data of the compound [68] are shown below.
$^1$H-NMR (CDCl$_3$) δ: 9.23 (br, 1H), 8.42 (d, J=3.9 Hz, 1H), 8.25 (d, J=3.7 Hz, 1H), 7.42-7.40 (m, 5H), 7.26 (s, 1H), 6.69 (br, 1H), 5.49 (d, J=6.3 Hz, 1H), 5.03 (quint, J=6.3 Hz, 1H), 4.57 (dd, J=9.0 Hz, 3.7 Hz, 1H), 2.83 (dd, J=11.7 Hz, 3.7 Hz, 1H), 2.49 (dd, J=11.7 Hz, 9.0 Hz, 1H), 1.60 (d, J=6.8 Hz, 3H), 1.36 (q, J=7.6 Hz, 2H), 1.05-1.00 (m, 1H), 1.00 (s, 6H), 0.81 (t, J=7.6 Hz, 3H)

mass: 497, 499 (M+1)$^+$.

Example 69

Synthesis of (1S)-1-[4-((1S)-1-{[4-(8-chloroimidazo[1,2-a]pyridin-3-yl)-5-fluoropyrimidin-2-yl]amino}ethyl)phenyl]-2-(cyclopentylamino)ethanol [69] (hereinafter, referred to as the compound [69])

(1) 451 mg of tert-butyl ((1S)-1-{4-[(1S)-2-(cyclopentylamino)-1-hydroxyethyl]phenyl}ethyl)carbamate [69-1] (hereinafter, referred to as the compound [69-1]) was obtained from 440 mg of the compound [5-4] and 3.0 g of cyclopentylamine according to the method of EXAMPLE 7-(3).

(2) 4.6 mg of the title compound [69] (hereinafter, referred to as the compound [69]) was obtained as a pale yellow solid from 30 mg of the compound [67-2] and 35.6 mg of the compound [69-1] according to the methods of EXAMPLE 67-(3) and (4).

The spectral data of the compound [69] are shown below.
$^1$H-NMR (CDCl$_3$) δ: 9.20 (brs, 1H), 8.41 (d, J=3.9 Hz, 1H), 8.24 (d, J=3.4 Hz, 1H), 7.40 (m, 5H), 6.67 (m, 1H), 5.51 (m, 1H), 5.03 (m, 1H), 4.69 (dd, J=9.0 Hz, 3.2 Hz, 1H), 3.09 (quint, 6.6 Hz, 1H), 2.89 (dd, J=12.0 Hz, 3.7 Hz, 1H), 2.63 (dd, J=12.0 Hz, 9.0 Hz, 1H), 1.80-1.65 (m, 4H), 1.59 (d, J=6.8 Hz, 3H), 1.55-1.20 (m, 4H)
mass: 495 (M+1)$^+$.

Example 70

Synthesis of (1S)-1-[4-((1S)-1-{[4-(8-chloroimidazo[1,2-a]pyridin-3-yl)-5-fluoropyrimidin-2-yl]amino}ethyl)phenyl]-2-(isopropylamino)ethanol [70] (hereinafter, referred to as the compound [70])

(1) 2.94 g of tert-butyl ((1S)-1-{4-[(1S)-1-hydroxy-2-(isopropylamino)ethyl]phenyl}ethyl)carbamate [70-1] (hereinafter, referred to as the compound [70-1]) was obtained from 2.4 g of the compound [5-4] and 12.4 g of isopropylamine according to the method of EXAMPLE 7-(3).

(2) 34 mg of the title compound [70] (hereinafter, referred to as the compound [70]) was obtained as a yellow solid from 20 mg of the compound [67-2] and 29.7 mg of the compound [70-1] according to the methods of EXAMPLE 67-(3) and (4).

The spectral data of the compound [70] are shown below.
$^1$H-NMR (CDCl$_3$) δ: 9.20 (brs, 1H), 8.40 (d, J=3.9 Hz, 1H), 8.23 (d, J=3.4 Hz, 1H), 7.40 (m, 5H), 6.67 (m, 1H), 5.52 (m, 1H), 5.03 (m, 1H), 4.67 (dd, J=9.3 Hz, 3.4 Hz, 1H), 2.91 (dd, 12.2 Hz, 3.4 Hz, 1H), 2.81 (quint, J=6.1 Hz, 1H), 2.61 (dd, J=12.0 Hz, 9.0 Hz, 1H), 1.59 (d, J=6.8 Hz, 3H), 1.05 (dd, J=6.3 Hz, 3.4 Hz, 6H)
mass: 469 (M+1)$^+$.

Example 71

Synthesis of (1S)-1-[4-((1S)-1-{[4-(8-chloroimidazo[1,2-a]pyridin-3-yl)-5-fluoropyrimidin-2-yl]amino}ethyl)phenyl]-2-[(1-methylcyclopentyl)amino]ethanol [71] (hereinafter, referred to as the compound [71])

(1) A mixture of 500 mg of the compound [54], 639 mg of 1-methylcyclopentylamine monohydrochloride (synthesized by the method as described in J. Med. Chem., 2006, 49, 3068), 613 mg of N,N-diisopropyl ethylamine, 5 mL of ethanol, and 5 mL of water was heated overnight under reflux. The reaction solution was concentrated. To the obtained residue, water was added, and the mixture was extracted with ethyl acetate. The obtained organic layer was dried over anhydrous magnesium sulfate. The insolubles were filtered, and the filtrate was concentrated under reduced pressure. The obtained residue was purified by silica gel column chromatography (eluent: chloroform/methanol=100/0 to 95/5) to obtain 365 mg of tert-butyl [(1S)-1-(4-{(1S)-1-hydroxy-2-[(1-methylcyclopentyl)amino]ethyl}phenyl)ethyl]carbamate [71-1] (hereinafter, referred to as the compound [71-1]) as a white solid.

(2) 25.9 mg of the title compound [71] (hereinafter, referred to as the compound [71]) was obtained as a pale yellow solid from 45 mg of the compound [67-2] and 150 mg of the compound [71-1] according to the methods of EXAMPLE 67-(3) and (4).

The spectral data of the compound [71] are shown below.
$^1$H-NMR (CDCl$_3$) δ: 9.21 (br, 1H), 8.41 (d, J=3.9 Hz, 1H), 8.23 (d, J=3.4 Hz, 1H), 7.42-7.37 (m, 5H), 7.26 (s, 1H), 6.68 (brs, 1H), 5.54 (brs, 1H), 5.07-4.99 (m, 1H), 4.58 (dd, J=3.9 Hz, 9.3 Hz, 1H), 2.88 (dd, J=3.9 Hz, 12.2 Hz, 1H), 2.53 (dd, J=9.3 Hz, 12.2 Hz, 1H), 1.65-1.52 (m, 6H), 1.60 (d, J=6.8 Hz, 3H), 1.47-1.39 (m, 2H), 1.30-1.27 (m, 1H), 1.12 (s, 3H)
mass: 509,511 (M+1)$^+$.

Example 72

Synthesis of (1S)-1-[4-((1S)-1-{[4-(8-chloroimidazo[1,2-a]pyridin-3-yl)-5-fluoropyrimidin-2-yl]amino}ethyl)phenyl]-2-{[1-(hydroxymethyl)cyclopentyl]amino}ethanol [72] (hereinafter, referred to as the compound [72])

(1) 483 mg of tert-butyl {(1S)-1-[4-((1S)-1-hydroxy-2-{[1-(hydroxymethyl)cyclopentyl]amino}ethyl)phenyl]ethyl}carbamate [72-1] (hereinafter, referred to as the compound [72-1]) was obtained from 500 mg of the compound [54] and 1.13 g of 1-amino-1-cyclopentanemethanol according to the method of EXAMPLE 7-(3).

(2) 7 mg of the title compound [72] (hereinafter, referred to as the compound [72]) was obtained as a white solid from 55 mg of the compound [67-2] and 150 mg of the compound [72-1] according to the methods of EXAMPLE 67-(3) and (4).

The spectral data of the compound [72] are shown below.
$^1$H-NMR (CDCl$_3$) δ: 9.23 (br, 1H), 8.39-8.37 (m, 1H), 8.23-8.22 (m, 1H), 7.42-7.37 (m, 5H), 7.30 (s, 1H), 6.74-6.68 (m, 1H), 5.03-4.99 (m, 1H), 4.72-4.70 (m, 1H), 3.43-3.36 (m, 2H), 2.80-2.70 (m, 1H), 2.64-2.59 (m, 2H), 1.66-1.52 (m, 13H)
mass: 525, 527 (M+1)$^+$.

Example 73

Synthesis of (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol [73] (hereinafter, referred to as the compound [73])

(1) 23.1 mg of 3-(2-chloro-5-methylpyrimidin-4-yl)-8-cyclopropylimidazo[1,2-a]pyridine [73-1] (hereinafter, referred to as the compound [73-1]) was obtained from 139 mg of 2,4-dichloro-5-methylpyrimidine (commercially available from Aldrich Corporation) and 50.2 mg of 3-cyclopropylpyridine-2-amine (synthesized by the method as described on p. 142 of International Publication of WO 2006/025567) according to the methods of EXAMPLE 67-(1) and (2).

(2) 10.9 mg of the title compound [73] (hereinafter, referred to as the compound [73]) was obtained as a white solid from 53 mg of the compound [67-3] and 21.3 mg of the compound [73-1] according to the method of EXAMPLE 67-(4).

The spectral data of the compound [73] are shown below.
$^1$H-NMR (CDCl$_3$) δ: 8.77 (brs, 1H), 8.21 (s, 1H), 8.06 (s, 1H), 7.38 (s, 4H), 6.77 (d, J=6.8 Hz, 11H), 6.54 (brs, 11H), 5.38 (d, J=5.9 Hz, 11H), 5.11 (quint, J=7.0 Hz, 11H), 4.60 (dd, J=9.0 Hz, 3.7 Hz, 1H), 2.89 (dd, J=11.7 Hz, 3.4 Hz, 1H), 2.64-2.56 (m, 2H), 2.35 (s, 3H), 1.56 (d, J=6.8 Hz, 3H), 1.15-1.10 (m, 2H), 1.08 (s, 9H), 0.92-0.82 (m, 2H)
mass: 485 (M+1)$^+$.

Example 74

Synthesis of (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol [74] (hereinafter, referred to as the compound [74])

(1) 65.1 mg of 8-chloro-3-(2-chloro-5-methylpyrimidin-4-yl)imidazo[1,2-a]pyridine [74-1] (hereinafter, referred to as the compound [74-1]) was obtained from 139 mg of 2,4-dichloro-5-methylpyrimidine and 110 mg of 3-chloropyridine-2-amine according to the methods of EXAMPLE 67-(1) and (2).

(2) 11.1 mg of the title compound [74] (hereinafter, referred to as the compound [74]) was obtained as a white solid from 55.4 mg of the compound [67-3] and 21.8 mg of the compound [74-1] according to the method of EXAMPLE 67-(4).

The spectral data of the compound [74] are shown below.
$^1$H-NMR (CDCl$_3$) δ: 8.71 (brs, 1H), 8.23 (s, 1H), 8.06 (s, 1H), 7.39 (m, 4H), 7.31 (d, J=7.0 Hz, 1H), 6.52 (brs, 1H), 5.47 (d, J=7.0 Hz, 1H), 5.07 (quint, J=6.7 Hz, 1H), 4.62 (dd, J=8.6 Hz, 3.5 Hz, 1H), 2.90 (dd, J=11.7 Hz, 3.5 Hz, 1H), 2.60 (dd, J=11.2 Hz, J=8.4 Hz, 1H), 2.33 (s, 3H), 1.56 (d, J=7.0 Hz, 3H), 1.10 (s, 9H)
mass: 479 (M+1)$^+$.

Example 75

Synthesis of (1S)-2-(tert-butylamino)-1-[4-((1S)-1-{[4-(8-chloroimidazo[1,2-a]pyridin-3-yl)pyrimidin-2-yl]amino}ethyl)phenyl]ethanol [75] (hereinafter, referred to as the compound [75])

(1) 721 mg of 8-chloro-3-(2-chloropyrimidin-4-yl)imidazo[1,2-a]pyridine [75-1] (hereinafter, referred to as the compound [75-1]) was obtained from 565 mg of 2,4-dichloropyrimidine and 488 mg of 3-chloropyridine-2-amine according to the methods of EXAMPLE 67-(1) and (2).

(2) 6.6 mg of the title compound [75] (hereinafter, referred to as the compound [75]) was obtained as a white solid from 33 mg of the compound [67-3] and 48 mg of the compound [75-1] according to the method of EXAMPLE 67-(4).

The spectral data of the compound [75] are shown below.
$^1$H-NMR (CDCl$_3$) δ: 8.29 (d, J=5.4 Hz, 1H), 8.20 (s, 1H), 7.43-7.33 (m, 5H), 7.26 (s, 1H), 6.94 (d, J=5.4 Hz, 1H), 6.68 (br, 1H), 5.57 (brs, 1H), 5.11 (brs, 1H), 4.59 (dd, J=9.3 Hz, 3.4 Hz, 1H), 2.87 (dd, J=3.4 Hz, 11.7 Hz, 1H), 2.55 (dd, J=11.7 Hz, 9.3 Hz, 1H), 1.82-1.72 (m, 2H), 1.61 (d, J=6.8 Hz, 3H), 1.08 (s, 9H)
mass: 465, 467 (M+1)$^+$.

Example 76

Synthesis of (1S)-2-(tert-butylamino)-1-[4-((1S)-1-{[4-(8-cyclopropylimidazo[1,2-a]pyridin-3-yl)pyrimidin-2-yl]amino}ethyl)phenyl]ethanol [76] (hereinafter, referred to as the compound [76])

(1) 775 mg of 3-(2-chloropyrimidin-4-yl)-8-cyclopropylimidazo[1,2-a]pyridine [76-1] (hereinafter, referred to as the compound [76-1]) was obtained from 3 g of 2,4-dichloropyrimidine and 1.19 g of 3-cyclopropylpyridine-2-amine (synthesized by the method as described on p. 142 of the International Publication of WO 2006/025567) according to the methods of EXAMPLE 67-(1) and (2).

(2) 62.9 mg of the title compound [76] (hereinafter, referred to as the compound [76]) was obtained as a pale yellow solid from 66.8 mg of the compound [67-3] and 50 mg of the compound [76-1] according to the method of EXAMPLE 67-(4).

The spectral data of the compound [76] are shown below.
$^1$H-NMR (CDCl$_3$) δ: 9.12 (br, 1H), 8.25 (d, J=5.4 Hz, 1H), 8.18 (s, 1H), 7.43-7.36 (m, 4H), 7.26 (s, 1H), 6.93 (d, J=5.4 Hz, 1H), 6.79-6.78 (m, 1H), 6.66 (brs, 1H), 5.49 (brs, 1H), 5.19-5.10 (m, 1H), 4.58 (dd, J=3.9 Hz, 8.8 Hz, 11H), 2.86 (dd, J=3.9 Hz, 11.7 Hz, 1H), 2.61-2.57 (m, 1H), 2.55 (dd, J=8.8 Hz, 11.7 Hz, 1H), 1.60 (d, J=6.8 Hz, 3H), 1.13-1.11 (m, 2H), 1.07 (s, 9H), 0.88-0.85 (m, 2H)
mass: 471 (M+1)$^+$.

Example 77

Synthesis of (1S)-2-(tert-butylamino)-1-[4-((1S)-1-{[5-chloro-4-(8-cyclopropylimidazo[1,2-a]pyridin-3-yl)pyrimidin-2-yl]amino}ethyl)phenyl]ethanol [77] (hereinafter, referred to as the compound [77])

(1) 831 mg of 8-cyclopropyl-3-(2,5-dichloropyrimidin-4-yl)imidazo[1,2-a]pyridine [77-1] (hereinafter, referred to as the compound [77-1]) was obtained from 1.59 g of 2,4,5-trichloropyrimidine and 1.16 g of 3-cyclopropylpyridine-2-amine (synthesized by the method as described on p. 142 of the International Publication of WO 2006/025567) according to the methods of EXAMPLE 67-(1) and (2).

(2) 49.6 mg of the title compound [77] (hereinafter, referred to as the compound [77]) was obtained as a white solid from 52.5 mg of the compound [67-3] and 67.8 mg of the compound [77-1] according to the method of EXAMPLE 67-(4).

The spectral data of the compound [77] are shown below.
$^1$H-NMR (CDCl$_3$) δ: 8.69 (s, 1H), 8.32 (s, 1H), 7.38 (s, 4H), 7.26 (s, 1H), 6.80 (d, J=7.3 Hz, 1H), 6.58 (br, 1H), 5.40-5.30 (m, 1H), 5.13-5.03 (m, 1H), 4.59 (dd, J=3.9 Hz, 8.8 Hz, 1H), 2.89 (dd, J=3.9 Hz, 12.2 Hz, 1H), 2.65-2.60 (m, 1H), 2.57 (dd, J=8.8 Hz, 12.2 Hz, 1H), 1.61 (br, 2H), 1.58 (d, J=6.8 Hz, 3H), 1.13 (dd, J=2.0 Hz, 8.3 Hz, 2H), 1.08 (s, 9H), 0.89-0.86 (m, 2H)
mass: 505, 507 (M+1)$^+$.

Example 78

Synthesis of (1S)-2-(tert-butylamino)-1-[4-((1S)-1-{[5-chloro-4-(8-chloroimidazo[1,2-a]pyridin-3-yl)pyrimidin-2-yl]amino}ethyl)phenyl]ethanol [78] (hereinafter, referred to as the compound [78])

(1) 1.24 g of 8-chloro-3-(2,5-dichloropyrimidin-4-yl)imidazo[1,2-a]pyridine [78-1] (hereinafter, referred to as the compound [78-1]) was obtained from 1.58 g of 2,4,5-trichloropyrimidine and 1.11 g of 3-chloropyridine-2-amine according to the methods of EXAMPLE 67-(1) and (2).

(2) 62.8 mg of the title compound [78] (hereinafter, referred to as the compound [78]) was obtained as a white solid from 52.5 mg of the compound [67-3] and 66.5 mg of the compound [78-1] according to the method of EXAMPLE 67-(4).

The spectral data of the compound [78] are shown below.
$^1$H-NMR (CDCl$_3$) δ: 8.68 (s, 1H), 8.35 (s, 1H), 7.42-7.34 (m, 5H), 7.26 (s, 1H), 6.56 (br, 1H), 5.56 (brs, 1H), 5.05 (brs, 1H), 4.60 (dd, J=3.4 Hz, 8.8 Hz, 1H), 2.90 (dd, J=3.4 Hz, 11.7 Hz, 1H), 2.57 (dd, J=11.7 Hz, 9.3 Hz, 1H), 1.63 (br, 2H), 1.58 (d, J=7.3 Hz, 3H), 1.09 (s, 9H)
mass: 499, 501 (M+1)$^+$.

Example 79

Synthesis of (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol [79] (hereinafter, referred to as the compound [79])

(1) 13.4 g of 3-(2-chloro-5-fluoropyrimidin-4-yl) -8-cyclopropylimidazo[1,2-a]pyridine [79-1] (hereinafter, referred to as the compound [79-1]) was obtained from 11.5 g of 2,4-dichloro-5-fluoropyrimidine (commercially available from Fluorochem Co. Ltd.) and 9.21 g of 3-cyclopropylpyridine-2-amine (synthesized by the method as described on p. 142 of the International Publication of WO 2006/025567) according to the methods of EXAMPLE 67-(1) and (2).

(2) 673 mg of the title compound [79] (hereinafter, referred to as the compound [79]) was obtained as an orange solid from 1.17 g of the compound [67-3] and 1.1 g of the compound [79-1] according to the method of EXAMPLE 67-(4).

The spectral data of the compound [79] are shown below.
$^1$H-NMR (CDCl$_3$) δ: 9.20 (brs, 1H), 8.41 (d, J=3.9 Hz, 1H), 8.19 (d, J=3.9 Hz, 1H), 7.39 (q, 4H), 6.83 (d, J=6.8 Hz, 1H), 6.69 (m, 1H), 5.44 (d, J=5.9 Hz, 1H), 5.06 (quint, J=7.3 Hz, 1H), 4.57 (dd, J=8.8 Hz, 3.4 Hz, 1H), 2.85 (dd, 12.0 Hz, 3.7 Hz, 1H), 2.62 (dd, J=11.7 Hz, 8.8 Hz, 1H), 1.59 (d, J=6.8 Hz, 3H), 1.13 (d, J=8.8 Hz, 2H), 1.06 (s, 9H), 0.87 (m, 2H)
mass: 489 (M+1)$^+$.

Example 80

Synthesis of (1S)-2-(tert-butylamino)-1-(4-{(1S)-1-[(5-fluoro-4-imidazo[1,2-a]pyridin-3-yl pyrimidin-2-yl)amino]ethyl}phenyl)ethanol [80] (hereinafter, referred to as the compound [80])

(1) 309 mg of 3-(2-chloro-5-fluoropyrimidin-4-yl)imidazo[1,2-a]pyridine [80-1] (hereinafter, referred to as the compound [80-1]) was obtained from 412 mg of 2,4-dichloro-5-fluoropyrimidine (commercially available from Fluorochem Co. Ltd.) and 232 mg of 2-aminopyridine according to the methods of EXAMPLE 67-(1) and (2).

(2) 51 mg of the title compound [80] (hereinafter, referred to as the compound [80]) was obtained as a white solid from 102 mg of the compound [67-3] and 70 mg of the compound [80-1] according to the method of EXAMPLE 67-(4).

The spectral data of the compound [80] are shown below.
$^1$H-NMR (CDCl$_3$) δ: 9.36 (br, 1H), 8.42 (d, J=3.9 Hz, 1H), 8.21 (d, J=3.9 Hz, 1H), 7.70 (d, J=9.3 Hz, 1H), 7.44-7.38 (m, 4H), 7.34-7.31 (m, 1H), 7.26 (s, 1H), 6.79-6.75 (m, 1H), 5.45 (d, J=6.8 Hz, 1H), 5.07 (quint, J=73 Hz, 1H), 4.58 (dd, J=3.9 Hz, 8.8 Hz, 1H), 2.87 (dd, J=3.9 Hz, 12.2 Hz, 1H), 2.55 (dd, J=12.2 Hz, 8.8 Hz, 1H), 1.60 (d, J=6.8 Hz, 3H), 1.07 (s, 9H)
mass: 449 (M+1)$^+$.

Example 81

Synthesis of (1S)-2-(tert-butylamino)-1-{4-[(1S)-1-({5-fluoro-4-[8-(trifluoromethyl)imidazo[1,2-a]pyridin-3-yl]pyrimidin-2-yl} amino)ethyl]phenyl}ethanol [81] (hereinafter, referred to as the compound [81])

(1) 143 mg of 3-(2-chloro-5-fluoropyrimidin-4-yl) -8-(trifluoromethyl)imidazo[1,2-a]pyridine [81-1] (hereinafter, referred to as the compound [81-1]) was obtained from 113 mg of 2,4-dichloro-5-fluoropyrimidine (commercially available from Fluorochem Co. Ltd) and 104 mg of 3-trifluoromethylpyridine-2-amine (synthesized by the method as described on p. 81 of the International Publication of WO 2006/025567) according to the methods of EXAMPLE 67-(1) and (2).

(2) 30.6 mg of the title compound [81] (hereinafter, referred to as the compound [81]) was obtained as a pale yellow solid from 45.6 mg of the compound [67-3] and 47 mg of the compound [81-1] according to the method of EXAMPLE 67-(4).

The spectral data of the compound [81] are shown below.
$^1$H-NMR (CDCl$_3$) δ: 9.55-9.25 (m, 1H), 8.47 (d, J=3.9 Hz, 1H), 8.26 (d, J=3.9 Hz, 1H), 7.64 (d, J=7.3 Hz, 1H), 7.43-7.37 (m, 4H), 6.85-6.73 (m, 1H), 5.55-5.53 (m, 1H), 5.04-5.01 (m, 1H), 4.59-4.56 (m, 1H), 2.87 (dd, 12.0 Hz, 3.7 Hz, 1H), 2.53 (dd, J=12.0 Hz, 8.8 Hz, 1H), 1.61 (d, J=6.8 Hz, 3H), 1.07 (s, 9H)
mass: 517 (M+1)$^+$.

Example 82

Synthesis of (R)-[4-((1S)-1-{[4-(8-chloroimidazo[1,2-a]pyridin-3-yl)-5-fluoropyrimidin-2-yl]amino}ethyl)phenyl][(2R)-1,2-dimethylpyrrolidin-2-yl]methanol [82] (hereinafter, referred to as the compound [82])

15.6 mg of the title compound [82] (hereinafter, referred to as the compound [82]) was obtained as a yellow solid from 34.2 mg of the compound [65-4] and 30 mg of the compound [67-2] according to the methods of EXAMPLE 67-(3) and (4).

The spectral data of the compound [82] are shown below.
$^1$H-NMR (CDCl$_3$) δ: 9.27-9.05 (m, 1H), 8.39 (d, J=3.9 Hz, 1H), 8.24 (d, J=3.9 Hz, 1H), 7.42-7.30 (m, 5H), 6.78-6.70 (m, 1H), 5.01-4.99 (m, 1H), 4.36 (s, 1H), 3.11-3.07 (m, 1H), 2.52-2.46 (m, 1H), 2.26 (s, 3H), 2.09 (s, 3H), 1.75-1.53 (m, 2H), 1.60 (d, J=6.8 Hz, 3H), 1.25-1.21 (m, 1H), 0.86 (s, 3H)
mass: 495, 497 (M+1)$^+$.

Example 83

Synthesis of [4-((1S)-1-{[4-(8-chloroimidazo[1,2-a]pyridin-3-yl)-5-fluoropyrimidin-2-yl]amino}ethyl)phenyl][(2S)-1,2-dimethylpyrrolidin-2-yl]methanol [83] (hereinafter, referred to as the compound [83])

(1) 1.69 g of tert-butyl((1S)-1-{4-[[(2S)-1,2-dimethylpyrrolidin-2-yl](hydroxy)methyl]phenyl}ethyl)carbamate [83-1] (hereinafter, referred to as the compound [83-1]) was obtained from 2.55 g of the compound [634a] according to the methods of EXAMPLES 54 and 55-(1).

(2) 10.5 mg of the title compound [83] (hereinafter, referred to as the compound [83]) was obtained from 30 mg of the compound [83-1] and 18.4 mg of the compound [67-2] according to the methods of EXAMPLE 67-(3) and (4).

The spectral data of the compound [83] are shown below.
$^1$H-NMR (CDCl$_3$) δ: 9.48-9.35 (m, 1H), 8.42 (d, J=3.4 Hz, 1H), 8.24 (d, J=3.9 Hz, 1H), 7.42-7.28 (m, 5H), 6.78-6.70 (m, 1H), 5.05-5.03 (m, 1H), 4.37 (s, 1H), 3.12-3.07 (m, 1H), 2.51-2.47 (m, 1H), 2.08 (s, 3H), 1.85 (s, 3H), 1.85-1.71 (m, 3H), 1.59 (d, J=6.8 Hz, 3H), 0.85 (s, 3H)
mass: 495, 497 (M+1)$^+$.

Examples 84 and 85

Synthesis of 1-[4-((1S)-1-{[4-(8-chloroimidazo[1,2-a]pyridin-3-yl)-5-fluoropyrimidin-2-yl]amino}ethyl)phenyl]-2-(dimethylamino)-2-methylpropan-1-ol [84] (hereinafter, referred to as the compound [84]) and [85] (hereinafter, referred to as the compound [85]) (here, the compound [84] and the compound [85] are diastereomers. Please see Table 14)

(1) 51 g of dimethylsulfoxide was dissolved in 70 mL of dichloromethane, and the temperature of the solution was kept at −78° C. Then, 160 mL of a dichloromethane solution in which 59.1 g of oxalyl dichloride is dissolved was added thereto. The mixture was stirred at the same temperature for 30 minutes, and thereafter 120 mL of a dichloromethane solution in which 18.2 g of 2-(dimethylamino)-2-methylpropan-1-ol is dissolved was added thereto. The mixture was stirred at the same temperature for 20 minutes, 107 g of triethylamine was added thereto, and the mixture was stirred at the same temperature for 40 minutes. The reaction mixture was warmed to room temperature, and then diluted with dichloromethane. The obtained organic layer was washed with a saturated aqueous sodium hydrogen carbonate solution and saturated brine, sequentially, and dried over anhydrous magnesium sulfate. Then, the insolubles were filtered, and the filtrate was concentrated under reduced pressure. The obtained residue was purified by distillation under reduced pressure to obtain 11.1 g of 2-(dimethylamino)-2-methylpropanal [84-1] (hereinafter, referred to as the compound [84-1]).

(2) 12.8 g of tert-butyl ((1S)-1-{4-[2-(dimethylamino)-1-hydroxy-2-methylpropyl]phenyl}ethyl)carbamate [84-2] (hereinafter, referred to as the compound [84-2]) was obtained from 24.1 g of the compound [1-1] and 11.1 g of the compound [84-1] according to the methods of EXAMPLES 63 and 64-(4).

(3) 2.31 g of a mixture of the title compounds [84] and [85] was obtained from 6.24 g of the compound [84-2] and 2.34 g of the compound [67-2] according to the methods of EXAMPLES 67-(3) and (4).

(4) 70.2 mg of a mixture of the compounds [84] and [85] was separated on Chiralcel AD-H.
Conditions for optical separation are as follows.
Column: Chiralcel AD-H (Chiralcel AD-H, manufactured by DAICEL CHEMICAL INDUSTRIES, LTD.), diameter of 20 mm, and length of 250 mm
Eluent: Hexane/2-propanol/diethylamine=75/25/0.1
Flow rate: 12 mL/min
The obtained solution was concentrated under reduced pressure to obtain 22.5 mg of the title compound [84] (RT=11.5 minutes) and 21 mg of the title compound [85] (RT=22.3 minutes).

The spectral data of the compound [84] are shown below.
$^1$H-NMR (CD$_3$OD) δ: 8.37 (s, 1H), 8.29 (s, 1H), 7.75 (d, J=7.0 Hz, 1H), 7.51-7.42 (m, 5H), 7.21-7.05 (m, 1H), 5.12-5.01 (m, 1H), 4.95 (s, 1H), 2.94 (s, 3H), 2.80 (s, 3H), 1.58 (d, J=7.0 Hz, 3H), 1.16 (s, 3H), 1.13 (s, 3H)
mass: 483, 485 (M+1)$^+$ The spectral data of the compound [85] are shown below.
$^1$H-NMR ((CD$_3$OD) δ: 8.38 (s, 1H), 8.29 (s, 1H), 7.75 (d, J=7.0 Hz, 1H), 7.51-7.43 (m, 5H), 7.19-7.04 (m, 1H), 5.10-5.01 (m, 1H), 4.96 (s, 1H), 2.94 (s, 3H), 2.80 (s, 3H), 1.58 (d, J=7.0 Hz, 3H), 1.17 (s, 3H), 1.12 (s, 3H)
mass: 483, 485 (M+1)$^+$ Example 86

Synthesis of 1-[4-((1S)-1-{[4-(8-chloroimidazo[1,2-a]pyridin-3-yl)-5-fluoropyrimidin-2-yl]amino}ethyl)phenyl]-2-methyl-2-(methylamino)propan-1-ol [86] (hereinafter, referred to as the compound [86])

(1) To a solution prepared by dissolving 595 mg of benzaldehyde in 10 mL of ethanol, 500 mg of 2-amino-2-methylpropan-1-ol was added at room temperature, and the mixture was heated under reflux for 4 hours. To the reaction mixture, 1.06 g of sodium borohydride was added at room temperature, and the mixture was stirred at the same temperature for 1.5 hours. To the reaction mixture, a 1 M aqueous sodium hydroxide solution was added, and the mixture was extracted with ethyl acetate. The obtained organic layer was washed with saturated brine, and dried over anhydrous magnesium sulfate. Then, the insolubles were filtered, and the filtrate was concentrated under reduced pressure. To a solution prepared by dissolving the obtained residue and 674 mg of paraformaldehyde in 7 mL of methanol, 705 mg of sodium cyanoborohydride was added at room temperature, and the mixture was stirred at the same temperature for 4.5 hours. To the reaction mixture, a 1 M aqueous sodium hydroxide solution was added, and the mixture was extracted with ethyl acetate. The obtained organic layer was washed with saturated brine, and dried over anhydrous magnesium sulfate. Then, the insolubles were filtered, and the filtrate was concentrated under reduced pressure. The obtained residue was purified by silica gel column chromatography (eluent: hexane/ethyl acetate=100/0 to 70/30) to obtain 632 mg of 2-amino-2-methylpropan-1-ol [86-1] (hereinafter, referred to as the compound [86-1]).

(2) To a solution prepared by dissolving 417 mg of the compound [86-1] and 1.09 g of triethylamine in 5 mL of dimethylsulfoxide, 859 mg of a sulfur trioxide pyridine complex was added at room temperature, and the mixture was stirred for 1.5 hours. To the reaction mixture, a saturated aqueous sodium hydrogen carbonate solution was added, and the mixture was extracted with ethyl acetate. The obtained organic layer was washed with water and saturated brine, sequentially, and dried over anhydrous magnesium sulfate. Then, the insolubles were filtered, and the filtrate was concentrated under reduced pressure. The obtained residue was purified by silica gel column chromatography (eluent: hexane/ethyl acetate=100/0 to 80/20) to obtain 305 mg of 2-[benzyl(methyl)amino]-2-methylpropanal [86-2] (hereinafter, referred to as the compound [86-2]).

(3) 12.8 g of tert-butyl [(1S)-1-(4-{2-[benzyl(methyl)amino]-1-hydroxy-2-methylpropyl}phenyl)ethyl]carbamate [86-3] (hereinafter, referred to as the compound [86-3]) was obtained from 398 mg of the compound [1-1] and 305 mg of the compound [86-2] according to the methods of EXAMPLES 63 and 64-(4).

(4) 227 mg of the compound [86-3] was dissolved in 7 mL of methanol, and 114 mg of a 20% palladium/carbon catalyst was added thereto. The mixture was stirred at room temperature for 1 hour under hydrogen atmosphere. The catalyst was filtered through Celite, and the filtrate was concentrated under reduced pressure to obtain 188 mg of tert-butyl((1S)-1-{4-[1-hydroxy-2-methyl-2-(methylamino)propyl]phenyl}ethyl) carbamate [86-4] (hereinafter, referred to as the compound [86-4]).

(5) 140 mg of the title compound [86] (hereinafter, referred to as the compound [86]) was obtained from 206 mg of the compound [86-4] and 151 mg of the compound [67-2] according to the methods of EXAMPLE 67-(3) and (4).

The spectral data of the compound [86] are shown below.
$^1$H-NMR (CDCl$_3$) δ: 9.43-9.26 (m, 1H1/2), 9.25-9.07 (m, 1H1/2), 8.42-8.39 (m, 1H), 8.25-8.23 (m, 1H), 7.41-7.36 (m, 5H), 6.76-6.67 (m, 1H), 5.52 (s, 1H1/2), 5.51 (s, 1H1/2), 5.09-4.98 (m, 1H), 4.44 (s, 1H1/2), 4.42 (s, 1H1/2), 2.36 (s, 3H), 1.60 (d, J=7.0 Hz, 3H), 1.04 (s, 3H1/2), 1.02 (s, 3H 1/2), 0.83 (s, 3H1/2), 0.82 (s, 3H1/2)
mass: 469, 471 (M+1)$^+$ Example 87

Synthesis of (1-tert-butylpiperidin-4-yl)[4-((1S)-1-{[4-(8-chloroimidazo[1,2-a]pyridin-3-yl)-5-fluoro-pyrimidin-2-yl]amino}ethyl)phenyl]methanol [87] (hereinafter, referred to as the compound [87])

(1) 6.52 g of diisopropylamine was dissolved in 24 mL of tetrahydrofuran, and the solution was cooled on ice. Then, 2.91 mL of n-butyl lithium (a 2.66 M hexane solution) was added thereto. After stirring at the same temperature for 30 minutes, the mixture was kept at −78° C. To the reaction mixture, 3.87 mL of trimethylsilyldiazomethane (a 2 M hexane solution) was added at the same temperature, and the mixture was stirred at the same temperature for 1 hour. To the reaction mixture, a solution prepared by dissolving 1 g of 1-tert-butylpyrimidin-4-one (synthesized by the method as described in J. Org. Chem., 2005, 70, 1930) in 6 mL of tetrahydrofuran was added at the same temperature, and the mixture was stirred at the same temperature for 1.5 hours, and heated overnight under reflux. To the reaction mixture, water was added, and the mixture was extracted with 200 mL of ethyl acetate. The obtained organic layer was dried over anhydrous sodium sulfate. Then, the insolubles were filtered, and the filtrate was concentrated under reduced pressure. The obtained residue was dissolved in 120 mL of ethyl acetate, and 24 g of silica gel was added thereto at room temperature. The mixture was stirred at the same temperature for 1.5 hours. The insolubles were filtered, and the filtrate was concentrated under reduced pressure to obtain 830 mg of 1-tert-butylpiperidin-4-carboaldehyde [87-1] (hereinafter, referred to as the compound [87-1]).

(2) 5.5 mg of the title compound [87] (hereinafter, referred to as the compound [87]) was obtained from 276 mg of the compound [87-1] and 30 mg of the compound [67-2] according to the methods of EXAMPLES 84 and 85-(2) and (3).

The spectral data of the compound [87] are shown below.
$^1$H-NMR (CDCl$_3$) δ: 9.11 (brs, 11H), 8.35 (d, J=3.9 Hz, 1H1/2), 8.30 (d, J=3.9 Hz, 1H 1/2), 8.21 (d, J=3.5 Hz, 1H1/2), 8.20 (d, J=3.5 Hz, 1H1/2), 7.42-7.29 (m, 5H), 6.70-6.60 (m, 1H), 5.57-5.51 (m, 1H), 5.03-4.95 (m, 1H), 4.40 (s, 1H1/2), 4.38 (s, 1H1/2), 3.22-3.13 (m, 1H), 3.02-2.90 (m, 1H), 2.19-1.78 (m, 6H), 1.59 (d, J=7.0 Hz, 3H), 1.27-1.24 (m, 1H), 1.11 (s, 9H1/2), 1.10 (s, 9H1/2)
mass: 537, 539 (M+1)$^+$.

Examples 88 and 89

Synthesis of [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol [88] (hereinafter, referred to as the compound [88]) and [89] (hereinafter, referred to as the compound [89]) (here, the compound [88] and the compound [89] are diastereomers. Please see Table 15)

(1) 9.94 g of tert-butyl[(1S)-1-(4-{[1-(diphenylmethyl) azetidin-3-yl]carbonyl}phenyl)ethyl]carbamate [88-1] (hereinafter, referred to as the compound [88-1]) was obtained from 1-benzhydrylazetidine-3-carboxylic acid according to the methods of EXAMPLE 1-(1) and (2).

(2) 9.94 g of the compound [88-1] was dissolved in 100 mL of tetrahydrofuran and 20 mL of methanol, 799 mg of sodium borohydride was added thereto at room temperature, and the mixture was stirred at the same temperature for 2.5 hours. To the reaction mixture, water was added, and the mixture was extracted with chloroform. The obtained organic layer was dried over anhydrous magnesium sulfate. Then, the insolubles were filtered, and the filtrate was concentrated under reduced pressure. The obtained residue was purified by silica gel column chromatography (eluent: hexane/ethyl acetate=100/0 to 30/70) to obtain 632 mg of tert-butyl ((1S)-1-{4-[[1-(diphenyl methyl)azetidin-3-yl](hydroxy)methyl] phenyl}ethyl)carbamate [88-2] (hereinafter, referred to as the compound [88-2]).

(3) 6.26 g of tert-butyl ((1S)-1-{4-[hydroxy(1-isopropylazetidine 3-yl)methyl]phenyl}ethyl)carbamate [88-3] (hereinafter, referred to as the compound [88-3]) was obtained from 9.79 g of the compound [88-2] according to the methods of EXAMPLE 33-(3) and (4).

(4) 135 mg of a mixture of the title compounds [88] and [89] was obtained from 720 mg of the compound [88-3] and 200 mg of the compound [67-2] according to the methods of EXAMPLE 67-(3) and (4).

(5) 130 mg of the mixture of the compounds [88] and [89] was separated on Chiralcel AD-H.

Conditions for optical separation are as follows.
Column: Chiralcel AD-H (Chiralcel AD-H, manufactured by DAICEL CHEMICAL INDUSTRIES, LTD.), diameter of 20 mm, and length of 250 mm
Eluent: Hexane/ethanol/diethylamine=70/30/1
Flow rate: 12 mL/min The obtained solution was concentrated under reduced pressure to obtain 36 mg of the title compound [88] (RT=11.4 minutes) and 63 mg of the title compound [89] (RT=21.8 minutes).

The spectral data of the compound [88] are shown below.
$^1$H-NMR (CDCl$_3$) δ: 8.90 (br, 1H), 8.22-8.16 (m, 2H), 7.43-7.38 (m, 4H), 7.32 (d, J=7.3 Hz, 1H), 7.27 (s, 1H), 6.60 (brs, 1H), 5.58 (brs, 1H), 4.95 (brs, 1H), 4.89 (d, J=6.8 Hz, 1H), 3.22 (d, J=5.9 Hz, 2H), 3.15-3.12 (m, 1H), 3.05-3.04 (m, 1H), 2.68-2.65 (m, 1H), 2.30-2.25 (m, 1H)
mass: 495, 497 (M+1)$^+$.

The spectral data of the compound [89] are shown below.
$^1$H-NMR (CDCl$_3$) δ: 8.99 (br, 1H), 8.29 (brs, 1H), 8.18-8.17 (m, 1H), 7.41-7.37 (m, 4H), 7.32 (d, J=6.8 Hz, 1H), 7.27 (s, 1H), 6.57 (br, 1H), 5.61 (br, 1H), 4.99-4.95 (m, 1H), 4.87 (d, J=6.3 Hz, 1H), 3.21 (d, J=6.3 Hz, 2H), 3.14-3.10 (m, 1H), 3.05-3.02 (m, 1H), 2.66-2.62 (m, 1H), 2.27 (quint, J=6.3 Hz, 1H), 1.58 (d, J=6.8 Hz, 3H), 0.89 (d, J=5.9 Hz, 6H)
mass: 495, 497 (M+1)$^+$.

Examples 90 and 91

Synthesis of [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol [90] (hereinafter, referred to as the compound [90]) and [91] (hereinafter, referred to as the compound [91]) (here, the compound [90] and the compound [91] are diastereomers. Please see Table 15)

(1) 156 mg of a mixture of title compounds [90] and [91] was obtained from 415 mg of the compound [33-4] and 240 mg of the compound [67-2] according to the methods of EXAMPLE 67-(3) and (4).

(2) 156 mg of the mixture of the compounds [90] and [91] was separated on Chiralcel AD-H.

Conditions for optical separation are as follows.

Column: Chiralcel AD-H (Chiralcel AD-H, manufactured by DAICEL CHEMICAL INDUSTRIES, LTD.), diameter of 20 mm, and length of 250 mm Eluent: Hexane/2-propanol/diethylamine=70/30/0.1

Flow rate: 12 mL/min

The obtained solution was concentrated under reduced pressure to obtain 40.5 mg of the title compound [90] (RT=13.5 minutes) and 39.8 mg of the title compound [91] (RT=24.2 minutes).

The spectral data of the compound [90] are shown below.
$^1$H-NMR (DMSO-$d_6$): 8.44 (brs, 1H), 8.32 (s, 1H), 7.99 (d, J=7.3 Hz, 1H), 7.71 (s, 1H), 7.36 (d, J=8.0 Hz, 2H), 7.21 (d, 8.0 Hz, 2H), 7.1-7.0 (brs, 1H), 5.0 (m, 2H), 4.2 (m, 1H), 2.8-2.5 (m, 2H), 2.0-1.6 (m, 4H), 1.49 (d, 6.8 Hz, 3H), 1.4-0.9 (m, 4H), 0.87 (d, 5.9 Hz, 6H)
mass: 523 (M+1)$^+$.

The spectral data of the compound [91] are shown below.
$^1$H-NMR (DMSO-$d_6$): 8.45 (brs, 1H), 8.32 (s, 1H), 7.99 (d, J=7.3 Hz, 1H), 7.71 (s, 1H), 7.35 (d, J=8.3 Hz, 2H), 7.21 (d, 7.8 Hz, 2H), 7.1-6.9 (brs, 1H), 5.01 (m, 2H), 4.1 (m, 1H), 2.7 (m, 1H), 2.6-2.5 (m, 1H), 2.0-1.7 (m, 4H), 1.49 (d, 6.8 Hz, 3H), 1.4-0.9 (m, 4H), 0.86 (m, 6H)
mass: 523 (M+1)$^+$.

Example 92

Synthesis of (1-tert-butylazetidin-3-yl) [4-((1S)-1-{[4-(8-chloroimidazo[1,2-a]pyridin-3-yl)-5-fluoropyrimidin-2-yl]amino}ethyl)phenyl]methanol [92] (hereinafter, referred to as the compound [92])

34 mg of the title compound [92] (hereinafter, referred to as the compound [92]) was obtained as a pale yellow solid from 980 mg of 1-tert-butylazetidine-3-carboxylic acid (synthesized by the method as described in Chem. Pharm. Bull., 1974, 22, 1490) and 35.5 mg of the compound [67-2] according to the methods of EXAMPLES 88, and 89-(1) to (4).

The spectral data of the compound [92] are shown below.
$^1$H-NMR (CDCl$_3$) δ: 9.21 (br, 1H), 8.40 (dd, J=3.9 Hz, 7.3 Hz, 1H), 8.24 (d, J=2.9 Hz, 1H), 7.40-7.37 (m, 5H), 7.26 (s, 1H), 6.68-6.64 (m, 1H), 5.48 (d, J=5.9 Hz, 1H), 5.04-5.01 (m, 1H), 4.92 (dd, J=5.4 Hz, 2.4 Hz, 1H), 3.28-3.21 (m, 1H), 3.19-3.15 (m, 1H), 3.12-3.06 (m, 2H), 2.56-2.49 (m, 1H), 1.59 (d, J=6.8 Hz, 3H), 0.93 (s, 9H)
mass: 509, 511 (M+1)$^+$.

Example 93

Synthesis of (1S)-2-(tert-butylamino)-1-{4-[(1S)-1-({4-[8-(difluoromethyl)imidazo[1,2-a]pyridin-3-yl]-5-fluoropyrimidin-2-yl}amino)ethyl]phenyl}ethanol [93] (hereinafter, referred to as the compound [93])

(1) 180 mg of 3-(2-chloro-5-fluoropyrimidin-4-yl)imidazo[1,2-a]pyridin-8-carboaldehyde [93-1] (hereinafter, referred to as the compound [93-1]) was obtained from 568 mg of 2,4-dichloro-5-fluoropyrimidine (commercially available from Fluorochem Co. Ltd) and 415 mg of 2-aminonicotinaldehyde (commercially available from Aldrich Corporation) according to the methods of EXAMPLE 67-(1) and (2).

(2) 97 mg of 3-(2-chloro-5-fluoropyrimidin-4-yl)-8-(difluoromethyl)imidazo[1,2-a]pyridine [93-2] (hereinafter, referred to as the compound [93-2]) was obtained from 180 mg of the compound [93-1] according to the method of EXAMPLE 10-(2).

(3) 12.9 mg of the title compound [93] (hereinafter, referred to as the compound [93]) was obtained from 33.5 mg of the compound [67-3] and 30 mg of the compound [93-2] according to the method of EXAMPLE 67-(4).

The spectral data of the compound [93] are shown below.
$^1$H-NMR (CDCl$_3$) δ: 9.36 (brs, 1H), 8.43-8.40 (m, 1H 4/5), 8.25-8.22 (m, 1H 4/5), 7.97-7.93 (m, 1H1/5+1H1/5), 7.63-7.58 (m, 1H 4/5), 7.50-7.37 (m, 4H+1H1/5+1H1/5), 7.32 (t, J=55.1 Hz, 1H), 6.87-6.79 (m, 1H 4/5), 5.57-5.51 (m, 1H 4/5), 5.06-5.00 (m, 1H 4/5), 4.67-4.57 (m, 1H 4/5+1H 1/5+1H1/5), 4.32-4.26 (m, 1H1/5), 2.98-2.91 (m, 1H1/5), 2.90-2.84 (m, 1H 4/5), 2.59-2.51 (m, 1H), 1.62-1.58 (m, 3H), 1.12-1.10 (m, 9H1/5), 1.09-1.06 (m, 9H 4/5)
mass: 499 (M+1)$^+$.

INDUSTRIAL APPLICABILITY

The compound of the present invention has an excellent inhibitory effect against PLK I and cell proliferation, and thus it is expected to serve as a useful antitumor agent in the field of medicine.

---

What is claimed is:

1. A compound of Formula [I]:

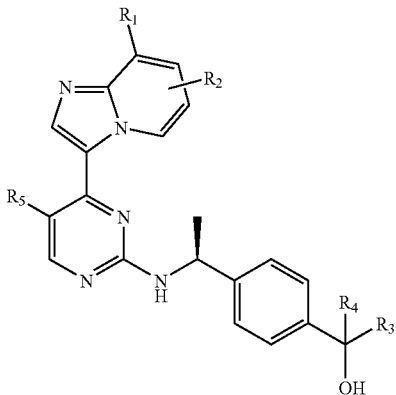

or a pharmaceutically acceptable salt or ester thereof wherein:

$R_1$ is a substituent selected from <Substituent Group α>; a lower alkyl group which may be substituted with one or more substituents selected from <Substituent Group α>; or a cyclopropyl group, where the <Substituent Group α> is a halogen atom; and $R_2$ is a hydrogen atom;

one of $R_3$ and $R_4$ is a hydrogen atom, while the other one of $R_3$ and $R_4$ is:

a) a lower alkyl group substituted with $NR_aR_b$, where $R_a$ and $R_b$, which may be the same or different, are each a hydrogen atom, a lower alkyl group, a benzyl group, or a cycloalkyl group having three to six carbon atoms, wherein the cycloalkyl group may be substituted with one or more substituents, which may be the same or different, selected from the following 1) to 3):

1) a lower alkyl group;

2) a substituent selected from <Substituent Group β>; and 3) a lower alkyl group substituted with one or more substituents selected from <Substituent Group β>; and the cycloalkyl group may include an unsaturated bond;

b) a 4- to 6-membered aliphatic heterocyclic group selected from an azetidinyl group, a pyrrolidinyl group, a piperidinyl group, and a piperazinyl group; or c) a lower alkyl group substituted with a 4- to 6-membered aliphatic heterocyclic group selected from an azetidinyl group, a pyrrolidinyl group, a piperidinyl group, and a piperazinyl group, wherein the aliphatic heterocyclic group may be substituted with one or more substituents, which may be the same or different, selected from the following 1) to 4):

1) a lower alkyl group;

2) a substituent selected from the <Substituent Group β>;

3) a lower alkyl group substituted with one or more substituents selected from the <Substituent Group β>; and 4) a cycloalkyl group having 3 to 6 carbon atoms, which may be substituted with one or more substituents selected from the <Substituent Group β>;

$R_5$ is a hydrogen atom, a cyano group, a halogen atom, or a methyl group; and

<Substituent Group α> and <Substituent Group β> are defined as below:

<Substituent Group α>: a halogen atom, a hydroxy group, a nitro group, a cyano group, an amino group, a carbamoyl group, an aminosulfonyl group, an imino group, a lower alkylamino group, a di-lower alkylamino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, and a carboxyl group; and <Substituent Group β>: a halogen atom, a hydroxy group, a nitro group, a cyano group, an amino group, a carbamoyl group, an aminosulfonyl group, an imino group, a lower alkylsulfonyl group, a lower alkylsulfonylamino group, a lower alkoxy group, a lower alkoxycarbonyl group, a lower alkoxycarbonylamino group, a lower alkanoyl group, a lower alkanoyloxy group, a lower alkylthio group, a carboxyl group, and a benzyl group.

2. The compound according to claim 1 or a pharmaceutically acceptable salt or ester thereof, wherein $R_1$ is a lower alkyl group having 1 or 2 carbon atom(s), which may be substituted with 1 to 3 fluorine atoms; a cyclopropyl group; or a chlorine atom.

3. The compound according to claim 2 or a pharmaceutically acceptable salt or ester thereof, wherein the <Substituent Group β> is a halogen atom, a hydroxyl group, an amino group, a lower alkylsulfonyl group, and a lower alkoxy group.

4. The compound according to claim 3 or a pharmaceutically acceptable salt or ester thereof, wherein:

one of $R_3$ and $R_4$ is a hydrogen atom, while the other one of $R_3$ and $R_4$ is:

a) a lower alkyl group substituted with $NR_aR_b$, where $R_a$ and $R_b$, which may be the same or different, are each a hydrogen atom, a lower alkyl group, or a cycloalkyl group having five to six carbon atoms, wherein the cycloalkyl group may be substituted with one or more substituents, which may be the same or different, selected from the following 1) to 3):

1) a lower alkyl group;

2) a substituent selected from <Substituent Group β>; and 3) a lower alkyl group substituted with one or more substituents selected from <Substituent Group β>; or b) a 4- or 6-membered aliphatic heterocyclic group selected from an azetidinyl group, a pyrrolidinyl group and a piperidinyl group, wherein the aliphatic heterocyclic group may be substituted with one or more substituents, which may be the same or different, selected from the following 1) to 3):

1) a lower alkyl group;

2) a substituent selected from the <Substituent Group β>; and 3) a lower alkyl group substituted with one or more substituents selected from the <Substituent Group β>.

5. The compound according to claim 1 or a pharmaceutically acceptable salt or ester thereof, wherein:

$R_1$ is a lower alkyl group having 1 or 2 carbon atom(s), which may be substituted with 1 to 3 fluorine atoms; a cyclopropyl group; or a halogen atom;

$R_2$ is a hydrogen atom;

one of $R_3$ and $R_4$ is a hydrogen atom, while the other one of $R_3$ and $R_4$ is an amino lower alkyl group (wherein said lower alkyl is a linear or branched alkyl group having 1 to 3 carbon atom(s)) which is N-substituted or N,N-disubstituted with a linear or branched alkyl group having 1 to 5 carbon atom(s); a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cycloalkyl group having five to six carbon atoms, wherein the piperidinyl group, the pyrrolidinyl group, and the azetidinyl group each independently may be further substituted with a linear or branched alkyl group having 1 to 3 carbon atom(s), and the cycloalkyl group may be substituted with a linear or branched alkyl group having 1 to 3 carbon atom(s) optionally having a hydroxy group; and $R_5$ is a cyano group, a halogen atom, or a methyl group.

6. The compound according to claim 5 or a pharmaceutically acceptable salt or ester thereof, wherein:

$R_1$ is a methyl group, an ethyl group, a difluoromethyl group, a trifluoromethyl group, a cyclopropyl group, or a chlorine atom;

$R_2$ is a hydrogen atom;

one of $R_3$ and $R_4$ is a hydrogen atom, while the other one of $R_3$ and $R_4$ is a linear or branched alkyl group having 1 to 3 carbon atom(s) which is substituted with a dimethylamino group, an isopropylamino group, 1,1-dimethylpropylamino group, or t-butylamino group; a piperidinyl group which is N-substituted with a linear or branched alkyl group having 1 to 5 carbon atom(s); a pyrrolidinyl group which is N-substituted with a linear or branched alkyl group having 1 to 5 carbon atom(s); an azetidinyl group which is N-substituted with a linear or branched alkyl group having 1 to 5 carbon atom(s); or a cyclopentyl group which may be substituted with a methyl group or a hydroxymethyl group, wherein the piperidinyl group, the pyrrolidinyl group, and the azetidinyl group each independently may be further substituted with a linear or branched alkyl group having 1 to 3 carbon atom(s); and $R_5$ is a cyano group, a fluorine atom, or a methyl group.

7. The compound which is:

(a) 2-[((1S)-1-{4-[2-(tert-butylamino)-1-hydroxyethyl]phenyl}ethyl)amino]-4-(8-ethylimidazo[1,2-a]pyridin-3-yl)pyrimidine-5-carbonitrile;

(b) (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol;

(c) 2-[((1S)-1-{4-[hydroxy(pyridin-2-yl)methyl]phenyl}ethyl)amino]-4-(8-methylimidazo[1,2-a]pyridin-3-yl)pyrimidine-5-carbonitrile;

(d) 4-(8-ethylimidazo[1,2-a]pyridin-3-yl)-2-({(1S)-1-[4-(4-hydroxy-1-methylpiperidin-4-yl)phenyl]ethyl}amino)pyrimidine-5-carbonitrile;

(e) 4-(8-ethylimidazo[1,2-a]pyridin-3-yl)-2-[((1S)-1-{4-[hydroxy(1-isopropylpiperidin-4-yl)methyl]phenyl}ethyl)amino]pyrimidine-5-carbonitrile;

(f) 4-(8-cyclopropylimidazo[1,2-a]pyridin-3-yl)-2-[((1S)-1-{4-[hydroxy(1-methylpiperidin-4-yl)methyl]phenyl}ethyl)amino]pyrimidine-5-carbonitrile;

(g) 4-(8-chloroimidazo[1,2-a]pyridin-3-yl)-2-[((1S)-1-{4-[(1-cyclopropylpiperidin-4-yl)(hydroxy)methyl]phenyl}ethyl)amino]pyrimidine-5-carbonitrile;

(h) 4-(8-ethylimidazo[1,2-a]pyridin-3-yl)-2-[((1S)-1-{4-[hydroxy(1-methylpiperidin-3-yl)methyl]phenyl}ethyl)amino]pyrimidine-5-carbonitrile;

(i) 2-{[(1S)-1-(4-{hydroxy[1-methylpyrrolidin-2-yl]methyl}phenyl)ethyl]amino}-4-(8-methylimidazo[1,2-a]pyridin-3-yl)pyrimidine-5-carbonitrile;

(j) 2-[((1S)-1-{4-[2-(tert-butylamino)-1-hydroxyethyl]phenyl}ethyl)amino]-4-(8-chloroimidazo[1,2-a]pyridin-3-yl)pyrimidine-5-carbonitrile;

(k) 2-[((1S)-1-{4-[2-(tert-butylamino)-1-hydroxyethyl]phenyl}ethyl)amino]-4-[8-(difluoromethyl)imidazo[1,2-a]pyridin-3-yl]pyrimidine-5-carbonitrile;

(l) 4-(8-cyclopropylimidazo[1,2-a]pyridin-3-yl)-2-[((1S)-1-{4-[(1,2-dimethylpyrrolidin-2-yl)(hydroxy)methyl]phenyl}ethyl)amino]pyrimidine-5-carbonitrile;

(m) (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol;

(n) (1S)-1-[4-((1S)-1-{[4-(8-chloroimidazo[1,2-a]pyridin-3-yl)-5-fluoropyrimidin-2-yl]amino}ethyl)phenyl]-2-[(1,1-dimethylpropyl)amino]ethanol;

(o) (1S)-1-[4-((1S)-1-{[4-(8-chloroimidazo[1,2-a]pyridin-3-yl)-5-fluoropyrimidin-2-yl]amino}ethyl)phenyl]-2-[(1-methylcyclopentyl)amino]ethanol;

(p) (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol;

(q) (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol;

(r) (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol;

(s) (1S)-2-(tert-butylamino)-1-{4-[(1S)-1-({5-fluoro-4-[8-(trifluoromethyl)imidazo[1,2-a]pyridin-3-yl]pyrimidin-2-yl}amino)ethyl]phenyl}ethanol;

(t) [4-((1S)-1-{[4-(8-chloroimidazo[1,2-a]pyridin-3-yl)-5-fluoropyrimidin-2-yl]amino}ethyl)phenyl](1,2-dimethylpyrrolidin-2-yl)methanol;

(u) 1-[4-((1S)-1-{[4-(8-chloroimidazo[1,2-a]pyridin-3-yl)-5-fluoropyrimidin-2-yl]amino}ethyl)phenyl]-2-(dimethylamino)-2-methylpropan-1-ol;

(v) [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol;

(w) [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol; or (x) (1S)-2-(tert-butylamino)-1-{4-[(1S)-1-({4-[8-(difluoromethyl)imidazo[1,2-a]pyridin-3-yl]-5-fluoropyrimidin-2-yl}amino)ethyl]phenyl}ethanol, or a pharmaceutically acceptable salt or ester thereof 8. A pharmaceutical composition comprising, together with a pharmaceutically acceptable carrier or diluent, at least one compound according to claim 1 as an active ingredient.

9. A combined preparation for simultaneous, separate, or sequential administration, comprising two separate preparations:

a preparation including, together with a pharmaceutically acceptable carrier or diluent, the compound of claim 1 which is represented by the Formula [I]or a pharmaceutically acceptable salt or ester thereof; and a preparation including, together with a pharmaceutically acceptable carrier or diluent, an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents, or a pharmaceutically acceptable salt or ester thereof, wherein:

the antitumor alkylating agents are nitrogen mustard N-oxide, cyclophosphamide, ifosfamide, melphalan, busulfan, mitobronitol, carboquone, thiotepa, ranimustine, nimustine, temozolomide, and carmustine;

the antitumor antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, and pemetrexed disodium;

the antitumor antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin;

the plant-derived antitumor agents are vincristine, vinblastin, vindesine, etoposide, sobuzoxane, docetaxel, paclitaxel, and vinorelbine;

the antitumor platinum complex compounds are cisplatin, carboplatin, nedaplatin, and oxaliplatin;

the antitumor camptothecin derivatives are irinotecan, topotecan, and camptothecin;

the antitumor tyrosine kinase inhibitors are gefitinib, imatinib, and erlotinib;

the monoclonal antibodies are cetuximab, bevacizumab, rituximab, bevacizumab, alemtuzumab, and trastuzumab;

the interferons are interferon α, interferon α-2a, interferon α-2b, interferon β, interferon γ-1a, and interferon γ-nl;

the biological response modifiers are krestin, lentinan, sizofiran, picibanil, and ubenimex; and the other antitumor agents are mitoxantrone, L-asparaginase, procarbazine, dacarbazine, hydroxycarbamide, pentostatin, tretinoin, alefacept, darbepoetin alfa, anastrozole, exemestane, bicalutamide, leuproreline, flutamide, fulvestrant, pegaptanib octasodium, denileukin diftitox, aldesleukin, thyrotropin alpha, arsenic trioxide, bortezomib, capecitabine, and goserelin.

10. The preparation according to claim 9 wherein one of or both of the two separate preparations is/are oral preparation(s) or parental preparation(s).

11. The preparation according to claim 9 which is further combined with at least one preparation comprising, together with a pharmaceutically acceptable carrier or diluent: an antitumor agent selected from the group consisting of antitumor alkylating agents, antitumor antimetabolites, antitumor antibiotics, plant-derived antitumor agents, antitumor platinum complex compounds, antitumor camptothecin derivatives, antitumor tyrosine kinase inhibitors, monoclonal antibodies, interferons, biological response modifiers, and other antitumor agents, wherein the definition of each antitumor agent is the same as defined in claim 9; or a pharmaceutically acceptable salt or ester thereof.

12. The preparation according to claim 9 wherein:
among the combined preparations, one preparation comprises, together with a pharmaceutically acceptable carrier or diluent, (a) 2-[((1S)-1-{4-[2-(tert-butylamino)-1-hydroxyethyl]phenyl}ethyl)amino]-4-(8-ethylimidazo[1,2-a]pyridin-3-yl)pyrimidine-5-carbonitrile;

(b) (1R)-1-[4-((1S)-1-{[5-bromo-4-(8-ethylimidazo[1,2-a]pyridin-3-yl)pyrimidin-2-yl]amino}ethyl)phenyl]-2-(tert-butylamino)ethanol;

(c) 2-[((1S)-1-{4-[hydroxy(pyridin-2-yl)methyl]phenyl}ethyl)amino]-4-(8-methylimidazo[1,2-a]pyridin-3-yl)pyrimidine-5-carbonitrile;

(d) 4-(8-ethylimidazo[1,2-a]pyridin-3-yl)-2-({(1S)-1-[4-(4-hydroxy-1-methylpiperidin-4-yl)phenyl]ethyl}amino)pyrimidine-5-carbonitrile;

(e) 4-(8-ethylimidazo[1,2-a]pyridin-3-yl)-2-[((1S)-1-{4-[hydroxy(1-isopropylpiperidin-4-yl)methyl]phenyl}ethyl)amino]pyrimidine-5-carbonitrile;

(f) 4-(8-cyclopropylimidazo[1,2-a]pyridin-3-yl)-2-[((1S)-1-{4-[hydroxy(1-methylpiperidin-4-yl)methyl]phenyl}ethyl)amino]pyrimidine-5-carbonitrile;

(g) 4-(8-chloroimidazo[1,2-a]pyridin-3-yl)-2-[((1S)-1-{4-[(1-cyclopropylpiperidin-4-yl)(hydroxy)methyl]phenyl}ethyl)amino]pyrimidine-5-carbonitrile;

(h) 4-(8-ethylimidazo[1,2-a]pyridin-3-yl)-2-[((1S)-1-{4-[hydroxy(1-methylpiperidin-3-yl)methyl]phenyl}ethyl)amino]pyrimidine-5-carbonitrile;

(i) 2-{[(1S)-1-(4-{hydroxy[1-methylpyrrolidin-2-yl]methyl}phenyl)ethyl]amino}-4-(8-methylimidazo[1,2-a]pyridin-3-yl)pyrimidine-5-carbonitrile;

(j) 2-[((1S)-1-{4-[2-(tert-butylamino)-1-hydroxyethyl]phenyl}ethyl)amino]-4-(8-chloroimidazo[1,2-a]pyridin-3-yl)pyrimidine-5-carbonitrile; or (k) 2-[((1S)-1-{4-[2-(tert-butylamino)-1-hydroxyethyl]phenyl}ethyl)amino]-4-[8-(difluoromethyl)imidazo[1,2-a]pyridin-3-yl]pyrimidine-5-carbonitrile, (l) 4-(8-cyclopropylimidazo[1,2-a]pyridin-3-yl)-2-[((1S)-1-{4(1,2-dimethylpyrrolidin-2-yl)(hydroxy)methyl]phenyl}ethyl)amino]pyrimidine-5-carbonitrile;

(m) (1S)-2-(tert-butylamino)-1-[4-((1S)-1-{[4-(8-chloroimidazo[1,2-a]pyridin-3-yl)-5-fluoropyrimidin-2-yl]amino}ethyl)phenyl]ethanol;

(n) (1S)-1-[4-((1S)-1-{[4-(8-chloroimidazo [1,2-a]pyridin-3-yl)-5-fluoropyrimidin-2-yl]amino}ethyl)phenyl]-2-[(1,1-dimethylpropyl)amino]ethanol;

(o) (1S)-1-[4-((1S)-1-{[4-(8-chloroimidazo [1,2-a]pyridin-3-yl)-5-fluoropyrimidin-2-yl]amino}ethyl)phenyl]-2-[(1-methylcyclopentyl)amino]ethanol;

(p) (1S)-2-(tert-butylamino)-1-[4-((1S)-1-{[4-(8-cyclopropylimidazo[1,2-a]pyridin-3-yl)-5-methylpyrimidin-2-yl]amino}ethyl)phenyl]ethanol;

(q) (1S)-2-(tert-butylamino)-1-[4-((1S)-1-{[4-(8-chloroimidazo[1,2-a]pyridin-3-yl)-5-methylpyrimidin-2-yl]amino}ethyl)phenyl]ethanol;

(r) (1S)-2-(tert-butylamino)-1-[4-((1S)-1-{[4-(8-cyclopropylimidazo[1,2-a]pyridin-3-yl)-5-fluoropyrimidin-2-yl]amino}ethyl)phenyl]ethanol;

(s) (1S)-2-(tert-butylamino)-1-{4-[(1S)-1-({5-fluoro-4-[8-(trifluoromethyl)imidazo[1,2-a]pyridin-3-yl]pyrimidin-2-yl}amino)ethyl]phenyl}ethanol;

(t) [4-((1S)-1-{[4-(8-chloroimidazo[1,2-a]pyridin-3-yl)-5-fluoropyrimidin-2-yl]amino}ethyl)phenyl](1,2-dimethylpyrrolidin-2-yl)methanol;

(u) 1-[4-((1S)-1-{[4-(8-chloroimidazo[1,2-a]pyridin-3-yl)-5-fluoropyrimidin-2-yl]amino}ethyl)phenyl]-2-(dimethylamino)-2-methylpropan-1-ol;

(v) [4-((1S)-1-{[4-(8-chloroimidazo[1,2-a]pyridin-3-yl)-5-fluoropyrimidin-2-yl]amino}ethyl)phenyl](1-isopropylazetidin-3-yl)methanol;

(w) [4-((1S)-1-{[4-(8-chloroimidazo[1,2-a]pyridin-3-yl)-5-fluoropyrimidin-2-yl]amino}ethyl)phenyl](1-isopropylpiperidin-4-yl)methanol; or (x) (1S)-2-(tert-butylamino)-1-{4-[(1S)-1-({4-[8-(difluoromethyl)imidazo[1,2-a]pyridin-3-yl]-5-fluoropyrimidin-2-yl}amino)ethyl]phenyl}ethanol, or a pharmaceutically acceptable salt or ester thereof.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: artificial
<220> FEATURE:
<223> OTHER INFORMATION: synthetic peptide

<400> SEQUENCE: 1

Asp Glu Leu Met Glu Ala Ser Phe Ala Asp Gln Asp Ala Lys
1               5                   10
```